US008329730B2

(12) United States Patent
Heightman et al.

(10) Patent No.: US 8,329,730 B2
(45) Date of Patent: Dec. 11, 2012

(54) COMPOUNDS

(75) Inventors: Thomas Daniel Heightman, Harlow (GB); John Skidmore, Harlow (GB); Hailong Wang, Shanghai (CN); Colin David Eldred, Stevenage (GB); Jag Paul Heer, Harlow (GB)

(73) Assignee: Glaxo Group Limited, Greenford Middlesex (GB)

( * ) Notice: Subject to any disclaimer, the term of this patent is extended or adjusted under 35 U.S.C. 154(b) by 196 days.

(21) Appl. No.: 12/989,700

(22) PCT Filed: Apr. 29, 2009

(86) PCT No.: PCT/EP2009/055193
§ 371 (c)(1),
(2), (4) Date: Oct. 26, 2010

(87) PCT Pub. No.: WO2009/133136
PCT Pub. Date: Nov. 5, 2009

(65) Prior Publication Data
US 2011/0039889 A1 Feb. 17, 2011

(30) Foreign Application Priority Data
Apr. 30, 2008 (GB) .................................. 0807910.5

(51) Int. Cl.
*C07D 413/04* (2006.01)
*A61K 31/4725* (2006.01)
(52) U.S. Cl. .......................... 514/307; 546/139; 546/148
(58) Field of Classification Search .................. None
See application file for complete search history.

(56) References Cited

U.S. PATENT DOCUMENTS

| 5,137,898 | A | 8/1992 | Klausener et al. .......... 514/365 |
|---|---|---|---|
| 5,182,286 | A | 1/1993 | Seitz et al. .................. 514/256 |
| 5,262,416 | A | 11/1993 | Seitz et al. .................. 514/256 |
| 5,462,943 | A | 10/1995 | Seitz et al. .................. 514/256 |
| 5,514,692 | A | 5/1996 | Aldous et al. ............... 514/314 |
| 5,523,312 | A | 6/1996 | Aldous et al. ............... 514/364 |
| 6,004,565 | A | 12/1999 | Chiba et al. ................ 424/278.1 |
| 6,667,025 | B2 | 12/2003 | Chiba et al. .................... 424/9.1 |
| 7,060,697 | B2 | 6/2006 | Marsilje et al. .......... 514/210.17 |
| 7,199,142 | B2 | 4/2007 | Chen et al. ................... 514/364 |
| 7,417,065 | B2 | 8/2008 | Mi et al. ....................... 514/443 |
| 7,462,629 | B2 | 12/2008 | Pan et al. ...................... 514/307 |
| 2002/0102279 | A1 | 8/2002 | Chiba et al. ................ 424/278.1 |
| 2004/0092603 | A1 | 5/2004 | Chiba et al. ................... 514/651 |
| 2005/0009786 | A1 | 1/2005 | Pan et al. ......................... 514/79 |
| 2005/0014724 | A1 | 1/2005 | Marsilje et al. ................. 514/79 |
| 2005/0014725 | A1 | 1/2005 | Mi et al. ........................... 514/80 |
| 2005/0014728 | A1 | 1/2005 | Pan et al. ....................... 514/114 |
| 2005/0090558 | A1 | 4/2005 | Chiba et al. ................... 514/651 |
| 2005/0245575 | A1 | 11/2005 | Chen et al. ..................... 514/326 |
| 2008/0113961 | A1 | 5/2008 | Nishi et al. ............... 514/210.18 |
| 2008/0188532 | A1 | 8/2008 | Takeuchi et al. .............. 514/381 |
| 2008/0207584 | A1 | 8/2008 | Habashita et al. ....... 514/210.01 |
| 2008/0249093 | A1 | 10/2008 | Colandrea et al. ......... 514/236.2 |
| 2008/0306124 | A1 | 12/2008 | Albert et al. ................... 514/364 |
| 2008/0318955 | A1 | 12/2008 | Bolli et al. ................. 514/236.2 |
| 2009/0036423 | A1 | 2/2009 | Pan et al. .................. 514/210.17 |
| 2009/0042954 | A1 | 2/2009 | Hale et al. ...................... 514/364 |
| 2009/0076070 | A1 | 3/2009 | Harada et al. ................. 514/303 |
| 2009/0131400 | A1 | 5/2009 | Mi et al. .................. 514/210.21 |
| 2009/0221547 | A1 | 9/2009 | Gao et al. ................. 514/210.18 |
| 2009/0253761 | A1 | 10/2009 | Lynch et al. ................... 514/364 |
| 2009/0275554 | A1 | 11/2009 | Habashita et al. ....... 514/210.18 |
| 2010/0113528 | A1 | 5/2010 | Ahmed et al. ................. 514/338 |
| 2010/0113796 | A1 | 5/2010 | Ahmed ......................... 548/131 |

FOREIGN PATENT DOCUMENTS

| EP | 1826186 | 2/2007 |
|---|---|---|
| EP | 1760071 | 3/2007 |
| EP | 1826197 | 8/2007 |
| EP | 2003132 A | 12/2008 |
| JP | 2007 262009 A | 10/2007 |
| WO | WO 2004/103279 A | 12/2004 |
| WO | WO 2004/113330 | 12/2004 |
| WO | WO 2005/032465 A | 4/2005 |
| WO | WO 2005/058848 | 6/2005 |
| WO | WO 2006/047195 | 5/2006 |
| WO | WO 2008/064337 | 5/2008 |
| WO | WO 2008/074821 | 6/2008 |
| WO | WO 2008/128951 | 10/2008 |
| WO | WO 2009/080724 | 7/2009 |
| WO | WO 2009/080725 | 7/2009 |
| WO | WO 2009/080728 | 7/2009 |
| WO | WO 2009/080729 | 7/2009 |
| WO | WO 2009/080730 | 7/2009 |

OTHER PUBLICATIONS

U.S. Appl. No. 12/747,191, filed Dec. 19, 2008, Heer, et al.
U.S. Appl. No. 12/747,188, filed Dec. 19, 2008, Heer, et al.
U.S. Appl. No. 12/360,886, filed Jan. 28, 2009, Heer, et al.
Allende, et al 2003 102:3665, Blood.
Brinkman, et al 2002 JBC 277:21453.
Brinkman, et al 2004 American J Transplantation, 4:1019.
Chiba, et al 1998, J Immunology 160:5037.
Chiba 2005 Pharmacology and Therapeutics 108:308.
Chun et al 2002 Pharmacological Reviews 54:265.
Forrest, et al 2004 J Pharmacol Exp Ther 309:758.
Fujino, et al 2003 J Pharmacol Exp Ther 305:70.
Graler and Goetzl 2004 FASEB J 18:551.
Hale, et al 2004 Bioorganic & Medicinal Chemistry Letters 14:3501.
Jo, et al 2005 Chem Biol 12:703.
Kluk and Hla 2002 Biochem et Biophysica Acta 1582:72.
Kahan, et al 2003, Transplanation 76:1079.
Kappos, et al 2006 New Eng J Medicine 355:1124.
Koyrakh, et al 2005 American J Transplantation 5:529.
Mandala, et al 2002 Science 296:346.
Matloubian, et al 2004 Nature 427:355.
Morris, et al 2005 EurJ Immunol 35:3570.
Nigel Cooke, et al: "Sphingosine 1-Phosphate Type 1 Receptor Modulators: Recent Advances and Therapeutic Potential" Annual Reports in Medicinal Chemistry, San Diego, US, vol. 42, Jan. 1, 2007, pp. 245-263, XP008102308; ISSN: 0065-7743.
Okamoto, et al 1998 J Biol Chem 273(42):27104.
Pyne and Pyne 2000, Biochem J. 349:385.

(Continued)

*Primary Examiner* — Zinna Northington Davis
(74) *Attorney, Agent, or Firm* — Linda E. Hall; John L. Lemanowicz

(57) ABSTRACT

The present invention relates to novel oxadiazole derivatives having pharmacological activity, processes for their preparation, pharmaceutical compositions containing them and their use in the treatment of various disorders.

4 Claims, No Drawings

OTHER PUBLICATIONS

Rausch, et al 2004 J Magn Reson Imaging 20:16.
Rosen and Goetzl 2005 Nat Rev Immunol, 5:560.
Sanchez and Hla 2004, J Cell Biochem 92:913.
Sanna, et al 2004 JBC 279:13839.
Singelton, et al 2005 FASEB J 19:1646.
Vachal Petr et al.: "Highly selective and potent agonists of sphingosine-1-phosphate 1 (S1P1) receptor." Bioorganic & Medicinal Chemistry Letters, Jul. 15, 2006, vol. 16, No. 14, Jul. 15, 2006 pp. 3684-3687 ISSN: 0960-894X.
Webb, et al 2004 J Neuroimmunol 153:108.
Wei, et al 2005, Nat. Immunology 6:1228.
Yan Lin, et al.: "SAR studies of 3-arylpropionic acids as potent and selective agonists of sphingosine-1-phosphate receptor-1 (S1P1) with enhanced pharmacokinetic properties." Bioorganic & Medicinal Chemistry Letters Feb. 1, 2007, vol. 17 No. 3. Feb. 1, 2007, pp. 828-831; ISSN: 0960-894X.

COMPOUNDS

This application is a 371 of International Application No. PCT/EP2009/055193, filed Apr. 29, 2009, which claims the priority of GB Application No. GB 0807910.5 filed Apr. 30, 2008, which are incorporated herein in their entirety.

The present invention relates to novel oxadiazole derivatives having pharmacological activity, processes for their preparation, pharmaceutical compositions containing them and their use in the treatment of various disorders.

Sphingosine 1-phosphate (S1P) is a bioactive lipid mediator formed by the phosphorylation of sphingosine by sphingosine kinases and is found in high levels in the blood. It is produced and secreted by a number of cell types, including those of hematopoietic origin such as platelets and mast cells (Okamoto et al 1998 J Biol Chem 273(42):27104; Sanchez and Hla 2004, J Cell Biochem 92:913). It has a wide range of biological actions, including regulation of cell proliferation, differentiation, motility, vascularisation, and activation of inflammatory cells and platelets (Pyne and Pyne 2000, Biochem J. 349: 385). Five subtypes of S1P responsive receptor have been described, S1P1 (Edg-1), S1P2 (Edg-5), S1P3 (Edg-3), S1P4 (Edg-6), and S1P5 (Edg-8), forming part of the G-protein coupled endothelial differentiation gene family of receptors (Chun et al 2002 Pharmacological Reviews 54:265, Sanchez and Hla 2004 J Cellular Biochemistry, 92:913). These 5 receptors show differential mRNA expression, with S1P1-3 being widely expressed, S1P4 expressed on lymphoid and hematopoietic tissues and S1P5 primarily in brain and to a lower degree in spleen. They signal via different subsets of G proteins to promote a variety of biological responses (Kluk and Hla 2002 Biochem et Biophysica Acta 1582:72, Sanchez and Hla 2004, J Cellular Biochem 92:913).

Proposed roles for the S1P1 receptor include lymphocyte trafficking, cytokine induction/suppression and effects on endothelial cells (Rosen and Goetzl 2005 Nat Rev Immunol. 5:560). Agonists of the S1P1 receptor have been used in a number of autoimmune and transplantation animal models, including Experimental Autoimmune Encephalomelitis (EAE) models of MS, to reduce the severity of the induced disease (Brinkman et al 2003 JBC 277:21453; Fujino et al 2003 J Pharmacol Exp Ther 305:70; Webb et al 2004 J Neuroimmunol 153:108; Rausch et al 2004 J Magn Reson Imaging 20:16). This activity is reported to be mediated by the effect of S1P agonists on lymphocyte circulation through the lymph system. Treatment with S1P agonists results in the sequestration of lymphocytes within secondary lymphoid organs such as the lymph nodes, inducing a reversible peripheral lymphopoenia in animal models (Chiba et al 1998, J Immunology 160:5037, Forrest et al 2004 J Pharmacol Exp Ther 309:758; Sanna et al 2004 JBC 279:13839). Published data on agonists suggests that compound treatment induces loss of the S1P1 receptor from the cell surface via internalisation (Graler and Goetzl 2004 FASEB J 18:551; Matloubian et al 2004 Nature 427:355; Jo et al 2005 Chem Biol 12:703) and it is this reduction of S1P1 receptor on immune cells which contributes to the reduction of movement of T cells from the lymph nodes back into the blood stream.

S1P1 gene deletion causes embryonic lethality. Experiments to examine the role of the S1P1 receptor in lymphocyte migration and trafficking have included the adoptive transfer of labelled S1P1 deficient T cells into irradiated wild type mice. These cells showed a reduced egress from secondary lymphoid organs (Matloubian et al 2004 Nature 427:355).

S1P1 has also been ascribed a role in endothelial cell junction modulation (Allende et al 2003 102:3665, Blood Singelton et al 2005 FASEB J 19:1646). With respect to this endothelial action, S1P1 agonists have been reported to have an effect on isolated lymph nodes which may be contributing to a role in modulating immune disorders. S1P1 agonists caused a closing of the endothelial stromal 'gates' of lymphatic sinuses which drain the lymph nodes and prevent lymphocyte egress (Wei wt al 2005, Nat. Immunology 6:1228).

The immunosuppressive compound FTY720 (JP11080026-A) has been shown to reduce circulating lymphocytes in animals and man, have disease modulating activity in animal models of immune disorders and reduce remission rates in relapsing remitting Multiple Sclerosis (Brinkman et al 2002 JBC 277:21453, Mandala et al 2002 Science 296:346, Fujino et al 2003 J Pharmacology and Experimental Therapeutics 305:45658, Brinkman et al 2004 American J Transplantation 4:1019, Webb et al 2004 J Neuroimmunology 153:108, Morris et al 2005 EurJ Immunol 35:3570, Chiba 2005 Pharmacology and Therapeutics 108: 308, Kahan et al 2003, Transplantation 76:1079, Kappos et al 2006 New Eng J Medicine 335:1124). This compound is a prodrug that is phosphorylated in vivo by sphingosine kinases to give a molecule that has agonist activity at the S1P1, S1P3, S1P4 and S1P5 receptors. Clinical studies have demonstrated that treatment with FTY720 results in bradycardia in the first 24 hours of treatment (Kappos et al 2006 New Eng J Medicine 335:1124). The bradycardia is thought to be due to agonism at the S1P3 receptor, based on a number of cell based and animal experiments. These include the use of S1P3 knock-out animals which, unlike wild type mice, do not demonstrate bradycardia following FTY720 administration, and the use of S1P1 selective compounds. (Hale et al 2004 Bioorganic & Medicinal Chemistry Letters 14:3501, Sanna et al 2004 JBC 279: 13839, Koyrakh et al 2005 American J Transplantation 5:529)

The following patent applications describe oxadiazole derivatives as S1P1 agonists: WO03/105771, WO05/058848, WO06/047195, WO06/100633, WO06/115188 and WO06/131336, WO07/024922 and WO07/116866.

The following patent applications describe tetrahydroisoquinolinyl-oxadiazole derivatives as S1P receptor agonists: WO06/064757, WO06/001463, WO04/113330.

The following patent application describes indole-oxadiazole derivatives as antipicornaviral agents: WO96/009822. The following patent applications describe indole-carboxylic acid derivatives as leukotriene receptor antagonists, pesticides and agrochemical fungicides respectively: WO06/090817, EP 0 439 785 and DE 39 39 238.

International patent application WO06/001463 discloses various compounds as agonists of the S1P1 receptor. International patent application PCT/EP2007/064185 discloses indole-oxadiazole compounds as agonists of the S1P1 receptor.

International patent application WO07/093,827 discloses substituted trifluoroethanone compounds as histone deacetylase inhibitors. International patent application WO05/040157 discloses melanin-concentrating hormone modulators.

A structurally novel class of compounds has now been found which provides agonists of the S1P1 receptor.

The present invention therefore provides compounds of formula (I) or a salt thereof:

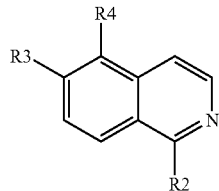
(I)

wherein
one of $R_3$ and $R_4$ is hydrogen and the other is (a)

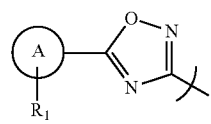
(a)

A is a phenyl or a 6-membered heteroaryl ring;

$R_1$ is hydrogen or up to two substituents independently selected from halogen, $C_{(1-4)}$alkyl, $C_{(1-4)}$alkoxy, trifluoromethoxy, difluoromethoxy, (2,2,2-trifluoroethyl)oxy, cyclopropyloxy, (cyclopropylmethyl)oxy, 3-oxetanyloxy, trifluoromethyl, cyano and pyrollidinyl substituted by fluorine;

$R_2$ is hydrogen, —($C_{1-5}$alkyl)COOH, or —NH($C_{1-5}$alkyl)COOH, —($C_{1-5}$alkyl)OH, —($C_{1-4}$) alkyl)CONR$_5$R$_6$, —($C_{1-2}$alkyl)NR$_5$R$_6$, —($C_{1-4}$alkyl)NR$_8$COR$_9$, —($C_{1-4}$alkyl)NR$_{10}$SO$_2$R$_{11}$, —(CH$_2$)$_2$SO$_2$Me, —NR$_5$R$_6$ or any one of groups (i) to (xii):

(i)

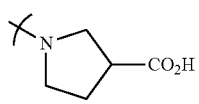
(ii)

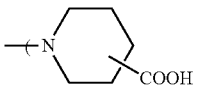
(iii)

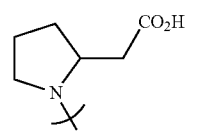
(iv)

(v)

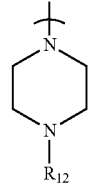
(vi)

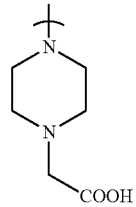
(vii)

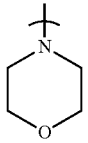
(viii)

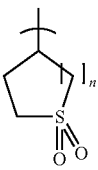
(ix)

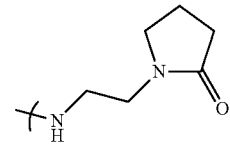
(x)

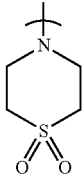
(xi)

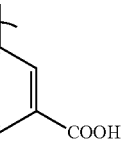

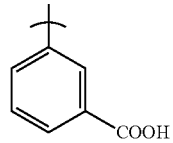
(xii)

$R_{5-8}$, $R_{10}$ and $R_{12}$ are each independently selected from hydrogen and $C_{1-3}$alkyl;

$R_9$ and $R_{11}$ are each independently selected from $C_{1-3}$alkyl; and n is 1 or 2.

The present invention therefore provides compounds of formula (IA) or a salt thereof:

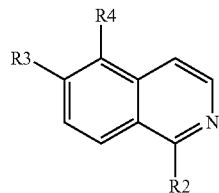
(IA)

wherein
one of R₃ and R₄ is hydrogen and the other is (a)

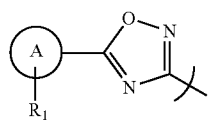
(a)

A is a phenyl or a 5 or 6-membered heteroaryl ring;

$R_1$ is hydrogen or up to two substituents independently selected from halogen, $C_{(1-4)}$alkyl, $C_{(1-4)}$alkoxy, trifluoromethoxy, difluoromethoxy, (2,2,2-trifluoroethyl)oxy, cyclopropyloxy, (cyclopropylmethyl)oxy, 3-oxetanyloxy, trifluoromethyl and cyano;

$R_2$ is hydrogen, —($C_{1-5}$alkyl)COOH, or —NH($C_{1-5}$alkyl)COOH, —($C_{1-5}$alkyl)OH, —($C_{1-4}$alkyl)CONR₅R₆, —($C_{1-2}$alkyl)NR₅R₆, —($C_{1-4}$alkyl)NR₈COR₉, —($C_{1-4}$alkyl)NR₁₀SO₂R₁₁, —(CH₂)₂SO₂Me, —NR₅R₆ or any one of groups (i) to (xi):

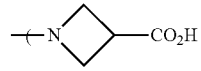
(i)

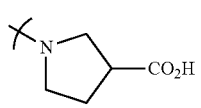
(ii)

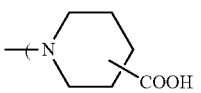
(iii)

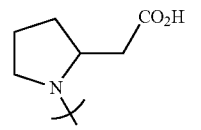
(iv)

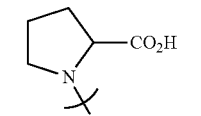
(v)

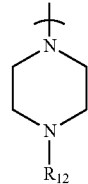
(vi)

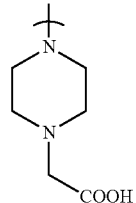
(vii)

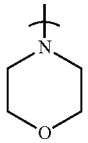
(viii)

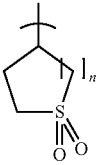
(ix)

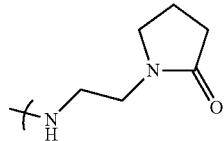
(x)

(xi)

$R_{5-8}$, $R_{10}$ and $R_{12}$ are each independently selected from hydrogen and $C_{1-3}$alkyl;
$R_9$ and $R_{11}$ are each independently selected from $C_{1-3}$alkyl; and
n is 1 or 2.

The term "alkyl" as a group or part of a group e.g. alkoxy or hydroxyalkyl refers to a straight or branched alkyl group in all isomeric forms. The term "$C_{(1-5)}$ alkyl" refers to an alkyl group, as defined above, containing at least 1, and at most 5 carbon atoms Examples of such alkyl groups include methyl, ethyl, propyl, n-propyl, iso-propyl, n-butyl, iso-butyl, sec-butyl, tert-butyl, n-pentyl, 1methylbutyl or 1,1dimethylpropyl. Examples of such alkoxy groups include methoxy, ethoxy, propoxy, iso-propoxy, butoxy, iso-butoxy, sec-butoxy, tert-butoxy, pentyloxy, (1-ethylpropyl)oxy, (1-methylbutyl)oxy, (2-methylbutyl)oxy, 3-methylbutyl)oxy, (1,1-dimethylpropyl)oxy, (2,2-dimethylpropyl)oxy.

As used herein, the term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "heteroaryl" represents an unsaturated ring which comprises one or more heteroatoms selected from O, N or S. Examples of such 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

One embodiment of the invention is a compound of formula (I) wherein
$R_3$ is hydrogen and $R_4$ is (a); and
A is phenyl or pyridyl; and
$R_1$ is up to two substituents independently selected from halogen, $C_{(1-4)}$alkoxy, trifluoromethoxy, difluoromethoxy, (cyclopropylmethyl)oxy, cyano and pyrollidinyl substituted by fluoro;
$R_2$ is hydrogen, —$(C_{2-3}$alkyl)COOH, —NH($C_2$alkyl)COOH, —$(C_3$alkyl)OH, group (i), group (ii), group (iii), group (v), group (vi) or group (xii); and
$R_{12}$ is hydrogen.

In one embodiment of the invention $R_3$ is hydrogen and $R_4$ is (a).

In one embodiment of the invention A is phenyl or pyridyl. In another embodiment of the invention A is phenyl.

In one embodiment of the invention $R_1$ is up to two substituents independently selected from halogen, $C_{(1-4)}$alkoxy, trifluoromethoxy, difluoromethoxy, propenyloxy, (cyclopropylmethyl)oxy, cyano and pyrollidinyl substituted by fluorine. In another embodiment of the invention $R_1$ is chloro and isopropoxy. In a further embodiment $R_1$ is chloro at the 3-position and isopropoxy at the 4-position when A is phenyl or $R_1$ is chloro at the 5-position and isopropoxy at the 6-position when A is pyridyl. In another embodiment $R_1$ is isopropoxy and cyano. In a further embodiment $R_1$ is cyano at the 3-position and isopropoxy at the 4-position when A is phenyl or $R_1$ is chloro at the 5-position and isopropoxy at the 6-position when A is pyridyl.

In one embodiment of the invention $R_2$ is hydrogen, —$(C_{2-3}$ alkyl)COOH, —NH($C_2$alkyl)COOH, —$(C_3$alkyl)OH, group (i), group (ii), group (iii), group (v), group (vi) or group (xii).

In one embodiment of the invention $R_{12}$ is hydrogen.

One embodiment of the invention is a compound of formula (IA) wherein
$R_3$ is hydrogen and $R_4$ is (a); and
A is phenyl; and
$R_1$ is up to two substituents independently selected from halogen and $C_{(1-4)}$alkoxy;
$R_2$ is hydrogen, —$(C_{1-5}$alkyl)COOH, —NH($C_{1-5}$alkyl)COOH, —$(C_{1-5}$alkyl)OH, group (iii) or group (vi); and
$R_{12}$ is hydrogen.

Another embodiment of the invention is a compound of formula (IA) wherein
$R_3$ is hydrogen and $R_4$ is (a); and
A is phenyl; and
$R_1$ is up to two substituents independently selected from chloro and isopropoxy;
$R_2$ is hydrogen, —$(CH_2)_2$COOH, —NH($CH_2)_2$COOH, ($CH_2)_3$OH, 4-carboxylic acid piperidin-1-yl or group (vi); and
$R_{12}$ is hydrogen.

The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Suitable compounds of the invention are:
3-[5-(5-{3-chloro-4-[(1-methylethyl)oxy]phenyl}-1,2,4-oxadiazol-3-yl)-1-isoquinolinyl]propanoic acid
N-[5-(5-{3-chloro-4-[(1-methylethyl)oxy]phenyl}-1,2,4-oxadiazol-3-yl)-1-isoquinolinyl]-β-alanine
3-[5-(5-{3-Chloro-4-[(1-methylethyl)oxy]phenyl}-1,2,4-oxadiazol-3-yl)-1-isoquinolinyl]-1-propanol
5-(5-{3-chloro-4-[(1-methylethyl)oxy]phenyl}-1,2,4-oxadiazol-3-yl)isoquinoline
1-[5-(5-{3-chloro-4-[(1-methylethyl)oxy]phenyl}-1,2,4-oxadiazol-3-yl)-1-isoquinolinyl]-4-piperidinecarboxylic acid
5-(5-{3-chloro-4-[(1-methylethyl)oxy]phenyl}-1,2,4-oxadiazol-3-yl)-1-(1-piperazinyl)isoquinoline
1-[5-(5-{3-Chloro-4-[(1-methylethyl)oxy]phenyl}-1,2,4-oxadiazol-3-yl)-1-isoquinolinyl]-3-azetidinecarboxylic acid ammonium salt
N-[5-(5-{3-Chloro-4-[(1-methylethyl)oxy]phenyl}-1,2,4-oxadiazol-3-yl)-1-isoquinolinyl]-L-alanine
1-[5-(5-{3-Chloro-4-[(1-methylethyl)oxy]phenyl}-1,2,4-oxadiazol-3-yl)-1-isoquinolinyl]proline
1-[5-(5-{3-Chloro-4-[(1-methylethyl)oxy]phenyl}-1,2,4-oxadiazol-3-yl)-1-isoquinolinyl]-3-pyrrolidinecarboxylic acid
N-[5-(5-{3-Chloro-4-[(1-methylethyl)oxy]phenyl}-1,2,4-oxadiazol-3-yl)-1-isoquinolinyl]-L-valine
5-{5-[4-[(1-methylethyl)oxy]-3-(methyloxy)phenyl]-1,2,4-oxadiazol-3-yl}isoquinoline
5-(5-{4-[(1,1-dimethylethyl)oxy]phenyl}-1,2,4-oxadiazol-3-yl)isoquinoline
5-{5-[4-(ethyloxy)-3,5-difluorophenyl]-1,2,4-oxadiazol-3-yl}isoquinoline
5-(5-{4-[(1-methylpropyl)oxy]phenyl}-1,2,4-oxadiazol-3-yl)isoquinoline
5-{5-[3,5-dichloro-4-(propyloxy)phenyl]-1,2,4-oxadiazol-3-yl}isoquinoline
4-[3-(5-Isoquinolinyl)-1,2,4-oxadiazol-5-yl]-1-(2-methylpropyl)-2(1H)-pyridinone
5-(5-{6-[(2,2,2-Trifluoroethyl)oxy]-3-pyridinyl}-1,2,4-oxadiazol-3-yl)isoquinoline
5-(5-{4-[(Trifluoromethyl)oxy]phenyl}-1,2,4-oxadiazol-3-yl)isoquinoline
5-(5-{4-[(Difluoromethyl)oxy]phenyl}-1,2,4-oxadiazol-3-yl)isoquinoline
5-(5-{2-Chloro-4-[(1-methylethyl)oxy]phenyl}-1,2,4-oxadiazol-3-yl)isoquinoline
3-[5-(5-{3-chloro-4-[(cyclopropylmethyl)oxy]phenyl}-1,2,4-oxadiazol-3-yl)-1-isoquinolinyl]propanoic acid
3-[5-(5-{3-Chloro-4-[(difluoromethyl)oxy]phenyl}-1,2,4-oxadiazol-3-yl)-1-isoquinolinyl]propanoic acid
3-[5-(5-{3-Chloro-4-[(2,2,2-trifluoroethyl)oxy]phenyl}-1,2,4-oxadiazol-3-yl)-1-isoquinolinyl]propanoic acid hydrochloride
3-[5-(5-{3-Cyano-4-[(cyclopropylmethyl)oxy]phenyl}-1,2,4-oxadiazol-3-yl)-1-isoquinolinyl]propanoic acid
3-[5-(5-{3-Cyano-4-[(1-methylethyl)oxy]phenyl}-1,2,4-oxadiazol-3-yl)-1-isoquinolinyl]propanoic acid hydrochloride 3-[5-(5-{5-Chloro-6-[(1-methylethyl)oxy]-3-pyridinyl}-1,2,
4-oxadiazol-3-yl)-1-isoquinolinyl]propanoic acid
3-[5-(5-{3-Cyano-4-[(2,2,2-trifluoroethyl)oxy]phenyl}-1,2,
4-oxadiazol-3-yl)-1-isoquinolinyl]propanoic acid
3-(5-{5-[3-Cyano-4-(3-fluoro-1-pyrrolidinyl)phenyl]-1,2,4-
oxadiazol-3-yl}-1-isoquinolinyl)propanoic acid
4-[5-(5-{5-Chloro-6-[(1-methylethyl)oxy]-3-pyridinyl}-1,2,
4-oxadiazol-3-yl)-1-isoquinolinyl]butanoic acid
4-[5-(5-{3-chloro-4-[(1-methylethyl)oxy]phenyl}-1,2,4-
oxadiazol-3-yl)-1-isoquinolinyl]butanoic acid
3-[5-(5-{3-Chloro-4-[(1-methylethyl)oxy]phenyl}-1,2,4-
oxadiazol-3-yl)-1-isoquinolinyl]benzoic acid
or salts thereof.

Pharmaceutically acceptable derivatives of compounds of formula (I) include any pharmaceutically acceptable salt, ester or salt of such ester of a compound of formula (I) which, upon administration to the recipient is capable of providing (directly or indirectly) a compound of formula (I) or an active metabolite or residue thereof.

Certain esters of compounds of formula (I) are described herein as intermediates in the synthesis of some of the described Examples. Such esters may also exhibit activity as S1P1 agonists and as such form part of the invention.

The compounds of formula (I) can form salts. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. Salts may also be prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tris(hydroxymethyl)aminomethane (TRIS, trometamol) and the like. Salts may also be formed from basic ion exchange resins, for example polyamine resins. When the compound of the present invention is basic, salts may be prepared from pharmaceutically acceptable acids, including inorganic and organic acids. Such acids include acetic, benzenesulfonic, benzoic, camphorsulfonic, citric, ethanesulfonic, ethanedisulfonic, fumaric, gluconic, glutamic, hydrobromic, hydrochloric, isethionic, lactic, maleic, malic, mandelic, methanesulfonic, mucic, pamoic, pantothenic, phosphoric, propionic, succinic, sulfuric, tartaric, p-toluenesulfonic acid, and the like.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

In a further aspect, this invention provides processes for the preparation of a compound of formula (I). It will be appreciated by the person skilled in the art that Schemes 1 to 6 are also applicable to the production of compounds of formula (I) wherein $R_3$ is (a) (rather than $R_4$ is (a) as depicted) by using the appropriate intermediates. Compounds of formula (VIII) and (XVI) are known in the literature and are commercially available for isomers where either $R_3$ is (a) or $R_4$ is (a). Compounds of formula (VII), (X), and (XIV) are either commercially available, known in the literature, or may be made by conventional means.

Scheme 1

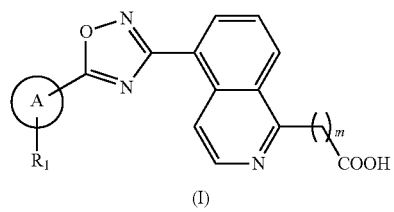

(I)

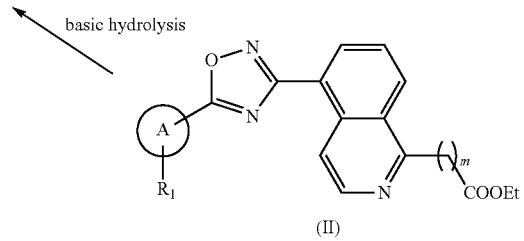

(II)

basic hydrolysis

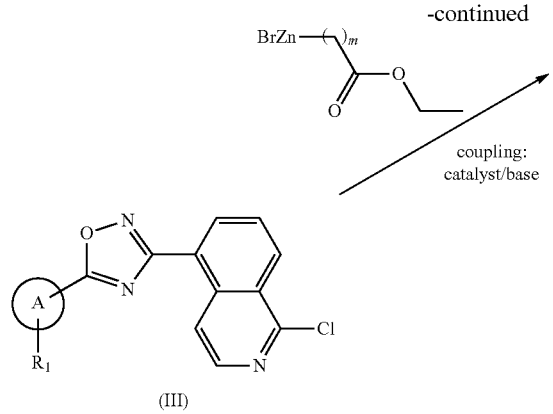
(III)
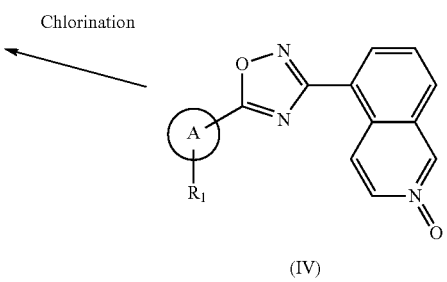
(IV)
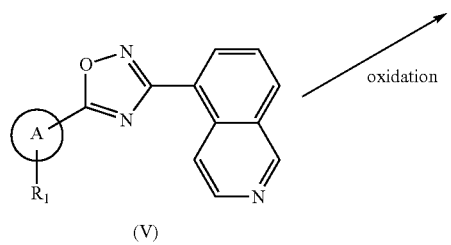
(V)
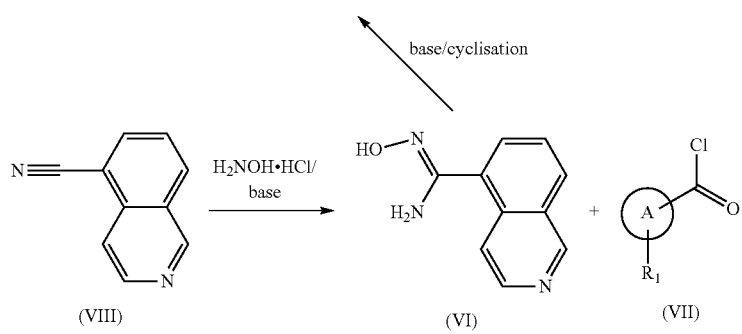
(VIII)   (VI)   (VII)
m = 1-5

Scheme 2
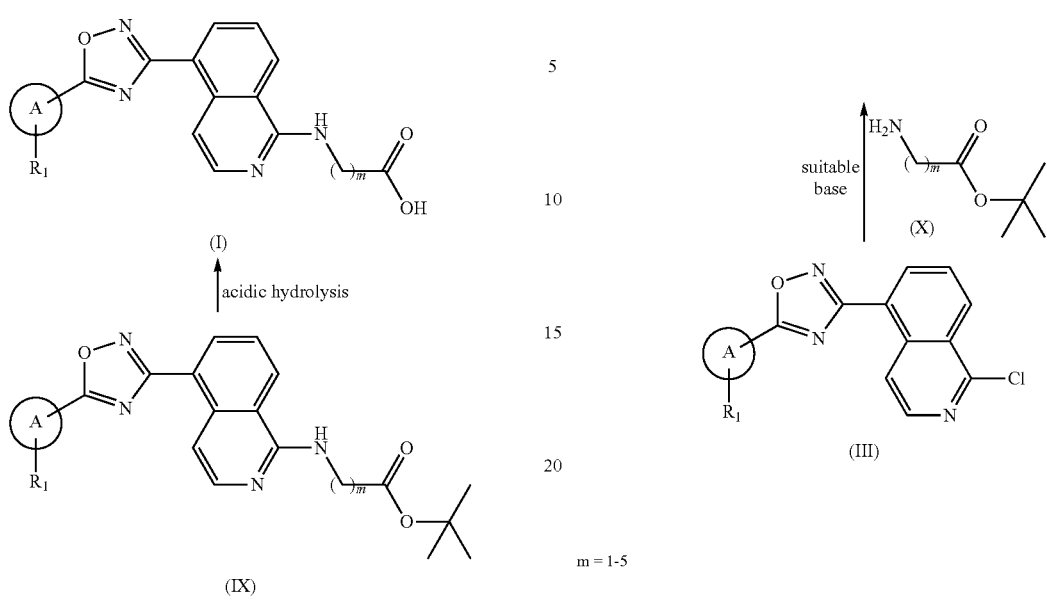
m = 1-5
Scheme 3
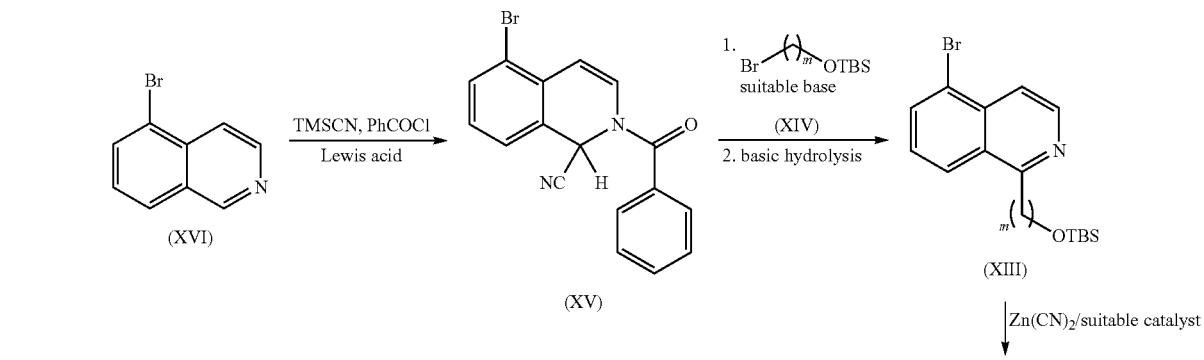
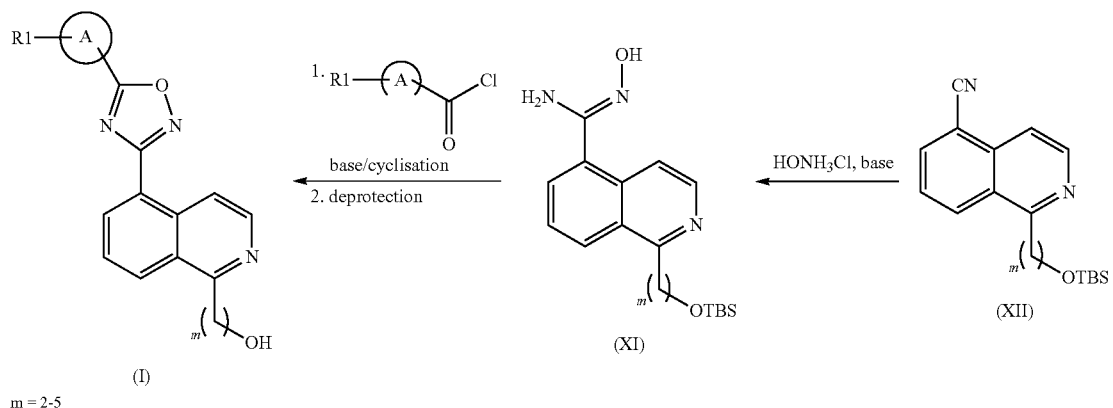
m = 2-5

Certain compounds of formula (I) may alternatively be prepared using the route outlined in scheme 4. Compound (XVII) may be converted into compound (XXII) by treatment with hydroxylamine hydrochloride and an appropriate base, such as sodium bicarbonate, in a solvent such as methanol or ethanol at an elevated temperature such as at reflux. Compound (XXII) may be converted into compounds of formula (XXIII) by treatment with a suitable carboxylic acid chloride or by treatment with a suitable carboxylic acid in the presence of a suitable amide coupling agent such as 1-(3-dimethylaminopropyl)-3-ethylcarbodiimide hydrochloride (EDAC) 1-hydroxybenzotriazole (HOBt) in a suitable solvent such as DMF. Compounds of formula (XXIII) may be converted to compounds of formula (XXIV) by bromination for example using phosphorus oxybromide. Compounds of formula (XXIV) may be converted to compounds of formula (XXI) by reaction with an appropriate zinc bromide reagent such as bromo[3-(ethyloxy)-3-oxopropyl]zinc in the presence of a suitable catalyst such as 1,1'-bis(diphenylphosphino)ferrocene-palladium(II)dichloride in the presence of a suitable base such as potassium carbonate. Compounds of formula (XXI) may be converted to certain compounds of formula by treatment with a base such as aqueous sodium hydroxide in an alcoholic solvent such as methanol or ethanol when for example R=ethyl or by reaction with a suitable acid such as trifluoroacetic acid when R=BOC Alternatively compounds of formula (XXI) can be prepared by converting compound (XVII) to compound (XVIII) by bromination for example using phosphorus oxybromide. Compound (XVIII) can then be converted to compounds of formula (XIX) by reaction with an appropriate zinc bromide reagent such as bromo[3-(ethyloxy)-3-oxopropyl]zinc in the presence of a suitable catalyst such as 1,1'-bis(diphenylphosphino)ferrocene-palladium(II) dichloride in the presence of a suitable base such as potassium carbonate. Compounds of formula (XIX) can be converted to compounds of formula (XX) by treatment with hydroxylamine hydrochloride and an appropriate base, such as sodium bicarbonate, in a solvent such as methanol or ethanol at an elevated temperature such as at reflux. Compound (XX) may be converted into compounds of formula (XXI) by treatment with a suitable carboxylic acid chloride or by treatment with a suitable carboxylic acid in the presence of a suitable amide coupling agent such as 1-(3-dimethylaminopropyl)-3-ethylcarbodiimide hydrochloride (EDAC) 1-hydroxybenzotriazole (HOBt) in a suitable solvent such as DMF.

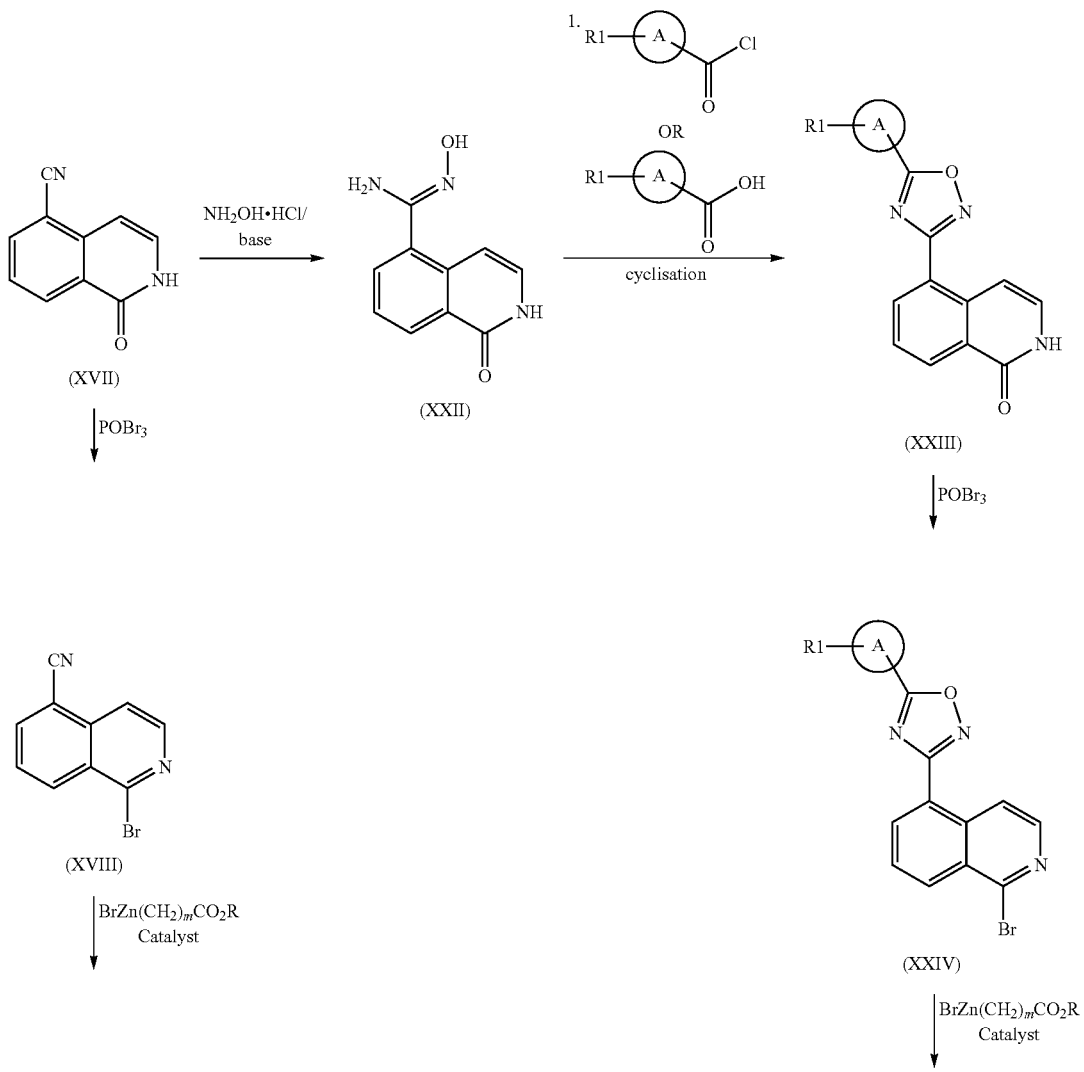

Scheme 4

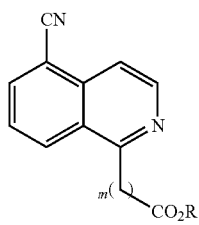

(XIX)

↓ NH₂OH·HCl/base

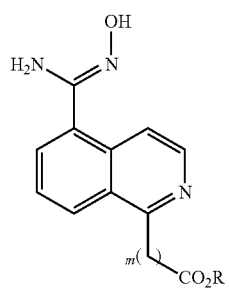

(XX)

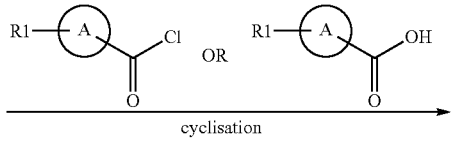

cyclisation ⟶

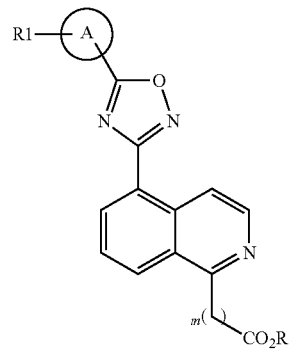

(XXI)

↓ Acid or base

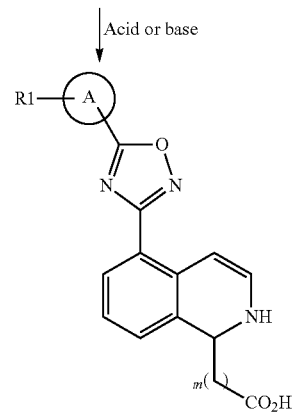

m = 1-5

Certain compounds of formula (I) may alternatively be prepared using the route outlined in scheme 5 where Z=CO₂H or OH. Compound (XVI) may be converted into compound (XV) by treatment with trimethylsilylcyanide and benzoyl chloride in the presence of aluminium chloride in a suitable solvent such as dichloromethane. Compound (XV) can be converted to compounds of formula (XXV) by reaction with an appropriate protected alkoxy halide such as commercially available bromopropoxy)-tert-butyldimethylsilane or an appropriate haloester such as 1,1-dimethylethyl 3-bromopropanoate in the presence of a suitable base such as sodium hydride in an appropriate solvent such as DMF. Compounds of formula (XXV) may be converted into compounds of formula (XXVI) by treatment with a suitable cyanide source such as zinc cyanide in the presence of a catalyst such as tetrakistriphenylphosphine palladium (0) in a suitable solvent such as dimethylformamide (DMF) at an elevated temperature such as 120° C. Compounds of formula (XXVI) may be converted into compounds of formula (XXVII) by treatment with hydroxylamine hydrochloride and an appropriate base, such as sodium bicarbonate, in a solvent such as methanol or ethanol at an elevated temperature such as 65° C. Compounds of formula (XXVII) may be converted into compounds of formula (XXVIII) by treatment with a suitable carboxylic acid chloride in the presence of a base such as triethylamine in a suitable solvent such as 1,4-dioxane. Such reactions are typically stirred for a period of time at room temperature, then at elevated temperatures, such as 145° C. Acid chlorides are either commercially available or may be prepared from the corresponding acid by conventional means. Alternatively compounds of formula (XXVII) may be converted into compounds of formula (XVIII) by treatment with a carboxylic acid in the presence of a suitable amide coupling agent such as 1-(3-dimethylaminopropyl)-3-ethyl-carbodiimide hydrochloride (EDAC) 1-hydroxybenzotriazole (HOBt) in a suitable solvent such as DMF. Such reactions are typically carried out at elevated temperature, such as 50-80° C. Typically, the acid, EDAC and HOBt are stirred for a period of time at room temperature prior to addition of the compound of formula (XXVII). Typically, compounds of formula (XVIII) whereby Y=OTBDMS may then be deprotected by treatment with an appropriate reagent such as lithium chloride to give certain compounds of formula (I) where Z=OH. Compounds whereby Y=CO$_2$R and for example R=tBu may be converted to certain compounds of formula (I) where Z=CO$_2$H by treatment with an appropriate acid such as trifluoroacetic acid.

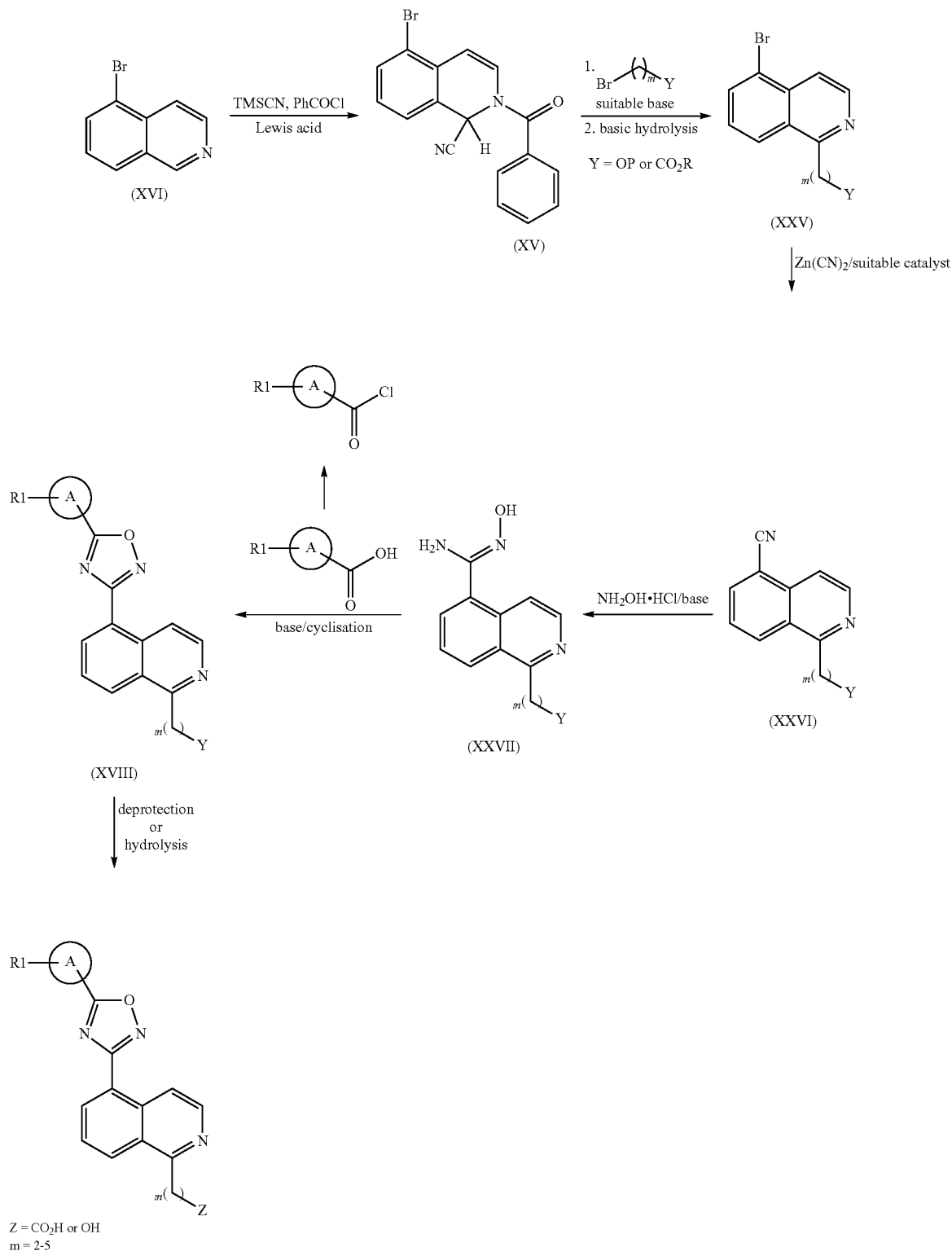

In a further aspect, this invention provides processes for the preparation of certain compounds (I) as shown in scheme 6.

Compounds of formula (III) may be converted into certain compounds of formula (I) by treatment with an appropriate amino acid in the presence of an appropriate base such as sodium hydride in a suitable solvent such as DMSO. Reaction of compounds of formula (III) with an appropriate amino ester in the presence of a suitable base such as DIPEA in a suitable solvent such as NMP at an elevated temperature such as 180° C. give compounds of formula (XIX) which can then be converted to certain compounds of formula (I) by reaction with a suitable acid such as trifluoroacetic acid when R=t-butyl or a suitable base such as sodium hydroxide when for example R=Ethyl Compounds of formula (I) and their pharmaceutically acceptable salts are therefore of use in the treatment of multiple sclerosis.

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the conditions or disorders mediated via the S1P1 receptor. In particular the invention provides a compound of formula (I) or a pharmaceutically acceptable salt thereof for use as a therapeutic substance in the treatment of rheumatoid arthritis, psoriatic arthritis, atherosclerosis, scleroderma, primary

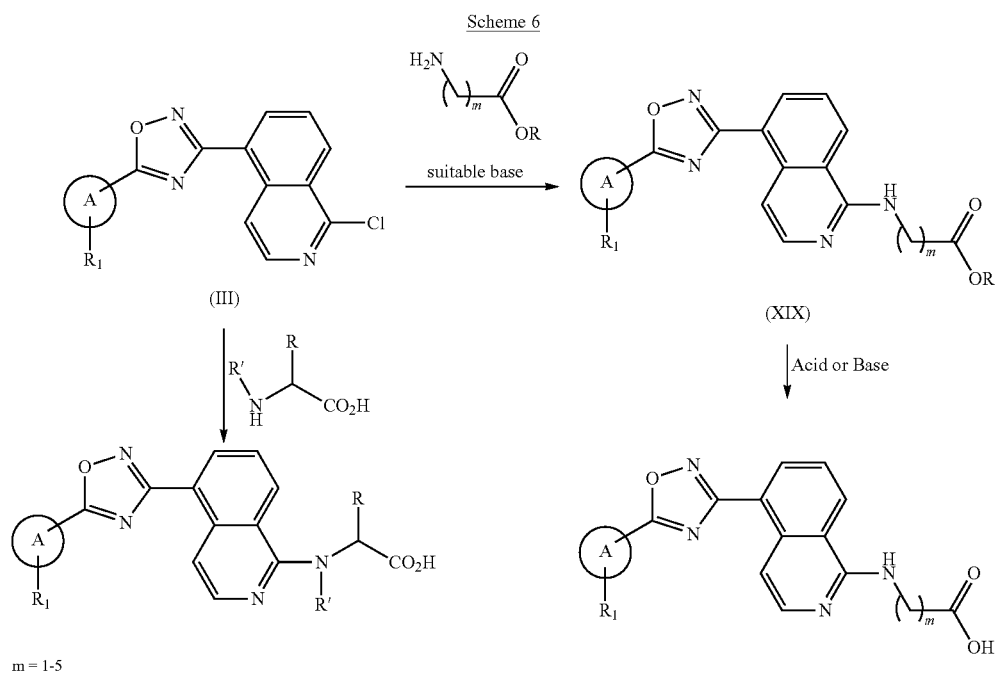

Scheme 6 m = 1-5

Compounds of formula (I) and their pharmaceutically acceptable salts are therefore of use in the treatment of conditions or disorders which are mediated via the S1P1 receptor. In particular the compounds of formula (I) and their pharmaceutically acceptable salts are of use in the treatment of rheumatoid arthritis, psoriatic arthritis, atherosclerosis, scleroderma, primary Sjogren's syndrome, allergic disorders, anaphylaxis, Still's Disease, Systemic Lupus Erythematosus, multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes (herein after referred to as the "Disorders of the Invention").

Compounds of formula (I) and their pharmaceutically acceptable salts are therefore of use in the treatment of lupus erythematosis.

Compounds of formula (I) and their pharmaceutically acceptable salts are therefore of use in the treatment of psoriasis.

Sjogren's syndrome, allergic disorders, anaphylaxis, Still's Disease, Systemic Lupus Erythematosus, multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes. The invention further provides a method of treatment of conditions or disorders in mammals including humans which can be mediated via the S1P1 receptor, which comprises administering to the sufferer a therapeutically safe and effective amount of a compound of formula (I) or a pharmaceutically acceptable salt thereof.

Compounds of formula (I) and their pharmaceutically acceptable salts are of use as therapeutic substances in the treatment of lupus erythematosis.

Compounds of formula (I) and their pharmaceutically acceptable salts are of use as therapeutic substances in the treatment of psoriasis.

Compounds of formula (I) and their pharmaceutically acceptable salts are of use as therapeutic substances in the treatment of multiple sclerosis.

The invention further provides a method of treatment of conditions or disorders in mammals including humans which can be mediated via the S1P1 receptor, which comprises administering to the sufferer a therapeutically safe and effective amount of a compound of formula (I) or a pharmaceutically acceptable salt thereof. In particular the invention provides a method of treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes, which comprises administering to the sufferer a therapeutically safe and effective amount of a compound of formula (I) or a pharmaceutically acceptable salt thereof.

The invention provides a method of treatment of lupus erythematosis, which comprises administering to the sufferer a therapeutically safe and effective amount of a compound of formula (I) or a pharmaceutically acceptable salt thereof.

The invention provides a method of treatment of psoriasis, which comprises administering to the sufferer a therapeutically safe and effective amount of a compound of formula (I) or a pharmaceutically acceptable salt thereof.

The invention provides a method of treatment of multiple sclerosis, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the conditions or disorders mediated via the S1P1 receptor.

In another aspect, the invention provides for the use of a compound of formula (I) or a pharmaceutically acceptable salt thereof in the manufacture of a medicament for use in the treatment of the conditions or disorders mediated via the S1P1 receptor Compounds of formula (I) and their pharmaceutically acceptable salts are of use in the manufacture of a medicament for use in the treatment of lupus erythematosis.

Compounds of formula (I) and their pharmaceutically acceptable salts are of use in the manufacture of a medicament for use in the treatment of psoriasis.

Compounds of formula (I) and their pharmaceutically acceptable salts are of use in the manufacture of a medicament for use in the treatment of multiple sclerosis.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

The potencies and efficacies of the compounds of this invention for the S1P1 receptor can be determined by GTPγS assay performed on the human cloned receptor as described herein Compounds of formula (I) have demonstrated agonist activity at the S1P1 receptor, using the functional assays described herein.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of formula (I) or pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, 1.0 to 500 mg or 1.0 to 200 mg and such unit doses may be administered more than once a day, for example two or three times a day.

The compounds of formula (I) or pharmaceutically acceptable salts thereof may be used in combination preparations. For example, the compounds of the invention may be used in combination with cyclosporin A or other therapeutically active compounds.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I.

Compounds of formula (I) and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^8$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagent.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

ABBREVIATIONS h—hours
g—grams
mg—milligrams
ml—millilitres
ul—microlitres
CHCl$_3$-chloroform
MeCN—acetonitrile
MeOH—methanol
EtOH—ethanol
EtOAc—ethyl acetate
DCM—dichloromethane
DMF—N,N-dimethylformamide
DMSO—dimethylsulphoxide
DIPEA—diisopropylethylamine (Hunigs base)
NMP—N-Methyl-2-pyrrolidinone
THF—Tetrahydrofuran
HATU—{O-(7-azabenzotriazol-1-yl)-1,1,3,3-tetramethyluronium hexafluorophosphate}
PdCl$_2$(dppf)-1,1'-bis(diphenylphosphino)ferrocene-palladium(II)dichloride
dppf—1,1'-bis(diphenylphosphino)ferrocene
RT—room temperature
° C.—degrees Celsius
M—Molar
H—proton
br—broad
s—singlet
d—doublet
t—triplet
q—quartet
s—septet
m—multiplet
NMR—Nuclear magnetic resonance
HPLC—High performance liquid chromatography
MS—mass spectrometry
[MH$^+$]—mass ion+H$^+$
[M−H$^+$]—mass ion−H$^+$
MDAP—mass directed automated preparative liquid chromatography
SCX refers to a solid phase extraction (SPE) column with benzene sulfonic acid residues immobilised on the solid phase (eg. Biotage Isolute™ SCX-2 columns).

'Hydrophobic Frit' refers to a PTFE filter medium (frit), pore size 5.0 mm, housed in a polypropylene tube (e.g. Whatman)

General Chemistry

The intermediates for the preparation of the examples may not necessarily have been prepared from the specific batch described.

Description 1

N-Hydroxy-5-isoquinolinecarboximidamide (D1)

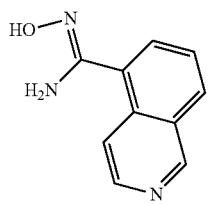

5-Isoquinolinecarbonitrile (2 g, 13 mmol; available from Fulcrum Scientific Product List), hydroxylamine.hydrochloride (7.21 g, 104 mmol) and sodium bicarbonate (10.9 g, 130 mmol), were added to a 0.5 L round bottomed flask containing ethanol (250 ml). The reaction mixture was heated at 65° C. for 3 hours and stirred for 12 hours. The cooled reaction mixture was evaporated to a smaller volume under reduced pressure and chromatographed over a 4×6 inch silica column eluting with ethanol to provide the title compound as a yellow solid (2.9 g).

MS: (+ve ion electrospray) m/z 188 [MH$^+$], $^1$H NMR (400 MHz, CD$_3$OD) δ (inter alia) 9.29 (1H, s), 8.49 (1H, d, J 6.0 Hz), 8.22 (1H, d, J 8.4 Hz), 8.19 (1H, d, J 6.0 Hz), 7.97-7.91 (1H, m), 7.79-7.73 (1H, m).

Description 2

Methyl 3-chloro-4-[(1-methylethyl)oxy]benzoate (D2)

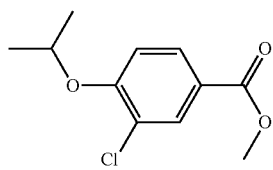

Methyl 3-chloro-4-hydroxybenzoate (50 g, 0.27 mole; available from Alfa Aesar), potassium carbonate (74 g, 0.54 mole) and 2-iodopropane (29.5 ml, 0.23 mole) were stirred at room temperature in DMF (100 ml). After 18 hours, the solvent was removed by evaporation under vacuum and the residue was chromatographed over a column of silica 60 eluting with ethyl acetate/hexane (1:1) to give the title compound as an oil (55 g). MS: m/z (API-ES) 229 [MH$^+$]; $^1$H NMR (400 MHz, CDCl$_3$) δ (inter alia) 8.05 (1H, d), 7.89 (1H, dd), 6.94 (1H, d), 4.60-4.72 (1H, m), 3.89 (3H, s), 1.41 (6H, d).

Description 3

3-Chloro-4-[(1-methylethyl)oxy]benzoic acid (D3)

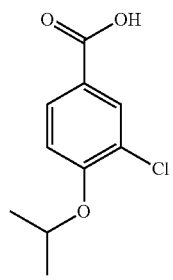

Methyl 3-chloro-4-[(1-methylethyl)oxy]benzoate (D2; 100 g) was taken up in a mixture of methanol (555 ml) and 2N NaOH solution (555 ml). An insoluble white suspension was observed but with time complete solubility was observed. The reaction was stirred at room temperature overnight and the excess methanol was removed by evaporation until water was coming over. The basic solution was acidified to pH 1-2 and a white solid was filtered off which was washed with water (500 ml) and dried in vacuo overnight to give the title compound (82 g).

MS: m/z 213, 215 [M–H]

Description 4

3-Chloro-4-[(1-methylethyl)oxy]benzoyl chloride (D4)

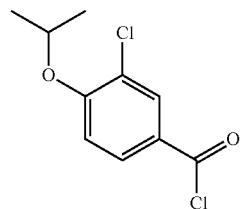

3-Chloro-4-[(1-methylethyl)oxy]benzoic acid (D3; 4 g, 18. mmol), dichloromethane (DCM) (30 ml), oxalyl chloride (1.88 ml, 21.4 mmol) and DMF (1.4 µl, 0.019 mmol) were stirred under a blanket of nitrogen for 18 h. The solvent was removed in vacuo to give a yellow oil which crystallised on standing. The solid was dissolved in DCM and the solvent was removed in vacuo to give the title compound as a yellow solid (4.2 g).

MS: m/z 270 [MH$^+$]

Description 6

5-(5-{3-Chloro-4-[1'-methylethyl)oxy]phenyl}-1,2,4-oxadiazol-3-yl)isoquinoline 2-oxide D6)

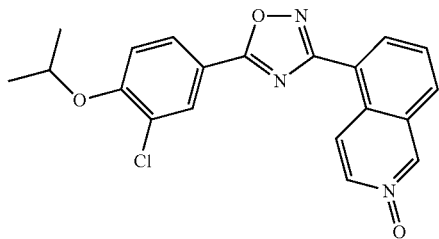

5-(5-{3-Chloro-4-[(1-methylethyl)oxy]phenyl}-1,2,4-oxadiazol-3-yl)isoquinoline (E6; 1.2 g, 3.28 mmol) was dissolved in dichloromethane (100 ml) and the solution was stirred with m-chloroperbenzoic acid (3.4 g, 19.7 mmol) at room temperature for 1.5 h. The reaction mixture was diluted with dichloromethane and washed with potassium carbonate solution and the organic layer was evaporated to dryness. Chloroform was added to the residue and insoluble material was filtered off; evaporation to dryness gave the title compound as a white solid (1.18 g).

MS: (+ve ion electrospray) m/z 382 [MH$^+$]; $^1$H NMR (400 MHz, CDCl$_3$) δ (inter alia) 9.02 (1H, d, J 7.6 Hz), 8.83 (1H, d, J 2 Hz), 8.51 (1H, dd, J 0.8 and 7.2 Hz), 8.26-8.29 (2H, m), 8.11 (1H, dd, J 2.0 Hz and 8.8 Hz), 7.88 (1H, d, J 4.4 Hz), 7.76 (1H, dd, J 7.6 Hz and 8.4 Hz), 7.09 (1H, d, J 8.8 Hz), 4.70-4.79 (1H, m), 1.47 (6H, d, J 6.0 Hz)

Description 7

1-Chloro-5-(5-{3-chloro-4-[(1-methylethyl)oxy]phenyl}-1,2,4-oxadiazol-3-yl)isoquinoline (D7)

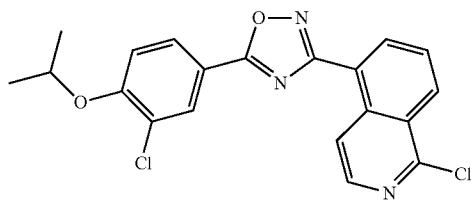

5-(5-{3-Chloro-4-[(1-methylethyl)oxy]phenyl}-1,2,4-oxadiazol-3-yl)isoquinoline 2-oxide (D6; 1.18 g, 3.09 mmol) and phosphorus oxychloride (5.76 ml, 61.8 mmol) was stirred under an atmosphere of argon at room temperature for 4 hours. The mixture was then heated to 65° C. for 15 minutes, the phosphorus oxychloride evaporated under reduced pressure, and the residue, azeotroped with toluene and dried under vacuum overnight. The pale yellow solid residue was dissolved in dichloromethane (50 ml) and stirred with 2M NaOH (10 ml). The organic layer was separated, dried with MgSO$_4$ and evaporated to dryness under reduced pressure to give a pale yellow solid (1.14 g) which was chromatographed over silica eluting with dichloromethane to give the title compound as a white solid (0.85 g).

MS: (−ve ion electrospray) m/z 400 [MH$^+$]; $^1$H NMR (400 MHz, CDCl$_3$) δ (inter alia) 8.87 (1H, dd, J 0.8 Hz and 6 Hz), 8.66 (1H, dd, J 1.2 and 7.2 Hz), 8.60 (1H, dd, J 1.2 and 8.8 Hz), 8.44 (1H, d, J 5.6 Hz), 8.29 (1H, d, J 2.4 Hz), 8.11 (1H, dd, J 2.4 Hz and 8.8 Hz), 7.84 (1H, dd, J 7.6 Hz and 8.4 Hz), 7.09 (1H, d, J 9.2 Hz), 4.77-4.70 (1H, m), 1.47 (6H, d, J 6 Hz).
A further 300 mg of the product containing an impurity was eluted from the column.

Description 8

Ethyl 3-[5-(5-{3-chloro-4-[(1-methylethyl)oxy]phenyl}-1,2,4-oxadiazol-3-yl)-1-isoquinolinyl]propanoate (D8)

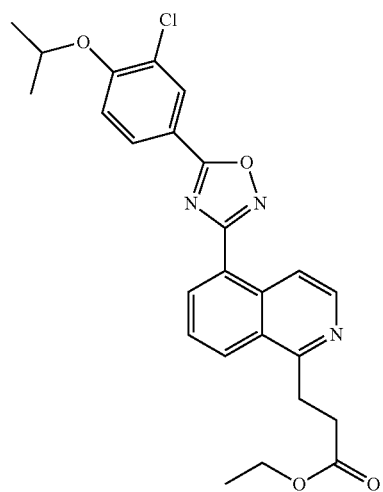

1-Chloro-5-(5-{3-chloro-4-[(1-methylethyl)oxy]phenyl}-1,2,4-oxadiazol-3-yl)isoquinoline (D7; 600 mg, 1.50 mmol), 1,1'-bis(diphenylphosphino)ferrocene-palladium(II) dichloride (122 mg, 0.150 mmol), and potassium carbonate (207 mg, 1.50 mmol), were split into 3 equal lots and each introduced to 3 separate microwave vials. Dry NMP (6 ml) was added to each vessel and the mixtures stirred vigorously for 5 minutes. After this time bromo[3-(ethyloxy)-3-oxopropyl]zinc in THF (6 ml, 3.00 mmol; available from Alfa Aesar) (2 ml to each vial) was added. The reaction vessels were sealed and heated under microwave irradiation to 120° C. for 60 min. After this time, a further aliquot of 1,1'-bis(diphenylphosphino)ferrocene-palladium(II) dichloride (122 mg, 0.150 mmol) (41 mg to each vial) was added. The reaction vessel was sealed and heated under microwave irradiation at 120° C. for 60 min.

The contents of the three vials were pooled with the reaction mixture from a previous preparation of D6 (using the same method and 100 mg of chloroquinoline starting material), and the mixture diluted with ethyl acetate and washed sequentially with brine (×2) and water (×2). The organic layers were concentrated in vacuo to give a red oil that was dissolved in dichloromethane, and purified by flash chromatography on silica gel, eluting with a dichloromethane/ethyl acetate (2% to 20% EtOAc) gradient. The relevant fractions were pooled and concentrated in vacuo to give a red solid that was triturated with diethyl ether. The resulting brick coloured solid was collected by filtration and dried in vacuo to give the title compound (80 mg, 8%).

MS: m/z 466, 468 [MH$^+$]

Description 9

1,1-Dimethylethyl N-[5-(5-{3-chloro-4-[(1-methylethyl)oxy]phenyl}-1,2,4-oxadiazol-3-yl)-1-isoquinolinyl]-β-alaninate (D9)

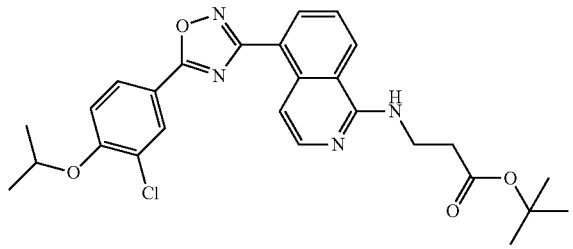

1-Chloro-5-(5-{3-chloro-4-[(1-methylethyl)oxy]phenyl}-1,2,4-oxadiazol-3-yl)isoquinoline (D7; 200 mg, 0.5 mmol), di-isopropylethylamine (0.873 ml, 1.0 mmol) and 1,1-dimethylethyl β-alaninate (726 mg, 5 mmol; available e.g. from Novabiochem) were placed into a 20 ml microwave vial, and N-methyl-2-pyrrolidinone (NMP, 8 ml) was added. The mixture was heated under microwave irradiation at 180° C. for one hour, diluted with methanol and chromatographed over an SCX cation exchange column (Biotage), which was washed with methanol and dichloromethane and eluted with methanolic ammonia. Washings and eluate from the SCX column were re-combined and evaporated in vacuo until only NMP remained. Water (20 ml) was added to the reaction mixture and a solid precipitate formed. The precipitate was collected by filtration and azeotroped twice with toluene. The solid was dissolved in dichloromethane (5 ml) and chromatographed on a silica column, eluting with dichloromethane to yield the title compound (38 mg) as a pale yellow solid.

MS: (+ve ion electrospray) m/z 508.9 [MH$^+$]; $^1$H NMR (400 MHz, CDCl$_3$) δ (inter alia) 8.43 (1H, dd, J 1.0 Hz and 6.4 Hz), 8.28 (1H, d, J 2.0 Hz), 8.10 (2H, m), 8.02 (1H, m), 7.97 (1H, d, J 8.4 Hz), 7.57 (1H, m), 7.08 (1H, d, J 9.2 Hz), 6.12 (1H, t, J 5.6 Hz), 4.73 (1H, m), 3.91 (2H, m), 2.68 (2H, m), 1.45-1.51 (15H, m).

Description 10

5-Bromo-2-(phenylcarbonyl)-1,2-dihydro-1-isoquinolinecarbonitrile (D10)

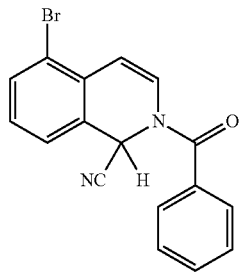

A round bottomed flask was charged with 5-bromoisoquinoline (available from Aldrich; 4 g, 19.2 mmol), dichloromethane (DCM) (50 ml), trimethylsilyl cyanide (4.81 ml, 38.5 mmol) and aluminium chloride (15 mg, 0.112 mmol). To the mixture was added benzoyl chloride (4.46 ml, 38.5 mmol) slowly over a period of 5 minutes. The mixture was warmed to 30° C. for 3 h after which time it was treated with water (50 ml) and stirred at room temperature for 30 minutes. The organic layers were collected and washed sequentially with 2N HCl, 2N NaOH and brine. The organic layers were passed through a hydrophobic frit before being concentrated in vacuo to give an orange solid. The solid was triturated with diethyl ether and the slurry filtered. The isolated solid was dried in vacuo to give the title compound as a grey solid (3.9 g).

$^1$H NMR (400 MHz, CHLOROFORM-d) δ ppm 7.55-7.67 (m, 4H), 7.49 (t, J=7.5 Hz, 2H), 7.31 (d, J=7.5 Hz, 1H), 7.20 (t, J=7.5 Hz, 1H), 6.73 (d, J=7.5 Hz, 1H), 6.55 (br. s., 1H), 6.42 (d, J=7.5 Hz, 1H)

Description 11

5-Bromo-1-(3-{[(1,1-dimethylethyl)(dimethyl)silyl]oxy}propyl)isoquinoline (D11)

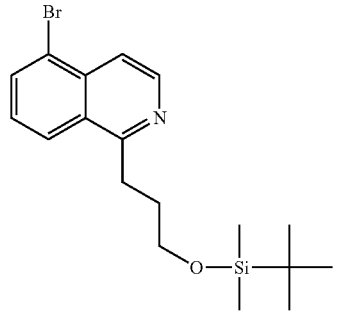

A dried round bottomed flask was charged with 5-bromo-2-(phenylcarbonyl)-1,2-dihydro-1-isoquinolinecarbonitrile (D10; 687 mg, 2.03 mmol) and dry, nitrogen purged N,N-dimethylformamide (DMF) (15 ml). The solution was cooled to −10° C. with stirring in an ice/methanol bath at which temperature the flask was evacuated. The flask was closed from the vacuum and allowed to warm to room temperature before the vacuum was re-introduced and the vessel then filled with nitrogen. (3-Bromopropoxy)-tert-butyldimethylsilane (available from Aldrich; 0.563 ml, 2.43 mmol) was added, the vessel purged with nitrogen three times and the solution cooled again to −10° C. To the solution was added sodium hydride (97 mg, 2.43 mmol) as a single portion. The mixture was held at −10° C. for 5 minutes before being allowed to warm to room temperature and stirred under nitrogen for 5 hours. To the mixture was added potassium carbonate (560 mg, 4.05 mmol). The slurry was warmed to 80° C. for 3 hours before being filtered through a plug of celite (ethyl acetate eluent). The organic layers were further diluted with ethyl acetate and partitioned with water (×3) then brine. The aqueous fractions were discarded and the organic layers passed through a hydrophobic frit before being concentrated in vacuo to give a tan oil. The oil was dissolved in DCM and purified by flash column chromatography on silica using 0% to 20% ethyl acetate in cyclohexane gradient elution. The relevant fractions were pooled and concentrated in vacuo to give the title compound as a yellow semi-solid (0.64 g).

MS: m/z 380, 382, 383 [MH$^+$]

Description 12

1-(3-{[(1,1-Dimethylethyl)(dimethyl)silyl]oxy}propyl)-5-isoquinolinecarbonitrile (D12)

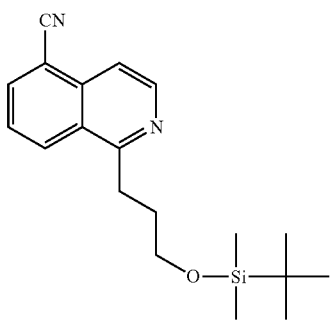

A microwave vial was charged with 5-bromo-1-(3-{[(1,1-dimethylethyl)(dimethyl)silyl]oxy}propyl)isoquinoline (D11; 640 mg, 1.68 mmol), dry, degassed N,N-dimethylformamide (DMF) (8 ml), zinc cyanide (217 mg, 1.85 mmol) and tetrakis(triphenylphosphine)palladium(0) (194 mg, 0.168 mmol). The reaction vessel was sealed and heated using microwave irradiation to 120° C. for 60 min. After cooling, the mixture was diluted with ethyl acetate, the organic layers partitioned with water (×3) and the aqueous layer discarded. The organic layers were passed through a hydrophobic frit before being concentrated in vacuo. The resultant yellow oil was purified by flash column chromatography on silica using 2% to 20% ethyl acetate in cyclohexane as eluent. The relevant fractions were pooled and concentrated in vacuo to give the title compound as a yellow oil (417 mg).
MS: m/z 327, 328, 329 [MH$^+$]

Description 13

1-(3-{[(1,1-Dimethylethyl)(dimethyl)silyl]oxy}propyl)-N-hydroxy-5-isoquinolinecarboximidamide (D13)

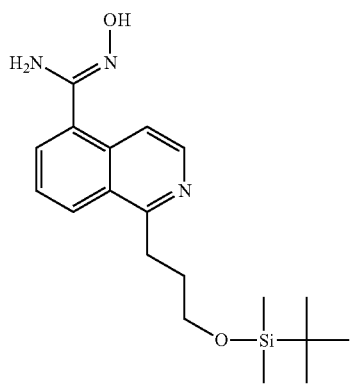

A round bottomed flask was charged with 1-(3-{[(1,1-dimethylethyl)(dimethyl)silyl]oxy}propyl)-5-isoquinolinecarbonitrile (D12; 417 mg, 1.28 mmol), ethanol (10 ml), sodium bicarbonate (107 mg, 12.8 mmol) and hydroxylamine hydrochloride (710 mg, 10.2 mmol). The vessel was fitted with a reflux condenser and warmed to 65° C. overnight. The resulting slurry was diluted with ethyl acetate and filtered through celite. The filtrate was concentrated in vacuo to give a yellow oil that was purified by flash column chromatography on silica using 0% to 100% ethyl acetate in cyclohexane as eluent. The relevant fractions were pooled and concentrated in vacuo to give the title compound as a yellow solid (280 mg).
MS: m/z 360 [MH$^+$]

Description 14

Ethyl 1-[5-(5-{3-chloro-4-[(1-methylethyl)oxy]phenyl}-1,2,4-oxadiazol-3-yl)-1-isoquinolinyl]-4-piperidinecarboxylate (D14)

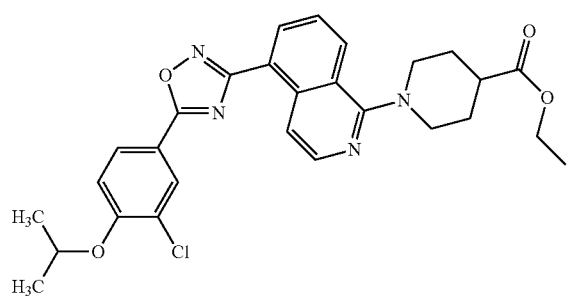

1-Chloro-5-(5-{3-chloro-4-[(1-methylethyl)oxy]phenyl}-1,2,4-oxadiazol-3-yl)isoquinoline (D7; 50 mg, 0.125 mmol), ethyl 4-piperidinecarboxylate (available from Fluorochem; 0.077 ml, 0.500 mmol) and n-butanol (0.75 ml) were heated under microwave irradiation at 175° C. for 2 h. The reaction mixture was filtered to give the title compound as an off white solid (35 mg).
MS: m/z 521 and 523 [MH$^+$]

Description 15

1,1-Dimethylethyl 4-[5-(5-{3-chloro-4-[(1-methylethyl)oxy]phenyl}-1,2,4-oxadiazol-3-yl)-1-isoquinolinyl]-1-piperazinecarboxylate (D15)

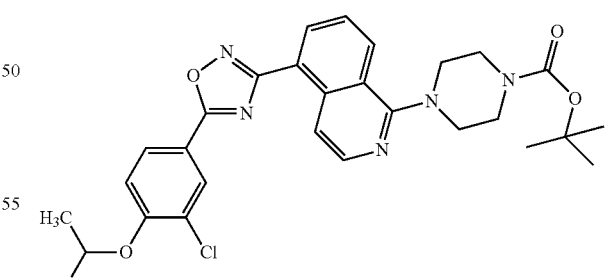

1-Chloro-5-(5-{3-chloro-4-[(1-methylethyl)oxy]phenyl}-1,2,4-oxadiazol-3-yl)isoquinoline (D7; 50 mg), 1,1-dimethylethyl 1-piperazinecarboxylate (93 mg) and n-butanol (0.5 ml) were heated under microwave irradiation at 180° C. for 1 h. After cooling the reaction mixture was filtered and the title compound was isolated as a white solid (24 mg).
MS: m/z 550 [MH$^+$]

Description 16

3-Chloro-4-[(cyclopropylmethyl)oxy]benzoyl chloride (D16)

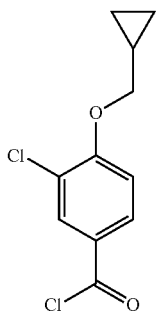

Oxalyl chloride (0.053 mL, 0.6 mmol) was added to a stirred solution of 3-chloro-4-[(cyclopropylmethyl)oxy]benzoic acid (WO 2005058848; 68 mg, 0.3 mmol) in dichloromethane (DCM) (2 ml) containing N,N-dimethylformamide (DMF) (0.02 ml) at 0° under nitrogen, and the mixture was allowed to warm to room temperature with stirring overnight. The solvent was evaporated to give the title compound as a yellow oil (ca 80 mg) which was used crude in the subsequent reaction (D46).

Description 17

3-Chloro-4-[(difluoromethyl)oxy]benzoic acid (D17)

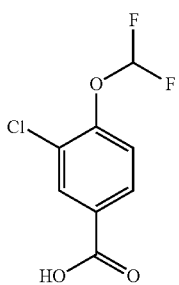

Chloro(difluoro)acetic acid (1.028 ml, 10.72 mmol) was added to methyl 3-chloro-4-hydroxybenzoate (Alfa Aesar; 1.0 g, 5.36 mmol) and potassium carbonate (1.629 g, 11.79 mmol) in N,N-dimethylformamide (DMF) (10 ml) and water (2 ml) and the mixture was heated at 100° with stirring under nitrogen for 18.5 h. The cooled mixture was partitioned between water (100 ml) and ethyl acetate (3×50 ml) and the organic layer was washed with saturated aqueous sodium chloride, dried (MgSO$_4$) and evaporated in vacuo to give the methyl ester as a colourless oil (1.06 g).

The aqueous layer was acidified with 2N aqueous hydrochloric acid and extracted with ethyl acetate. The organic layer was washed with brine, dried (MgSO4) and evaporated in vacuo to give the title compound as a colourless oil (0.28 g).

MS (ES) $C_8H_5{}^{35}ClF_2O_3$ requires 222. found 221 [M–H]$^+$.

Description 18

3-Chloro-4-[(difluoromethyl)oxy]benzoyl chloride (D18)

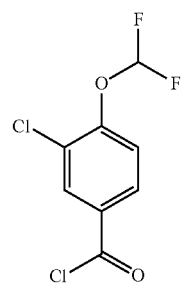

3-Chloro-4-[(difluoromethyl)oxy]benzoic acid (D17; 0.28 g, 1.258 mmol) was stirred at room temperature with oxalyl chloride (0.220 mL, 2.52 mmol) and N,N-dimethylformamide (DMF) (0.05 ml) in dry dichloromethane (DCM) (5 ml) under nitrogen for 16 h. The solvent was evaporated in vacuo to give a yellow semi-solid (380 mg) which was used crude in the subsequent reaction D47.

Description 19

Methyl 3-chloro-4-[(2,2,2-trifluoroethyl)oxy]benzoate (D19)

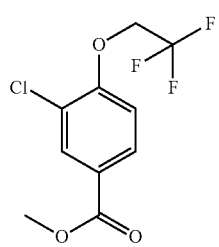

1,1,1-Trifluoro-2-iodoethane (1.162 ml, 11.80 mmol) was added to methyl 3-chloro-4-hydroxybenzoate (Alfa Aesar; 1.0 g, 5.36 mmol) and anhydrous potassium carbonate (0.889 g, 6.43 mmol) in N,N-dimethylformamide (DMF) (30.0 ml), and the mixture was heated under reflux with stirring under nitrogen for 16 h.

The cooled reaction mixture was transferred to a microwave vial and heated under microwave irradiation in at 135° for 1 h. The cooled reaction mixture was partitioned between water (150 ml) and ethyl acetate (3×100 ml), and the organic layer was washed with 50:50 brine:water and brine, dried (MgSO$_4$) and evaporated in vacuo to give a cream solid (1.39 g). The crude product was purified by flash chromatography on silica gel, eluting with 0-100% dichloromethane-cyclohexane. The appropriate fractions were combined and evaporated in vacuo to give the title compound as a white solid (0.989 g).

1H NMR (CHLOROFORM-d) Shift: 8.11 (s, 1H), 7.95 (d, J=8.5 Hz, 1H), 6.96 (d, J=8.5 Hz, 1H), 4.47 (q, J=8.0 Hz, 2H), 3.91 (s, 3H)

Description 20

3-Chloro-4-[(2,2,2-trifluoroethyl)oxy]benzoic acid (D20)

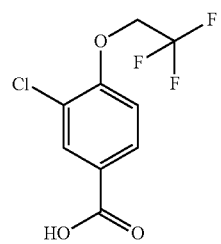

A mixture of methyl 3-chloro-4-[(2,2,2-trifluoroethyl)oxy]benzoate (D19; 0.989 g, 3.68 mmol) and lithium hydroxide (0.176 g, 7.36 mmol) in tetrahydrofuran (THF) (10 ml) and water (1 ml) was stirred under nitrogen at room temperature for 18 h.

Methanol (10 ml) and more water (4 ml) were added, and stirring was continued at room temperature for 4 h. The solvents were evaporated in vacuo to give a white solid which was acidified with 2N hydrochloric acid (10 ml), and partitioned between water (80 ml) and ethyl acetate (3×50 ml). The combined organic layers was washed with saturated aqueous sodium chloride, dried (MgSO$_4$) and evaporated in vacuo to give the title compound as a white solid (0.890 g)

MS (ES) $C_9H_6{}^{35}ClF_3O_3$ requires 254. found 253 [M−H]$^+$.

Description 21

3-Chloro-4-[(2,2,2-trifluoroethyl)oxy]benzoyl chloride (D21)

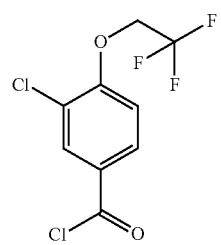

Oxalyl chloride (0.053 ml, 0.6 mmol) was added to a stirred solution of the 3-chloro-4-[(2,2,2-trifluoroethyl)oxy]benzoic acid (D20; 76 mg, 0.30 mmol) in dichloromethane (DCM) (2 ml) containing N,N-dimethylformamide (DMF) (0.02 ml) at 0° under nitrogen and the mixture was allowed to warm to room temperature with stirring overnight. The solvent was evaporated to give the title compound as a yellow solid (ca 90 mg) which was used crude in the next reaction (D48).

Description 22

Methyl 3-cyano-4-hydroxybenzoate (D22)

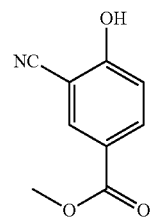

A mixture of methyl 3-bromo-4-hydroxybenzoate (Journal of Organic Chemistry (1997), 62(13), 4504-4506; 3.47 g, 15.0 mmol), potassium ferrocyanide trihydrate (1.394 g, 3.30 mmol), palladium acetate (0.034 g, 0.150 mmol), 1,1-bis (diphenylphosphino)ferrocene (0.166 g, 0.300 mmol), and sodium carbonate (1.590 g, 15.00 mmol) in dry N,N-dimethylacetamide (DMA) (30 ml) was degassed by evacuation and refilling with nitrogen, and the mixture was heated under nitrogen at 125° for 18 h. More potassium ferrocyanide trihydrate (700 mg), palladium acetate (34 mg) and 1,1'-bis (diphenylphosphino)ferrocene (166 mg) were added, and stirring was continued under nitrogen at 130° for 21.5 h. More sodium carbonate (1.59 g), palladium acetate (0.034 g, 0.150 mmol) and 1,1'-bis(diphenylphosphino)ferrocene (0.166 g, 0.300 mmol) was added, and heating was continued at 130° with stirring under nitrogen for 4 h. The solvent was evaporated in vacuo and the residue treated with glacial acetic acid (3 ml) and partitioned between water (100 ml) and ethyl acetate (100 ml). The layers separated poorly, hence the mixture was filtered through Celite filter aid, and the aqueous layer was further extracted with ethyl acetate (70 ml). The combined organic layers were washed with saturated aqueous sodium chloride, dried (MgSO$_4$) and evaporated in vacuo to give a black solid which was purified by flash chromatography on silica, eluting with 0-50% ethyl acetate-cyclohexane. The appropriate fractions were combined and evaporated in vacuo to give the title compound as a yellow solid (1.01 g)

MS (ES) $C_9H_7NO_3$ requires 177. found 176 [M−H]$^+$.

Description 23

Methyl 3-cyano-4-[(cyclopropylmethyl)oxy]benzoate (D23)

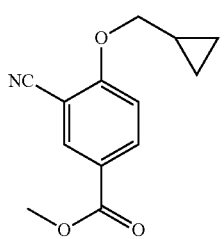

A mixture of methyl 3-cyano-4-hydroxybenzoate (D22; 120 mg, 0.677 mmol), (bromomethyl)cyclopropane (Aldrich; 0.099 ml, 1.016 mmol), and potassium carbonate (140 mg, 1.016 mmol) in dry N,N-dimethylformamide (DMF) (2 ml) was heated under microwave irradiation at 150° for 90 mins. The cooled mixture was partitioned between water (30 ml) and ethyl acetate (3×25 ml), and the organic layer was washed with 50:50 brine:water and brine, dried (MgSO$_4$) and evaporated in vacuo to give a light brown crystalline solid which was purified by flash chromatography on silica gel, eluting with 0-30% ethyl acetate-cyclohexane. The appropriate fractions were combined and evaporated in vacuo to give the title compound as a white solid (74 mg)

MS (ES) C$_{13}$H$_{13}$NO$_3$ requires 231. found 232 [M-H]$^+$.

Description 24

3-Cyano-4-[(cyclopropylmethyl)oxy]benzoic acid (D24)

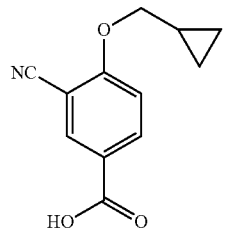

Methyl 3-cyano-4-[(cyclopropylmethyl)oxy]benzoate (D23; 74 mg, 0.320 mmol) was stirred at room temperature under nitrogen with lithium hydroxide (15.33 mg, 0.640 mmol) in tetrahydrofuran (THF) (2 ml), methanol (2 ml) and water (1 ml) for 20 h. The mixture was partitioned between water (20 ml), 2N hydrochloric acid (5 ml) and ethyl acetate (3×20 ml), and the organic layer was washed with saturated aqueous sodium chloride, dried (MgSO$_4$) and evaporated in vacuo to give the title compound as a white solid (51 mg)

MS (ES) C$_{12}$H$_{11}$NO$_3$ requires 217. found 216 [M-H]$^+$.

Description 25

3-Cyano-4-[(cyclopropylmethyl)oxy]benzoyl chloride (D25)

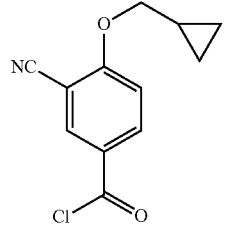

Oxalyl chloride (0.040 ml, 0.460 mmol) was added to a stirred solution of 3-cyano-4-[(cyclopropylmethyl)oxy]benzoic acid (D24; 50 mg, 0.230 mmol) in dichloromethane (DCM) (2 ml) containing N,N-dimethylformamide (DMF) (0.02 ml) at room temperature under nitrogen, and the mixture was stirred at room temperature for 2 h. The solvent was evaporated in vacuo to give the title compound (54.2 mg) which was used in the subsequent step (D49) without purification.

Description 26

Methyl 2-hydroxy-4-pyridinecarboxylate (D26)

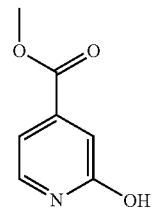

To a suspension of 2-hydroxy-4-pyridinecarboxylic acid (Journal of the Chemical Society (1960), 1430-4; 8.45 g, 60.8 mmol) in methanol (200 ml) under nitrogen was added thionyl chloride (7.23 g, 60.8 mmol) dropwise at room temperature. The mixture was then heated under reflux for 4 hrs before being cooled to room temperature. The solvent was removed under vacuum and the residue was dissolved in ethyl acetate. A saturated aqueous solution of sodium bicarbonate was added which formed a precipitate that was removed by filtration. The filtrate was further basified with 2N aqueous sodium hydroxide. The layers were separated and the organic phase was further extracted with ethyl acetate. The combined organic extracts were washed with brine (×2), dried over magnesium sulphate and concentrated under vacuum to give the title compound as a pale brown oil (3.4 g).

MS: m/z 154 [MH$^+$].

Description 27

Methyl 1-(2-methylpropyl)-2-oxo-1,2-dihydro-4-pyridinecarboxylate (D27)

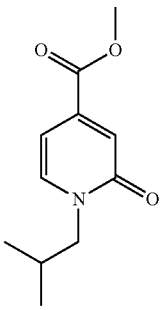

To a solution of methyl 2-hydroxy-4-pyridinecarboxylate (D26; 1.02 g, 6.66 mmol) in N,N-dimethylformamide (20 ml) was added sodium hydride (60%; 0.293 g, 7.33 mmol). The resulting solution was stirred at room temperature for 15 mins. 1-Bromo-2-methylpropane (0.87 ml, 7.99 mmol) was then added and the mixture was stirred at 80° C. for 2 hrs. The reaction was quenched with methanol and the solvent was removed under vacuum. The residue was partitioned between ethyl acetate and water, the organic layer dried over magnesium sulphate and concentrated under vacuum. The crude material was purified by chromatography on silica, eluting with 50-80% ethyl acetate in cyclohexane gave the title compound as a light blue solid (450 mg). MS: m/z 210 [MH+]. O-alkylated material was also isolated.

Description 28

1-(2-Methylpropyl)-2-oxo-1,2-dihydro-4-pyridinecarboxylic acid (D28)

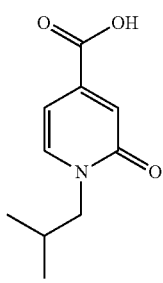

A 2M aqueous solution of sodium hydroxide (5.38 ml, 10.75 mmol) was added to a solution of methyl 1-(2-methylpropyl)-2-oxo-1,2-dihydro-4-pyridinecarboxylate (D27; 0.45 g, 2.151 mmol) in methanol (10 ml). The mixture was stirred at room temperature for 2 hrs and then the solvent was removed under vacuum. The residue was taken up with water, neutralised with 2M HCl and extracted with ethyl acetate. The organic layer was washed with water, dried over magnesium sulphate and concentrated under vacuum to give the title compound as a white solid (400 mg).
MS: m/z 196 [MH+].

Description 29

5-formyl-2-[(2,2,2-trifluoroethyl)oxy]benzonitrile (D29)

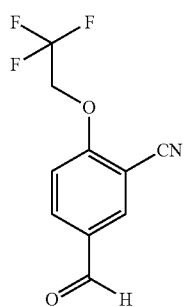

A solution of 2,2,2-trifluoroethanol (0.098 ml, 1.341 mmol) in DMF (9 ml) was cooled in an ice bath. Sodium hydride (60%; 38.6 mg, 0.965 mmol) was added and the resulting mixture was stirred for 10 mins before adding 2-fluoro-5-formylbenzonitrile (Aldrich; 200 mg, 1.341 mmol). The ice bath was removed and the reaction mixture was stirred at room temperature overnight. The mixture was partitioned between ethyl acetate (15 ml) and brine (7 ml). The organic layer was washed with water (2×8 ml) and brine (7 ml), passed through a phase separation cartridge and concentrated under vacuum. The residue was purified by column chromatography on silica, eluting with 0-40% ethyl acetate in cyclohexane gave the title compound as a white solid (155 mg).
MS: m/z 113 [M−H−].

Description 30

3-cyano-4-[(2,2,2-trifluoroethyl)oxy]benzoic acid (D30)

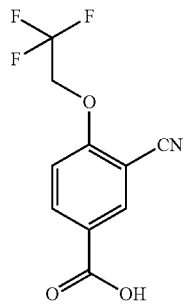

5-formyl-2-[(2,2,2-trifluoroethyl)oxy]benzonitrile (D29; 155 mg, 0.676 mmol) was dissolved in t-butanol (2 ml). A solution of potassium dihydrogen phosphate (23.01 mg, 0.169 mmol) and sodium chlorite (184 mg, 2.029 mmol) in water (2 ml) was added, followed by 2-methyl-2-butene (1.015 ml, 2.029 mmol). The resulting mixture was stirred at room temperature for 4 hrs. A solution of sodium disulfite (450 mg) in water (10 ml) was added carefully. DCM (15 ml) was then added and the phases were separated. The aqueous layer was then extracted once more with DCM (15 ml). The combined organic extracts were passed through a phase separation cartridge, concentrated under vacuum and dried in a vacuum oven to give the title compound as a white solid (173 mg).
MS: m/z 113 [M−H−].

Description 31

3-Cyano-4-fluorobenzoic acid (D31)

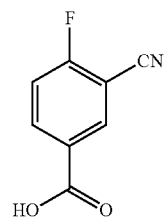

Sodium chlorite (1.819 g, 20.12 mmol) and potassium dihydrogen phosphate (0.228 g, 1.676 mmol) in water (20.00 ml) was added to 2-fluoro-5-formylbenzonitrile (Aldrich; 1 g, 6.71 mmol) in t-butanol (20 ml), followed by 2-methyl-2-butene (10.06 ml, 20.12 mmol). The resulting mixture was stirred at room temperature for 2 hrs. A solution of 4.5 g of sodium disulfite in water (100 ml) was then added carefully. DCM (150 ml) was added and phases were separated. The aqueous layer was then extracted once more with DCM (150 ml). The combined organic extracts were passed through a phase separation cartridge, concentrated under vacuum and dried in a vacuum oven to give the title compound as a white solid (1.09 g).
MS: m/z 164 [M−H−].

Description 32

Methyl 2-chloro-4-[(1-methylethyl)oxy]benzoate (D32)

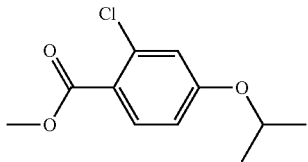

Methyl 2-chloro-4-hydroxybenzoate (Acros Organics; 0.2 g, 1.072 mmol) was stirred with 2-bromopropane (0.201 ml, 2.144 mmol) and potassium carbonate (296 mg, 2.144 mmol) in DMF (2 ml) at 100° C. for 1.5 hr. The mixture was allowed to cool to room temperature and filtered. The filtrate was concentrated under vacuum and the residue was purified by Mass-Directed Auto-Preparative HPLC (formic acid modifier) to give the title compound as a yellow oil (150 mg).
MS: m/z 229 [MH$^+$].

Description 33

5-Chloro-6-[(1-methylethyl)oxy]-3-pyridinecarbonyl chloride (D33)

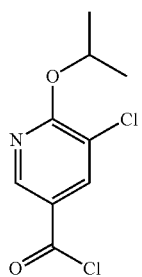

Oxalyl chloride (0.07 ml, 0.800 mmol) was added to a stirred solution of 5-chloro-6-[(1-methylethyl)oxy]-3-pyridinecarboxylic acid (WO 2008074820; 86 mg, 0.40 mmol) in dichloromethane (DCM) (2 ml) containing N,N-dimethylformamide (DMF) (0.02 ml) at 0° under nitrogen and the mixture was allowed to warm to room temperature with stirring overnight. The solvent was evaporated in vacuo to give a yellow gum (123 mg) which was used in the subsequent reaction (D53) without further purification

Description 34

1,1-Dimethylethyl 3-(5-bromo-1-isoquinolinyl)propanoate (D34)

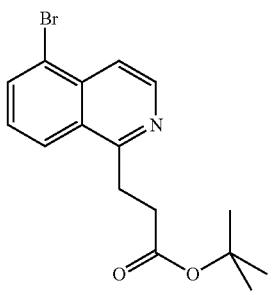

A solution of 5-bromo-2-(phenylcarbonyl)-1,2-dihydro-1-isoquinolinecarbonitrile (D10; 70 g, 206 mmol) and 1,1-dimethylethyl 3-bromopropanoate (Aldrich; 37.9 ml, 227 mmol) in dry, degassed DMF (250 ml) was added dropwise over 40 mins to a suspension of sodium hydride (60%; 24.76 g, 619 mmol) in dry, degassed DMF (750 ml) at −10° C. under nitrogen. The mixture was stirred at −10° C. for 10 mins, then allowed to warm to room temp over 3 h. Water (1500 ml) was cautiously added and the mixture extracted with ethyl acetate (3×500 ml). The combined organic extracts were washed with brine (5×500 ml) and dried (MgSO4). The solvent was evaporated to give a brown oil. The crude intermediate was dissolved in THF (700 ml) and lithium hydroxide (24.71 g, 1032 mmol) in water (100 ml) (note: not all soluble) was added. The mixture was vigorously stirred for 30 h, then stored in the fridge over the weekend. The mixture was partitioned between water (700 ml) and ethyl acetate (3×500 ml) and the combined organic extracts washed with brine (2×500 ml) and dried (MgSO4). The solvent was evaporated and the residue was purified by chromatography on silica eluting with 5-15% ethyl acetate in isohexane gave the title compound (48.2 g)
MS (ES) $C_{16}H_{18}BrNO_2$ requires 336. found 336/338 [M+H]$^+$.

Description 35

1,1-Dimethylethyl 3-(5-cyano-1-isoquinolinyl)propanoate (D35)

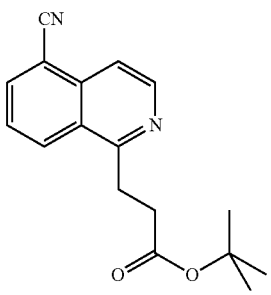

1,1-Dimethylethyl 3-(5-bromo-1-isoquinolinyl)propanoate (D34; 60 g, 178 mmol) was taken up in dry DMA (600 ml) followed by the addition of potassium hexacyanoferrate hexahydrate (22.61 g, 53.5 mmol) then palladium acetate (0.801 g, 3.57 mmol) dppf (3.96 g, 7.14 mmol) and then finally sodium carbonate (22.7 g, 214 mmol). The reaction mixture was stirred at 120° C. overnight, cooled and diluted with ethyl acetate (500 ml) and filtered through Celite. The filtrate was concentrated in vacuo. and the dark residue was taken up in DCM (250 ml) and filtered through Celite and cotton wool. The DCM solution (250 ml) was purified by chromatography using a gradient system 0-100% ethyl acetate in isohexane to give the title compound (25.3 g)
MS (ES) $C_{17}H_{18}N_2O_2$ requires 282. found 283 [M+H]$^+$.

Description 36

1,1-Dimethylethyl 3-{5-[(hydroxyamino)(imino)methyl]-1-isoquinolinyl}propanoate (D36)

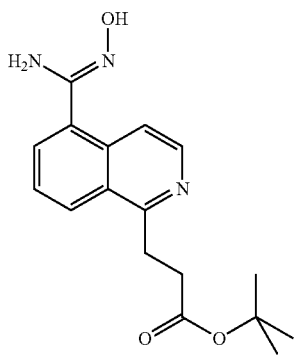

Hydroxylamine hydrochloride (24.51 g, 353 mmol) was added to a mixture of 1,1-dimethylethyl 3-(5-cyano-1-isoquinolinyl)propanoate (D35; 24.9 g, 88 mmol) and sodium bicarbonate (44.5 g, 529 mmol) in ethanol (200 ml) and the mixture heated at 60° C. for 5 h. The cooled mixture was filtered and the filtrate concentrated in vacuo. The residue was partitioned between water (100 ml) and ethyl acetate (3×100 ml) and the combined organic extracts washed with brine (100 ml) and dried (MgSO4). The solvent was evaporated to give a pale yellow solid which was triturated under ether (100 ml) and filtered to give the title compound as a colourless solid (19.91 g)

MS (ES) $C_{17}H_{21}N_3O_3$ requires 315. found 316 [M+H]$^+$.

Description 37

N-Hydroxy-1-oxo-1,2-dihydro-5-isoquinolinecarboximidamide (D37)

Hydroxylamine hydrochloride (3.18 g) and sodium bicarbonate (5.7 g) were added to a suspension of 1-oxo-1,2-dihydro-5-isoquinolinecarbonitrile (Journal of Organic Chemistry (1964), 29(9), 2534-42; 3.9 g) in ethanol (600 ml) at room temperature. The reaction mixture was heated to reflux and stirred for 48 hours. After cooling, the suspension was filtered. The solid was collected, washed with water (2×100 ml) and ethanol (100 ml) to give the title compound (2.75 g).

H$^1$ NMR: δH (DMSO-d$_6$, 400 MHz): 5.94 (2H, s), 6.85 (1H, dd), 7.18 (1H, d), 7.47 (1H, t), 7.69 (1H, dd), 8.22 (1H, d), 9.58 (1H, br s), 11.30 (1H, br s). MS (ES): $C_{10}H_9N_3O_2$ requires 203. found 204.1 (M+H$^+$).

Description 38

1-Bromo-5-isoquinolinecarbonitrile (D38)

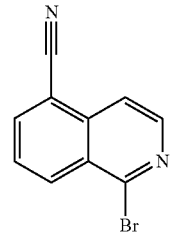

Phosphorus oxybromide (6.7 g) was added to a suspension of 1-oxo-1,2-dihydro-5-isoquinolinecarbonitrile (2 g) in 1,2-dichloroethane (100 ml). The resulting suspension was heated under reflux overnight. The solvent was removed in vacuo and the residue was washed with aq NaHCO$_3$ (2N, 2×15 ml) to afford, after drying, the title compound (2.27 g). δH (DMSO-d$_6$, 400 MHz): 7.99 (2H, m), 8.54 (3H, m).

MS (ES): $C_{10}H_5BrN_2$ requires 232. found 233.0 (M)

Description 39

5-(5-{3-Chloro-4-[(1-methylethyl)oxy]phenyl}-1,2,4-oxadiazol-3-yl)-1(2H)-isoquinolinone (D39)

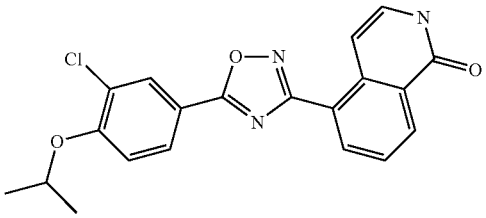

1-Ethyl-3-(3-dimethylaminopropyl) carbodiimide hydrochloride (EDCI; 5.2 g) and hydroxybenzotriazole (HOBt; 3.6 g) were added to a solution of 3-chloro-4-[(1-methylethyl)oxy]benzoic acid (D3; 2.9 g) in DMF (200 ml) at room temperature, and the resulting solution was stirred for 30 minutes. N-hydroxy-1-oxo-1,2-dihydro-5-isoquinolinecarboximidamide (D37, 2.75 g) was added and the suspension was stirred at room temperature for 2 hours. The reaction mixture was heated to 140° C. and stirred for 1 hour. The solvent was evaporated and the residue was washed with water, followed by ethyl acetate to give the title compound (2.6 g).

MS (ES): $C_{20}H_{16}ClN_3O_3$ requires 381. found 382.1 (M+H$^+$).

Description 40

1-Bromo-5-(5-{3-chloro-4-[(1-methylethyl)oxy]phenyl}-1,2,4-oxadiazol-3-yl)isoquinoline (D40)

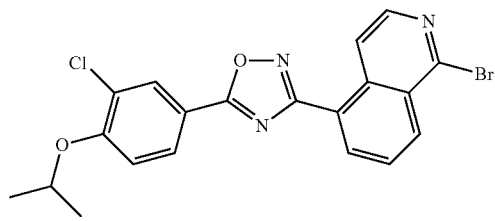

Phosphorus oxybromide (3.9 g) was added to a suspension of 5-(5-{3-chloro-4-[(1-methylethyl)oxy]phenyl}-1,2,4-oxadiazol-3-yl)-1(2H)-isoquinolinone (D39; 2.6 g) in 1,2-dichloroethane (300 ml) at room temperature. The resulting suspension was heated under reflux and stirred overnight. The reaction mixture was poured into cold sat. aq. NaHCO$_3$ and the organic layer was separated. The aqueous layer was extracted with DCM (100 ml). The organic fractions were combined and dried over anhydrous sodium sulphate. The dried solution was filtered and the filtrate was concentrated to give the title compound (1 g).

δH (CDCl$_3$, 400 MHz): 1.48 (6H, d), 4.76 (1H, m), 7.11 (1H, d), 8.10 (2H, m), 8.29 (1H, d), 8.57 (1H, d), 8.71 (1H, d), 8.95 (1H, dd), 9.40 (1H, d). MS (ES): $C_{20}H_{15}BrClN_3O_2$ requires 443. found 444.0 (M).

Description 41

Ethyl 4-[5-(5-{3-chloro-4-[(1-methylethyl)oxy]phenyl}-1,2,4-oxadiazol-3-yl)-1-isoquinolinyl]butanoate (D41)

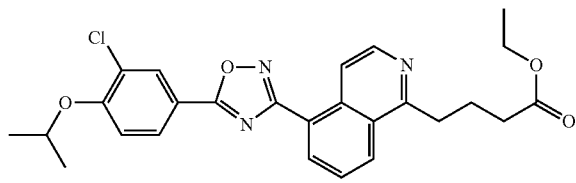

Bromo[4-(ethyloxy)-4-oxobutyl]zinc (Aldrich; 0.5 M in THF, 2 ml) was added dropwise to a solution of 1-bromo-5-(5-{3-chloro-4-[(1-methylethyl)oxy]phenyl}-1,2,4-oxadiazol-3-yl)isoquinoline (D40; 0.15 g) and tetrakis(triphenylphosphine)palladium(0) (50 mg) in THF (5 ml). The resulting solution was heated to reflux for 1 hour. The solvent was evaporated in vacuo and the residue was dissolved in DCM (20 ml). The organic solution was washed with 0.5 M aq. NaOH (8 ml), then dried over anhydrous sodium sulphate. The dried solution was filtered and the filtrate was concentrated. The residue was purified by column chromatography to give the title compound (0.1 g).

MS (ES): $C_{26}H_{26}ClN_3O_4$ requires 479. found 480.2 (M+H$^+$).

Description 42

Ethyl 4-(5-cyano-1-isoquinolinyl)butanoate (D42)

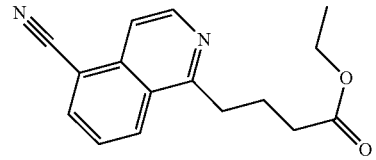

Bromo[4-(ethyloxy)-4-oxobutyl]zinc (0.5 M in THF, 26 ml) was added dropwise to a solution of 1-bromo-5-isoquinolinecarbonitrile (D38; 1 g) and tetrakis(triphenylphosphine)palladium(0) (20 mg) in THF (5 ml). The resulting solution was heated to reflux for 3 hours. The solvent was evaporated in vacuo and the residue was dissolved in DCM (50 ml). The organic solution was washed with 0.5 M aq. NaOH (15 ml), followed by washing with water and brine. The organic phase was dried over anhydrous sodium sulphate. The dried solution was filtered and the filtrate was concentrated. The residue was purified by column chromatography to give the title compound (0.65 g). δH (CDCl$_3$, 400 MHz): 1.28 (3H, t), 2.20 (2H, m), 2.50 (2H, m), 3.41 (2H, m), 4.16 (2H, q), 7.71 (1H, dd), 7.93 (1H, d), 8.12 (1H, dd), 8.54 (1H, d), 8.63 (1H, d). MS (ES): $C_{16}H_{16}N_2O_2$ requires 268. found 269.1 (M+H$^+$).

Description 43

Ethyl 4-{5-[(hydroxyamino)(imino)methyl]-1-isoquinolinyl}butanoate (D43)

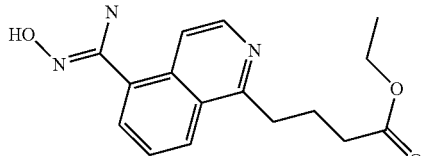

Hydroxylamine hydrochloride (0.36 g) was added to a suspension of ethyl 4-(5-cyano-1-isoquinolinyl)butanoate (D42; 0.65 g) and NaHCO$_3$ (0.66 g) in ethanol (20 ml). The mixture was heated to reflux for 24 hours. The solvent was evaporated in vacuo. The residue was washed with water (2×10 ml) to afford, after drying, the title compound (0.6 g). MS (ES): $C_{16}H_{19}N_3O_3$ requires 301. found 302.2 (M+H$^+$).

Description 44

Ethyl 4-[5-(5-{5-chloro-6-[(1-methylethyl)oxy]-3-pyridinyl}-1,2,4-oxadiazol-3-yl)-1-isoquinolinyl]butanoate (D44)

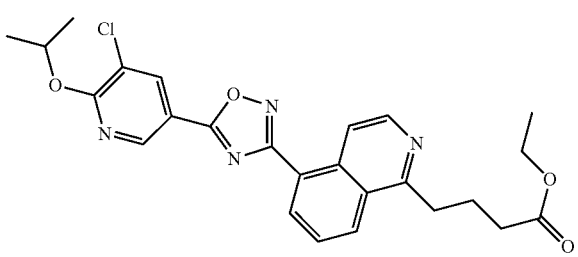

1-Ethyl-3-(3-dimethylaminopropyl) carbodiimide hydrochloride (EDCI; 0.77 g) and hydroxybenzotriazole (HOBt; 0.54 g) were added sequentially to a solution of 5-chloro-6-[(1-methylethyl)oxy]-3-pyridinecarboxylic acid (WO 2008128951; 0.43 g) in THF (20 mL) at room temperature and the resulting solution was stirred for 30 minutes. Ethyl 4-{5-[(hydroxyamino)(imino)methyl]-1-isoquinolinyl}butanoate (D43; 0.6 g) was added and the resulting suspension was stirred at room temperature for 1 hour. Tetra-n-butylammonium fluoride (TBAF; 1.57 g) was added to the reaction mixture and the resulting solution was heated to reflux for overnight. The solvent was evaporated in vacuo and the residue was dissolved in ethyl acetate (50 ml). The organic phase was washed with water and brine, then dried over anhydrous sodium sulphate. The dried solution was filtered and the filtrate was concentrated. The residue was purified by column chromatography to give the title compound (0.36 g). δH (CDCl$_3$, 400 MHz): 1.29 (3H, t), 1.47 (6H, d), 2.25 (2H, m), 2.54 (2H, m), 3.50 (2H, m), 4.18 (2H, q), 5.52 (1H, m), 7.81 (1H, dd), 8.45 (1H, d), 8.53 (1H, d), 8.61 (2H, m), 8.79 (1H, d), 8.94 (1H, d). MS (ES): $C_{25}H_{25}ClN_4O_4$ requires 480. found 481.2 (M+H$^+$).

Description 45

1,1-Dimethylethyl 3-[5-(5-{3-chloro-4-[(cyclopropylmethyl)oxy]phenyl}-1,2,4-oxadiazol-3-yl)-1-isoquinolinyl]propanoate (D45)

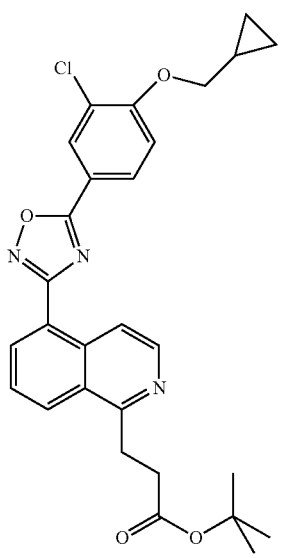

A solution of 3-chloro-4-[(cyclopropylmethyl)oxy]benzoyl chloride (D16; 73.5 mg, 0.3 mmol) in dry DMF (1.5 ml) was added to a stirred solution of 1,1-dimethylethyl 3-{5-[(hydroxyamino)(imino)methyl]-1-isoquinolinyl}propanoate (D36; 85 mg, 0.270 mmol) and triethylamine (0.063 ml, 0.450 mmol) in dry DMF (1.5 ml) at 0° and the mixture was stirred at 0° for 1.5 h. The mixture was then heated at 100° with stirring under nitrogen for 16 h. The cooled mixture was partitioned between saturated aqueous sodium bicarbonate (30 ml) and ethyl acetate (3×20 ml), and the organic layer was washed with 50:50 brine:water and brine, dried (MgSO$_4$) and evaporated in vacuo to give a brown oil. The crude product was purified by flash chromatography on silica gel, eluting with 0-30% ethyl acetate-cyclohexane. The appropriate fractions were combined and evaporated in vacuo to give the title compound as a white solid (22 mg).

MS (ES) $C_{28}H_{28}{}^{35}ClN_3O_4$ requires 505. found 506 [M+H]$^+$.

Description 46

1,1-Dimethylethyl 3-[5-(5-{3-chloro-4-[(difluoromethyl)oxy]phenyl}-1,2,4-oxadiazol-3-yl)-1-isoquinolinyl]propanoate (D46)

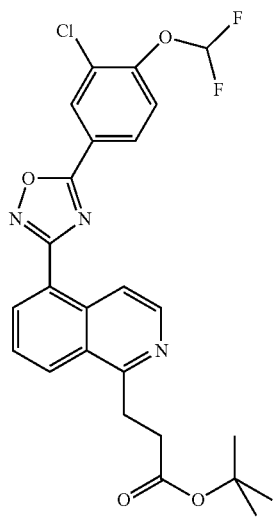

A solution of 3-chloro-4-[(difluoromethyl)oxy]benzoyl chloride (D18; 69.5 mg, 0.289 mmol) in dry DMF (1 ml) was added to a stirred solution of 1,1-dimethylethyl 3-{5-[(hydroxyamino)(imino)methyl]-1-isoquinolinyl}propanoate (D36; 70 mg, 0.222 mmol) and triethylamine (0.046 ml, 0.333 mmol) in dry DMF (2 ml) at 0° under nitrogen and stirring was continued at room temperature for 50 min, then heated at 100° for 5 h. The cooled mixture was partitioned between saturated aqueous sodium bicarbonate (30 ml) and ethyl acetate (3×20 ml), and the organic layer was washed with 50:50 brine:water and brine, dried (MgSO$_4$) and evaporated in vacuo to give a brown gum. The crude product was purified by flash chromatography on silica gel, eluting with 0-30% ethyl acetate-cyclohexane. The appropriate fractions were combined and evaporated in vacuo to give the title compound as an off-white solid (32 mg).

MS (ES) $C_{25}H_{22}{}^{35}ClF_2N_3O_4$ requires 501. found 502 [M+H]$^+$.

Description 47

1,1-Dimethylethyl 3-[5-(5-{3-chloro-4-[(2,2,2-trifluoroethyl)oxy]phenyl}-1,2,4-oxadiazol-3-yl)-1-isoquinolinyl]propanoate (D47)

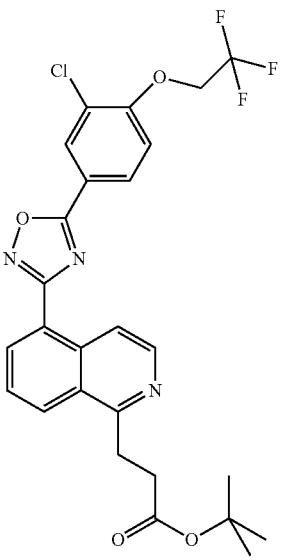

A solution of 3-chloro-4-[(2,2,2-trifluoroethyl)oxy]benzoyl chloride (D21; 82 mg, 0.30 mmol) in dry DMF (1.5 ml) was added to a stirred solution of 1,1-dimethylethyl 3-{5-[(hydroxyamino)(imino)methyl]-1-isoquinolinyl}propanoate (D36; 85 mg, 0.270 mmol) and triethylamine (0.063 ml, 0.450 mmol) in dry DMF (1.5 ml) at 0° and the mixture was stirred at 0° for 1.5 h then at 100° with stirring under nitrogen for 16 h. The cooled mixture was partitioned between saturated aqueous sodium bicarbonate (30 ml) and ethyl acetate (3×20 ml), and the organic layer was washed with 50:50 brine:water and brine, dried (MgSO$_4$) and evaporated in vacuo to give a brown oil (130 mg). The crude product was purified by flash chromatography on silica gel, eluting with 0-30% ethyl acetate-cyclohexane. The appropriate fractions were combined and evaporated in vacuo to give the title compound as a white solid (55 mg).

MS (ES) $C_{26}H_{23}{}^{35}ClF_3N_3O_4$ requires 533. found 534 [M+H]$^+$.

Description 48

1,1-Dimethylethyl 3-[5-(5-{3-cyano-4-[(cyclopropylmethyl)oxy]phenyl}-1,2,4-oxadiazol-3-yl)-1-isoquinolinyl]propanoate (D48)

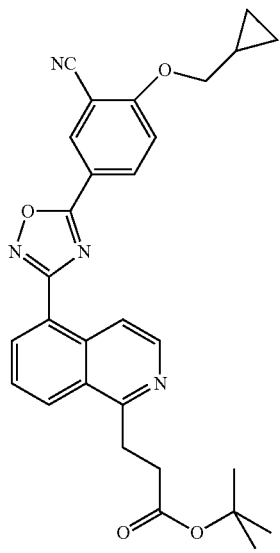

A solution of 3-cyano-4-[(cyclopropylmethyl)oxy]benzoyl chloride (D25; 54.2 mg, 0.23 mmol) in dry DMF (1.5 ml) was added to a stirred solution of 1,1-dimethylethyl 3-{5-[(hydroxyamino)(imino)methyl]-1-isoquinolinyl}propanoate (D36; 68.9 mg, 0.219 mmol) and triethylamine (0.048 ml, 0.345 mmol) in dry DMF (1.5 ml) at 0° and the mixture was stirred at 0° for 1.5 h. The mixture was then heated at 100° with stirring under nitrogen for 16 h. The cooled mixture was partitioned between saturated aqueous sodium bicarbonate (40 ml) and ethyl acetate (3×25 ml), and the combined organic layers washed with 50:50 brine:water and brine, dried (MgSO$_4$) and evaporated in vacuo to give a brown oil which was purified by flash chromatography on silica gel, eluting with 0-40% ethyl acetate-cyclohexane. The appropriate fractions were combined and evaporated in vacuo to give the title compound as an off-white solid (36 mg)

MS (ES) $C_{29}H_{28}N_4O_4$ requires 496. found 497 [M+H]$^+$.

Description 49

1,1-Dimethylethyl 3-[5-(5-{3-cyano-4-[(2,2,2-trifluoroethyl)oxy]phenyl}-1,2,4-oxadiazol-3-yl)-1-isoquinolinyl]propanoate (D49)

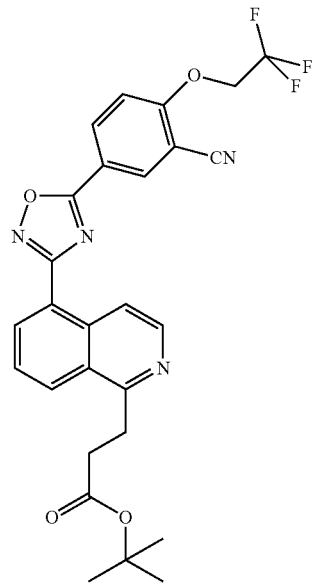

3-Cyano-4-[(2,2,2-trifluoroethyl)oxy]benzoic acid (D29; 0.171 g, 0.698 mmol) was stirred in DMF (4.5 ml) with HATU (0.318 g, 0.837 mmol) and DIPEA (0.366 ml, 2.093 mmol) at room temperature for 20 mins. 1,1-Dimethylethyl 3-{5-[(hydroxyamino)(imino)methyl]-1-isoquinolinyl}propanoate (D36, 0.22 g, 0.698 mmol) was added and the resulting mixture was heated to 120° C. for 30 mins in a Biotage Initiator microwave. The solvent was removed under vacuum and diethyl ether was added to the residue to give a colourless solid. Methanol was added to dissolve the brown oil remaining and the mixture filtered. A white solid was collected, which was dried in a vacuum oven to give the title compound as a white solid (164 mg).

MS: m/z 525/526 [MH$^+$].

Description 50

1,1-Dimethylethyl 3-{5-[5-(3-cyano-4-fluorophenyl)-1,2,4-oxadiazol-3-yl]-1-isoquinolinyl}propanoate (D50)

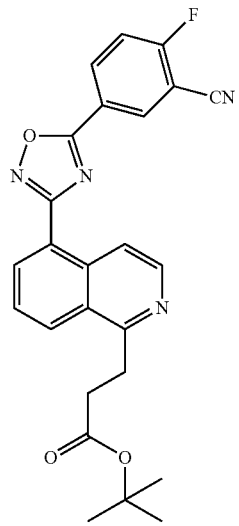

3-Cyano-4-fluorobenzoic acid (D31; 0.288 g, 1.744 mmol) was stirred at room temperature in 5 ml of DMF with HATU (0.723 g, 1.903 mmol) and DIPEA (0.831 ml, 4.76 mmol) for 10 mins. 1,1-Dimethylethyl 3-{5-[(hydroxyamino)(imino)methyl]-1-isoquinolinyl}propanoate (D36, 0.5 g, 1.585 mmol) and 5 ml of DMF were added, and the resulting mixture was stirred in a Biotage Initiator microwave at 120° C. for 30 mins. The solvent was removed under vacuum and the residue was purified by column chromatography on silica, eluting with 0-40% ethyl acetate in cyclohexane, to give the title compound as a white solid (67 mg).

MS: m/z 445/446 [MH+].

Description 51

1,1-Dimethylethyl 3-(5-{5-[3-cyano-4-(3-fluoro-1-pyrrolidinyl)phenyl]-1,2,4-oxadiazol-3-yl}-1-isoquinolinyl)propanoate (D51)

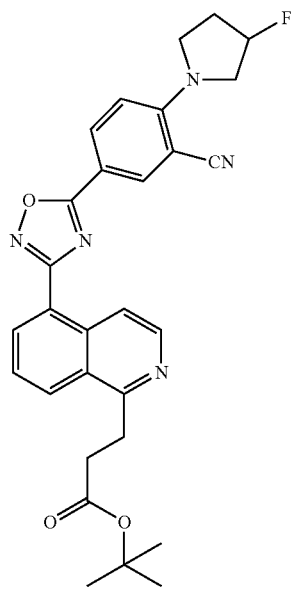

A solution of 3-fluoropyrrolidine (Anichem Product List; 16.39 mg, 0.130 mmol) in DMF (2.5 ml) was cooled in an ice bath and sodium hydride (6.89 mg, 0.172 mmol) was added. The mixture was stirred for 10 mins then 1,1-dimethylethyl 3-{5-[5-(3-cyano-4-fluorophenyl)-1,2,4-oxadiazol-3-yl]-1-isoquinolinyl}propanoate (D50; 58 mg, 0.130 mmol) was added. The ice bath was removed and the solution was stirred at room temperature for 3 hrs. Further sodium hydride (3.13 mg, 0.078 mmol) was added and the resulting solution was stirred at room temperature overnight. The mixture was partitioned between ethyl acetate and brine. The organic layer was dried with magnesium sulphate and concentrated under vacuum. The residue was purified by Mass-Directed Auto-Preparative HPLC (formic acid modifier) to provide the title compound as a cream solid (14 mg).

MS: m/z 514/515 [MH+].

Description 52

1,1-Dimethylethyl 3-[5-(5-{3-cyano-4-[(1-methylethyl)oxy]phenyl}-1,2,4-oxadiazol-3-yl)-1-isoquinolinyl]propanoate (D52)

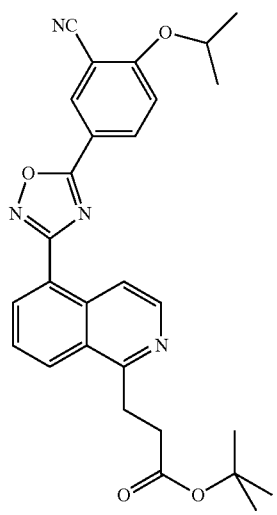

A solution of 3-cyano-4-[(1-methylethyl)oxy]benzoyl chloride (WO2008128951; 89 mg, 0.4 mmol) in dry DMF (1.5 ml) was added to a stirred solution of 1,1-dimethylethyl 3-{5-[(hydroxyamino)(imino)methyl]-1-isoquinolinyl}propanoate (D36; 114 mg, 0.360 mmol) and triethylamine (0.084 mL, 0.600 mmol) in dry DMF (1.5 ml) at 0° and the mixture was allowed to warm to room temperature and stirred for 45 min.

The mixture was partitioned between saturated aqueous sodium bicarbonate (30 ml) and ethyl acetate (3×20 ml) and the combined organic layers were washed with 50:50 brine:water and brine, dried (MgSO$_4$) and evaporated in vacuo to give a brown gum (150 mg) which was purified by flash chromatography on silica gel, eluting with 0-40% ethyl acetate-cyclohexane. The appropriate fractions were combined and evaporated in vacuo to give the title compound as a white solid (66 mg).

MS (ES) $C_{28}H_{28}N_4O_4$ requires 484. found 485 [M+H]+.

Description 53

1,1-Dimethylethyl 3-[5-(5-{5-chloro-6-[(1-methylethyl)oxy]-3-pyridinyl}-1,2,4-oxadiazol-3-yl)-1-isoquinolinyl]propanoate (D53)

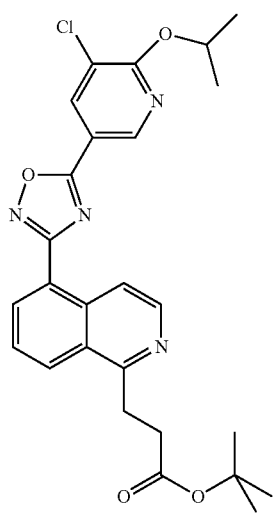

A solution of 5-chloro-6-[(1-methylethyl)oxy]-3-pyridinecarbonyl chloride (D33; 94 mg, 0.4 mmol) in dry DMF (1.5 ml) was added to a stirred solution of 1,1-dimethylethyl 3-{5-[(hydroxyamino)(imino)methyl]-1-isoquinolinyl}propanoate (D36; 114 mg, 0.360 mmol) and triethylamine (0.084 ml, 0.600 mmol) in dry DMF (1.5 ml) at 0° and the mixture was allowed to warm to room temperature and stirred for 45 min.

The mixture was partitioned between saturated aqueous sodium bicarbonate (30 ml) and ethyl acetate (3×20 ml) and the combined organic layers were washed with 50:50 brine:water and brine, dried (MgSO$_4$) and evaporated in vacuo to give a brown gum which was purified by flash chromatography on silica gel, eluting with 0-40% ethyl acetate-cyclohexane. The appropriate fractions were combined and evaporated in vacuo to give the title compound as a white solid (150 mg).

MS (ES) $C_{26}H_{27}ClN_4O_4$ requires 494. found 495 [M+H]$^+$.

EXAMPLE 1

3-[5-(5-{3-Chloro-4-[(1-methylethyl)oxy]phenyl}-1,2,4-oxadiazol-3-yl)-1-isoquinolinyl]propanoic acid lithium salt (E1)

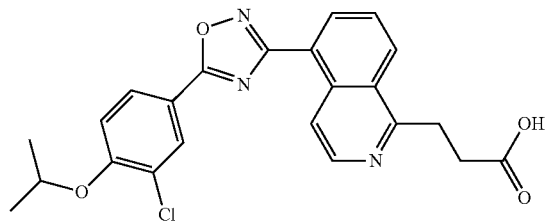

1-Chloro-5-(5-{3-chloro-4-[(1-methylethyl)oxy]phenyl}-1,2,4-oxadiazol-3-yl)isoquinoline (D7; 80 mg, 0.2 mmol), potassium carbonate (138 mg, 1 mmol) and 1,1'-bis(diphenylphosphino)ferrocene-palladium(II)dichloride dichloromethane complex (16 mg, 0.02 mmol) were stirred in a 20 ml microwave vial until the solids were well mixed. N-methyl-2-pyrrolidinone (12 ml) was added and argon bubbled through the mixture which was then allowed to stir at room temperature under argon for 8 minutes when it had a reddy brown appearance. The tube was sealed and a 0.5M solution of bromo[3-(ethyloxy)-3-oxopropyl]zinc in THF (available from Alfa Aesar; 2 ml, 1 mmol) was added and the suspension was stirred for 30 minutes to give a pale yellow/brown appearance. The mixture was heated under microwave irradiation at 100° C. for 5 minutes when it contained predominantly product.

This procedure was repeated until 750 mg of the starting material had been consumed, when the reaction mixtures were combined and chromatographed over an SCX cation exchange column (Biotage, 50 g) which was washed with methanol and eluted first with 0.5M methanolic ammonia and then a 1M solution of ammonia in a mixture of methanol and dichloromethane. The eluate was evaporated to dryness and chromatographed over a column of silica eluting with dichloromethane/EtOAC (9:1) to give a mixture of the ethyl and methyl esters of the title compound which were triturated with ether to yield a buff solid (369 mg). MS (+ve ion electrospray) m/z 452 (MH$^+$ methyl ester), m/z 466 (MH$^+$ ethyl ester).

The esters (365 mg) were dissolved in a mixture of methanol/THF/water (1:1:1, 6 ml) and stirred with LiOH.H$_2$O (34 mg, 0.8 mmol) for 2 hours and then heated to 80° C. for 5 minutes. The reaction mixture was evaporated to dryness and triturated with ether to give the title compound as a buff solid (314 mg).

MS: (+ve ion electrospray) m/z 438 [MH$^+$]; $^1$H NMR (400 MHz, D$_6$DMSO) δ (inter alia) 8.63 (1H, d, J 8.4 Hz), 8.58-8.50 (3H, m), 8.24 (1H, d, J 2 Hz), 8.18 (1H, dd, J=2.4 Hz and 8.8 Hz), 7.89 (1H, dd, J=7.2 Hz and 8.4 Hz), 7.45 (1H, d, J 9.2 Hz), 4.93-4.84 (1H, m), 3.57-3.49 (2H, m), 2.45-2.40 (2H, m), 1.47 (6H, d, J 6 Hz).

EXAMPLE 1

Alternative Procedure

3-[5-(5-{3-Chloro-4-[(1-methylethyl)oxy]phenyl}-1,2,4-oxadiazol-3-yl)-1-isoquinolinyl]propanoic acid lithium salt (E1)

A round bottom flask was charged with ethyl 3-[5-(5-{3-chloro-4-[(1-methylethyl)oxy]phenyl}-1,2,4-oxadiazol-3-yl)-1-isoquinolinyl]propanoate (D8; 80 mg, 0.172 mmol), tetrahydrofuran (THF) (4.00 ml), methanol (4.00 ml), water (2 ml) and lithium hydroxide (4.11 mg, 0.172 mmol). The mixture was warmed to 80° C. for 2 h after which time the solvent was removed in vacuo and the resultant red solid triturated with diethyl ether. The resulting slurry was filtered and the solid dried in vacuo to give the title compound as a brick coloured solid (60 mg).

MS: m/z 438, 440 [MH$^+$]

EXAMPLE 2

N-[5-(5-{3-Chloro-4-[(1-methylethyl)oxy]phenyl}-1,2,4-oxadiazol-3-yl)-1-isoquinolinyl]-β-alanine hydrochloride salt (E2)

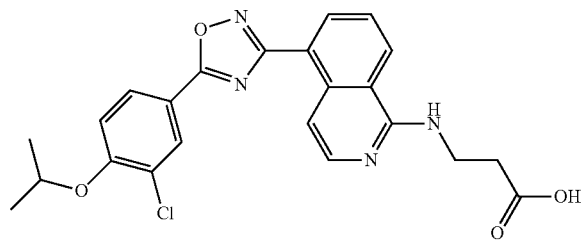

1,1-Dimethylethyl N-[5-(5-{3-chloro-4-[(1-methylethyl)oxy]phenyl}-1,2,4-oxadiazol-3-yl)-1-isoquinolinyl]-β-alaninate (D9; 20 mg, 0.039 mmol) and 0.5M HCl in 1,4-dioxane (10 ml) were stirred at room temperature for 2.5 h. The reaction mixture was then heated to 50° C. for a further 30 minutes, cooled and evaporated to dryness. The resulting solid was triturated with ether and 1,4-dioxane to yield the title compound (20 mg) as a white solid.

MS: (+ve ion electrospray) m/z 452.9 [MH$^+$]; $^1$H NMR (400 MHz, CD$_3$OD) δ (inter alia) 8.71 (1H, dd, J 1.2 Hz and 6.4 Hz), 8.61 (1H, d, J 8.4 Hz), 8.27 (2H, m), 8.17 (1H, m), 7.92 (1H, m), 7.76 (1H, d, J 7.6 Hz), 7.34 (1H, d, J 9.2 Hz), 4.85 (1H, m), 3.89 (2H, m), 2.89 (2H, t, J=6.4 Hz), 1.43 (6H, d, J 6.4 Hz).

EXAMPLE 3

3-[5-(5-{3-Chloro-4-[(1-methylethyl)oxy]phenyl}-1,2,4-oxadiazol-3-yl)-1-isoquinolinyl]-1-propanol (E3)

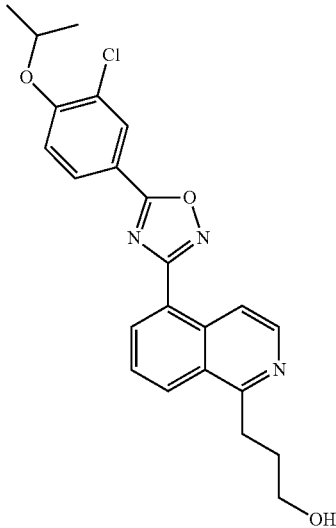

A round bottomed flask was charged with 1-(3-{[(1,1-dimethylethyl)(dimethyl)silyl]oxy}propyl)-N-hydroxy-5-isoquinolinecarboximidamide (D13; 220 mg, 0.612 mmol) and 1,4-dioxane (10 ml). To the stirred solution was added triethylamine (0.1 ml, 0.721 mmol) followed by 3-chloro-4-[(1-methylethyl)oxy]benzoyl chloride (D4; 336 mg, 1.44 mmol) as a solution in acetonitrile (1 ml). The mixture was stirred at room temperature under a blanket of nitrogen for 1 hour. The vessel was then fitted with a reflux condenser and warmed to 145° C. overnight.

The solvent was removed in vacuo and replaced with THF/MeOH/water (2:2:1, 10 ml). To the solution was added lithium hydroxide (88 mg, 0.919 mmol) and the mixture warmed to 80° C. for 3 hours. A further 88 mg of lithium hydroxide was then added and the mixture warmed to 100° C. for 1 hour. The solvent was removed in vacuo and the resultant gum purified by flash column chromatography on silica using 0% to 100% ethyl acetate in cyclohexane then 10% MeOH in DCM as eluent. The relevant fractions were concentrated in vacuo to give a brown gum. The gum was dissolved in DCM and washed with saturated sodium bicarbonate (×2) then brine before being passed through a hydrophobic frit. The solution was concentrated in vacuo to give the title compound as a brown semi-solid (115 mg).

MS: m/z 424, 425 [MH$^+$]

$^1$H NMR (400 MHz, CHLOROFORM-d) δ ppm 8.72 (d, J=6.5 Hz, 1H), 8.55-8.58 (m, 1H), 8.55 (d, J=6.5 Hz, 1H), 8.42 (d, J=8.5 Hz, 1H), 8.30 (d, J=2.5 Hz, 1H), 8.12 (dd, J=8.5, 2.5 Hz, 1H), 7.75 (dd, J=8.5, 7.5 Hz, 1H), 7.09 (d, J=8.5 Hz, 1H), 4.74 (spt, J=6.0 Hz, 1H), 3.77 (t, J=6.0 Hz, 2H), 3.58 (t, J=7.0 Hz, 2H), 2.14-2.26 (m, 2H), 1.47 (d, J=6.0 Hz, 6H)

EXAMPLE 4

1-[5-(5-{3-Chloro-4-[(1-methylethyl)oxy]phenyl}-1,2,4-oxadiazol-3-yl)-1-isoquinolinyl]-4-piperidinecarboxylic acid lithium salt (E4)

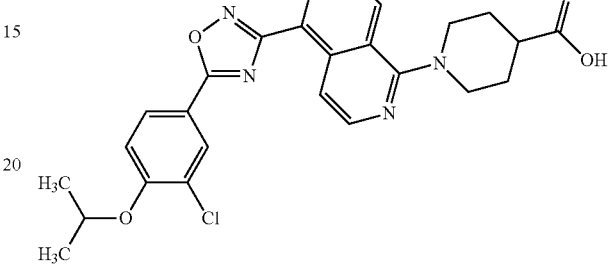

A mixture of ethyl 1-[5-(5-{3-chloro-4-[(1-methylethyl)oxy]phenyl}-1,2,4-oxadiazol-3-yl)-1-isoquinolinyl]-4-piperidinecarboxylate (D14; 35 mg, 0.067 mmol), tetrahydrofuran (THF) (2.0 ml), methanol (2.0 ml), water (1 ml) and lithium hydroxide (1.61 mg, 0.067 mmol) was left to stir at 80° C. for 3 h. The solvent was removed in vacuo and the residue was triturated with diethyl ether. The mixture was filtered to give the title compound as a pale peach coloured solid (20 mg).

MS: m/z 493/495 [MH$^+$]

1H NMR (400 MHz, DMSO-d6) δ ppm 8.46 (d, J=7.0 Hz, 1H), 8.31 (d, J=8.5 Hz, 1H), 8.21-8.26 (m, 2H), 8.14-8.19 (m, 2H), 7.77 (dd, J=8.5, 7.5 Hz, 1H), 7.47 (d, J=9.0 Hz, 1H), 4.90 (spt, J=6.0 Hz, 1H), 3.63-3.70 (m, 2H), 2.87-3.07 (m, 3H), 1.72-2.08 (m, 4H), 1.37 (d, J=6.0 Hz, 6H)

EXAMPLE 5

5-(5-{3-Chloro-4-[(1-methylethyl)oxy]phenyl}-1,2,4-oxadiazol-3-yl)-1-(1-piperazinyl)isoquinoline trifluoroacetic acid salt (E5)

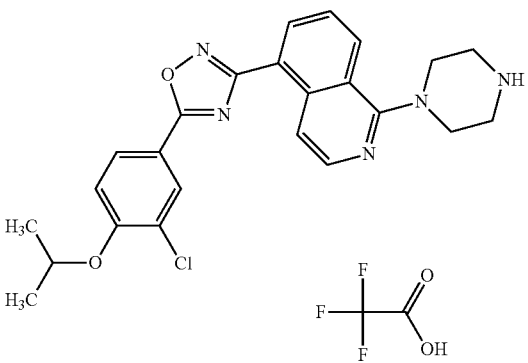

1,1-Dimethylethyl 4-[5-(5-{3-chloro-4-[(1-methylethyl)oxy]phenyl}-1,2,4-oxadiazol-3-yl)-1-isoquinolinyl]-1-piperazinecarboxylate (D15; 24 mg, 0.044 mmol), trifluoroacetic acid (1 ml, 13.0 mmol) and dichloromethane (1 ml) were stirred at room temperature for 1 h. The samples were dissolved in DMSO (1 ml) and purified by Mass Directed Preparative HPLC (supelcosil ABZ+Plus alkylamide phase column), eluting with solvents A/B (A: water+0.1% formic acid, B: MeCN:Water 95:5+0.05% formic acid). The solvent was evaporated in vacuo to give the title compound as a white solid (16 mg).

MS: 450 [MH$^+$]

1H NMR (400 MHz, DMSO-d6) δ ppm 8.89 (br. s., 2H), 8.53 (d, J=7.0 Hz, 1H), 8.45 (d, J=8.5 Hz, 1H), 8.30-8.38 (m, 2H), 8.23 (br. s., 1H), 8.12-8.19 (m, 1H), 7.83 (t, J=7.5 Hz, 1H), 7.48 (d, J=9.0 Hz, 1H), 4.90 (spt, J=6.0 Hz, 1H), 3.35-3.59 (m, 8H), 1.37 (d, J=6.0 Hz, 6H)

EXAMPLE 6

5-(5-{3-Chloro-4-[(1-methylethyl)oxy]phenyl}-1,2,4-oxadiazol-3-yl)isoquinoline (E6)

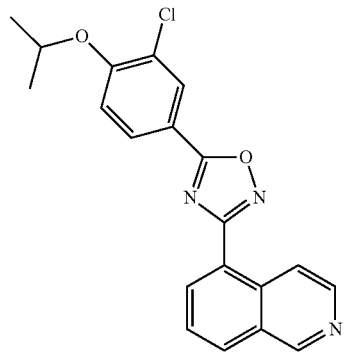

A microwave vial was charged with HATU (2.5 g, 6.57 mmol), triethylamine (1.48 ml, 10.7 mmol), 3-chloro-4-[(1-methylethyl)oxy]benzoic acid (D3; 1.15 g, 5.34 mmol) and N-hydroxy-5-isoquinolinecarboximidamide (D1; 1 g, 5.34 mmol). The solution was stirred at room temperature for 30 minutes. The reaction vessel was sealed and heated under microwave irradiation at 130° C. for 120 min. After cooling, the reaction mixture was filtered. The isolated grey-brown solid was washed with acetonitrile before being dried in vacuo at 60° C. to give the title compound as a grey solid (738 mg, 37%).

MS: m/z [MH$^+$] 366, 368.

1H NMR (400 MHz, CHLOROFORM-d) δ ppm 9.36 (s, 1H), 8.87 (d, J=6.0 Hz, 1H), 8.70 (d, J=6.0 Hz, 1H), 8.63 (dd, J=7.0, 1.0 Hz, 1H), 8.30 (d, J=2.0 Hz, 1H), 8.17 (d, J=8.0 Hz, 1H), 8.12 (dd, J=8.5, 2.0 Hz, 1H), 7.76 (t, J=8.0, 7.0 Hz, 1H), 7.09 (d, J=8.5 Hz, 1H), 4.74 (spt, J=6.0 Hz, 1H), 1.47 (d, J=6.0 Hz, 6H)

EXAMPLE 6

Alternative Preparation 5-(5-{3-Chloro-4-[(1-methylethyl)oxy]phenyl}-1,2,4-oxadiazol-3-yl)isoquinoline (E6)

N-hydroxy-5-isoquinolinecarboximidamide (D1; 1.18 g, 6.30 mmol) was added to a solution of 3-chloro-4-[(1-methylethyl)oxy]benzoyl chloride (D4; 1.54 g, 6.62 mmol), triethylamine (0.966 ml, 6.93 mmol) and N,N-dimethylformamide (DMF) (10 ml) at 0° C. under a blanket of nitrogen. The mixture was allowed to warm to room temperature over 1 h and then heated at 120° C. under nitrogen overnight. The mixture was allowed to cool and then filtered. An off-white solid was collected and washed with acetonitrile to give the title compound (2.01 g).

MS: m/z 366 [MH$^+$]

EXAMPLE 7

1-[5-(5-{3-Chloro-4-[(1-methylethyl)oxy]phenyl}-1,2,4-oxadiazol-3-yl)-1-isoquinolinyl]-3-azetidinecarboxylic acid ammonium salt (E7)

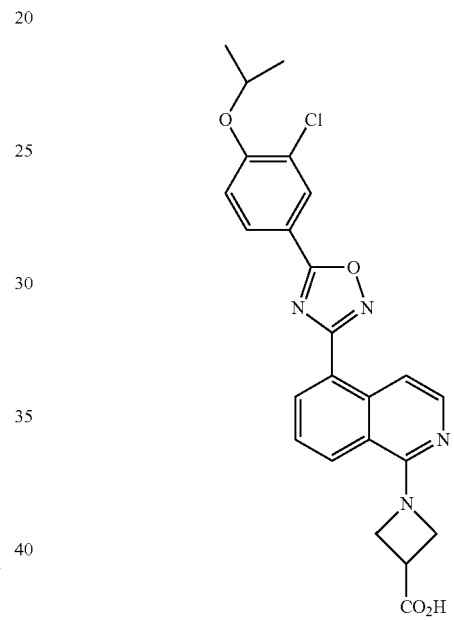

A mixture of 3-azetidinecarboxylic acid (Aldrich; 27.8 mg, 0.275 mmol), sodium hydride (60%; 8.79 mg, 0.220 mmol) in dimethyl sulfoxide (DMSO) (2 ml) was stirred at room temperature for 30 mins. 1-Chloro-5-(5-{3-chloro-4[(1methylethyl)oxy]phenyl}-1,2,4-oxadiazol-3-yl)isoquinoline (D7; 44 mg, 0.110 mmol) was then added and the reaction mixture was heated to 120° C. under nitrogen overnight. The cooled reaction mixture was loaded onto a 10 g SCX column and eluted with acetonitrile followed by 10% ammonia in acetonitrile. The ammonia fractions were combined and evaporated and the residue was dissolved in dichloromethane and then washed with water. The organic phase was passed through a hydrophobic frit and the solvent was removed in vacuo to give the title compound as a yellow solid (9 mg)

MS (ES) $C_{24}H_{21}{}^{35}ClN_4O_4$ requires 464. found 465 [M+H]$^+$.

1H NMR (DMSO-d6) Shift: 8.44 (d, J=7.0 Hz, 1H), 8.10-8.26 (m, 4H), 7.99 (d, J=6.0 Hz, 1H), 7.64-7.73 (m, 1H), 7.46 (d, J=9.0 Hz, 1H), 4.89 (spt, J=6.0 Hz, 1H), 4.36-4.66 (m, 4H), 1.37 (d, J=6.0 Hz, 6H)

EXAMPLE 8

N-[5-(5-{3-Chloro-4-[(1-methylethyl)oxy]phenyl}-1,2,4-oxadiazol-3-yl)-1-isoquinolinyl]-L-alanine (E8)

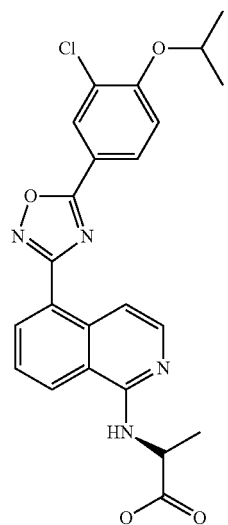

A mixture of L-alanine (27.8 mg, 0.312 mmol) and sodium hydride (60%; 9.99 mg, 0.250 mmol) in dimethyl sulfoxide (DMSO) (2 ml) were stirred at room temp for 30 mins. 1-Chloro-5-(5-{3-chloro-4-[(1-methylethyl)oxy]phenyl}-1,2,4-oxadiazol-3-yl)isoquinoline (D7; 50 mg, 0.125 mmol) was added and the reaction mixture was left to stir at 120° C. under nitrogen for 48 hrs. The reaction mixture was loaded onto a 10 g SCX column and washed with acetonitrile, then eluted with 10% ammonia in acetonitrile. The solvent was evaporated from the appropriate fractions and the residue was dissolved in dichloromethane and washed with water. The organic phase was passed through a hydrophobic frit and the solvent was removed in vacuo to give the title compound as an orange solid (29 mg)

MS (ES) $C_{23}H_{21}{}^{35}ClN_4O_4$ requires 452. found 453 [M+H]+.

1H NMR (DMSO-d6) Shift: 8.68 (d, J=8.5 Hz, 1H), 8.44 (d, J=7.5 Hz, 1H), 8.23 (d, J=2.0 Hz, 1H), 8.16 (dd, J=9.0, 2.0 Hz, 1H), 8.01 (d, J=6.0 Hz, 1H), 7.85 (d, J=6.0 Hz, 1H), 7.70-7.74 (m, 2H), 7.47 (d, J=9.0 Hz, 1H), 4.90 (spt, J=6.0 Hz, 1H), 4.64 (quin, J=7.5 Hz, 1H), 1.53 (d, J=7.5 Hz, 3H), 1.37 (d, J=6.0 Hz, 6H)

EXAMPLE 9

1-[5-(5-{3-Chloro-4-[(1-methylethyl)oxy]phenyl}-1,2,4-oxadiazol-3-yl)-1-isoquinolinyl]proline (E9)

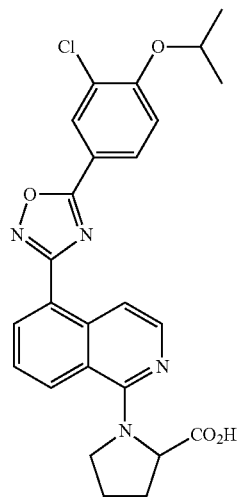

A mixture of sodium hydride (60%; 9.99 mg, 0.250 mmol), dimethyl sulfoxide (DMSO) (2 ml) and proline (36.0 mg, 0.312 mmol) were stirred at room temp under nitrogen for 1 hour. 1-Chloro-5-(5-{3-chloro-4-[(1-methylethyl)oxy]phenyl}-1,2,4-oxadiazol-3-yl)isoquinoline (D7; 50 mg, 0.125 mmol) was added and the reaction mixture was heated at 120° C. under nitrogen for 3 hr. The cooled reaction mixture was loaded onto an SCX column. The column was washed with methanol and then eluted using 2M methanolic ammonia. The appropriate fractions were combined and the solvent was removed in vacuo to give an orange oil which was dissolved in DCM and washed with water. The organic phase was passed through a hydrophobic frit and the solvent was removed in vacuo to give the title compound as an orange solid (40 mg).

MS (ES) $C_{25}H_{23}{}^{35}ClN_4O_4$ requires 478. found 479 [M+H]+.

1H NMR (DMSO-d6) Shift: 12.42 (br. s., 1H), 8.54 (d, J=8.5 Hz, 1H), 8.41 (d, J=7.0 Hz, 1H), 8.22 (d, J=2.0 Hz, 1H), 8.15 (dd, J=9.0, 2.0 Hz, 1H), 8.03 (d, J=6.0 Hz, 1H), 7.93 (d, J=6.0 Hz, 1H), 7.65 (dd, J=8.5, 7.0 Hz, 1H), 7.47 (d, J=9.0 Hz, 1H), 4.90 (spt, J=6.0 Hz, 1H), 4.74 (t, J=7.5 Hz, 1H), 4.08-

4.18 (m, 1H), 3.85-3.93 (m, 1H), 2.29-2.38 (m, 1H), 2.02-2.13 (m, 1H), 1.85-2.02 (m, 2H), 1.37 (d, J=6.0 Hz, 6H)

EXAMPLE 10

1-[5-(5-{3-Chloro-4-[(1-methylethyl)oxy]phenyl}-1,2,4-oxadiazol-3-yl)-1-isoquinolinyl]-3-pyrrolidinecarboxylic acid (E10)

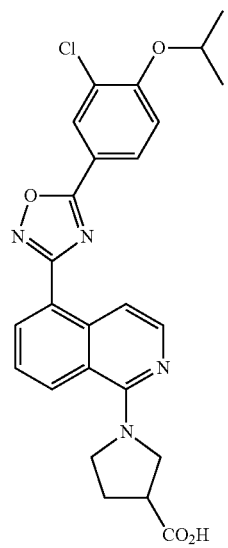

A mixture of 3-pyrrolidinecarboxylic acid (ABCR Product List; 36.0 mg, 0.312 mmol), and sodium hydride (60%; 9.99 mg, 0.250 mmol) in dimethyl sulfoxide (DMSO) (2 ml) were stirred at room temperature for 30 min. 1-Chloro-5-(5-{3-chloro-4-[(1-methylethyl)oxy]phenyl}-1,2,4-oxadiazol-3-yl)isoquinoline (D7; 50 mg, 0.125 mmol) was added and the reaction mixture was left to stir at 120° C. under nitrogen for 3 hours. The cooled reaction mixture was loaded onto an SCX column. The column was flushed with methanol and then the desired product was eluted with 2M ammonia in methanol. The solvent was removed in vacuo from the appropriate fractions to give a yellow solid. Lithium hydroxide (2.99 mg, 0.125 mmol), methanol (2.00 ml), water (1 ml) and tetrahydrofuran (THF) (2.00 ml) were added and the mixture stirred at 80° C. for 1 hour. The solvent was removed in vacuo to give an orange solid which was triturated under ether and filtered. The solid was dissolved in water and then extracted with ether. The organic phase was passed through a hydrophobic frit and the solvent was removed in vacuo to give the title compound as a yellow solid (9 mg).

MS (ES) $C_{25}H_{23}{}^{35}ClN_4O_4$ requires 478. found 479 $[M+H]^+$.

1H NMR (DMSO-d6) Shift: 12.46 (br. s., 1H), 8.47 (d, J=8.5 Hz, 1H), 8.42 (d, J=7.5 Hz, 1H), 8.23 (d, J=2.0 Hz, 1H), 8.16 (dd, J=9.0, 2.0 Hz, 1H), 8.09 (d, J=6.0 Hz, 1H), 7.96 (d, J=6.0 Hz, 1H), 7.67 (t, J=8.5, 7.5 Hz, 1H), 7.47 (d, J=9.0 Hz, 1H), 4.90 (spt, J=6.0 Hz, 1H), 3.90-4.02 (m, 2H), 3.77-3.89 (m, 2H), 3.19 (quin, J=7.0 Hz, 1H), 2.11-2.27 (m, 2H), 1.37 (d, J=6.0 Hz, 6H)

EXAMPLE 11

N-[5-(5-{3-Chloro-4-[(1-methylethyl)oxy]phenyl}-1,2,4-oxadiazol-3-yl)-1-isoquinolinyl]-L-valine (E11)

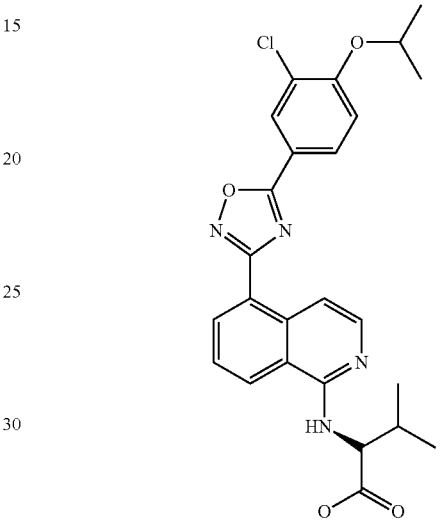

A mixture of L-valine (36.6 mg, 0.312 mmol) and sodium hydride (60%; 9.99 mg, 0.250 mmol) in dimethyl sulfoxide (DMSO) (2 ml) were stirred at room temp for 30 min. 1-Chloro-5-(5-{3-chloro-4-[(1-methylethyl)oxy]phenyl}-1,2,4-oxadiazol-3-yl)isoquinoline (D7; 50 mg, 0.125 mmol) was added and the reaction mixture was stirred at 120° C. under nitrogen for 48 hr. The cooled reaction mixture was loaded onto an SCX column. The column was flushed with acetonitrile and then the desired product was eluted with 20% ammonia in acetonitrile. The solvent was removed in vacuo from the appropriate fractions to give an orange solid which was dissolved in DCM and washed with water. The organics were passed through a hydrophobic frit and the solvent was removed in vacuo to give the title compound as an orange solid (22 mg). MS (ES) $C_{25}H_{25}{}^{35}ClN_4O_4$ requires 480. found 481 $[M+H]^+$.

1H NMR (DMSO-d6) Shift: 8.77 (d, J=8.5 Hz, 1H), 8.44 (d, J=7.5 Hz, 1H), 8.22 (s, 1H), 8.15 (d, J=9.0 Hz, 1H), 8.00 (d, J=6.0 Hz, 1H), 7.86 (d, J=6.0 Hz, 1H), 7.72 (dd, J=8.5, 7.5 Hz, 1H), 7.46 (d, J=9.0 Hz, 1H), 7.38 (d, J=7.5 Hz, 1H), 4.89

(spt, J=6.0 Hz, 1H), 4.49 (t, J=7.5 Hz, 1H), 2.30 (dspt, J=7.5, 6.5 Hz, 1H), 1.37 (d, J=6.0 Hz, 6H), 1.10 (d, J=6.5 Hz, 3H), 1.05 (d, J=6.5 Hz, 3H)

EXAMPLE 12

5-{5-[4-[(1-methylethyl)oxy]-3-(methyloxy)phenyl]-1,2,4-oxadiazol-3-yl}isoquinoline (E12)

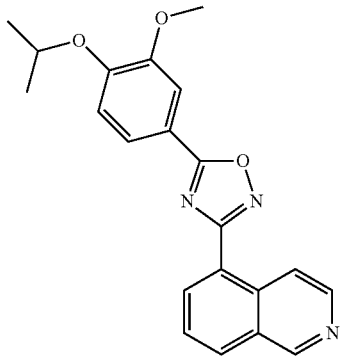

A mixture of 4-[(1-methylethyl)oxy]-3-(methyloxy)benzoic acid (Journal of the American Chemical Society (1955), 77 757-8; 135 mg, 0.641 mmol), HATU (244 mg, 0.641 mmol), Hunig's base (0.3 ml, 1.718 mmol) in N,N-dimethylformamide (DMF) (1 ml) was stirred at room temperature for 1 hr before the addition of N-hydroxy-5-isoquinolinecarboximidamide (D1; 100 mg, 0.534 mmol) in N,N-dimethylformamide (DMF) (1 ml). The reaction mixture was stirred at room temperature for 2-3 hrs and then heated in a microwave at 140° C. for 1.5 hr. The reaction mixture was concentrated in vacuo, dissolved in 1-2 ml of N-methylpyrrolidinone and purified by Preparative HPLC (Waters Sunfire C18 column, eluting with solvents A/B (A: Water+0.1% Formic acid, B: MeCN+0.1% Formic acid)). The solvent was evaporated in vacuo to give the title compound (5 mg).

MS (ES) $C_{21}H_{19}N_3O_3$ requires 361. found 362 $[M+H]^+$.

1H NMR (DMSO-d6) Shift: 9.54 (d, J=1.0 Hz, 1H), 8.79 (dt, J=6.0, 1.0 Hz, 1H), 8.72 (d, J=6.0 Hz, 1H), 8.66 (dd, J=7.5, 1.0 Hz, 1H), 8.45 (dt, J=8.0, 1.0 Hz, 1H), 7.94 (dd, J=8.0, 7.5 Hz, 1H), 7.84 (dd, J=8.5, 2.0 Hz, 1H), 7.71 (d, J=2.0 Hz, 1H), 7.27 (d, J=8.5 Hz, 1H), 4.78 (spt, J=6.0 Hz, 1H), 3.91 (s, 3H), 1.33 (d, J=6.0 Hz, 6H)

EXAMPLE 13

5-(5-{4-[(1,1-dimethylethyl)oxy]phenyl}-1,2,4-oxadiazol-3-yl)isoquinoline (E13)

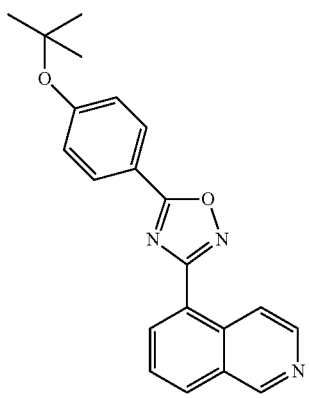

A mixture of 4-[(1,1-dimethylethyl)oxy]benzoic acid (Apin chemicals) (117 mg, 0.603 mmol), HATU (232 mg, 0.610 mmol), Hunig's base (0.263 mL, 1.506 mmol) in N,N-Dimethylformamide (DMF) (1 ml) was stirred for 1 hr before the addition of N-hydroxy-5-isoquinolinecarboximidamide (D1; 94 mg, 0.502 mmol) in N,N-dimethylformamide (DMF) (1 ml). The reaction was left to stir at room temperature for 2 hrs and then heated to 120° C. for 2 hr in the microwave. The reaction mixture was concentrated in vacuo and purified by preparative HPLC (Waters Sunfire C18 column, eluting with solvents A/B (A: Water+0.1% Formic acid, B: MeCN+0.1% Formic acid)) to give the title compound (31.5 mg)

MS (ES) $O_{21}H_{19}N_3O_2$ requires 345. found 346 $[M+H]^+$.

1H NMR (DMSO-d6) Shift: 9.57 (s, 1H), 8.82 (d, J=6.0 Hz, 1H), 8.72 (d, J=6.0 Hz, 1H), 8.66 (d, J=7.5 Hz, 1H), 8.47 (d, J=8.5 Hz, 1H), 8.17 (d, J=9.0 Hz, 2H), 7.96 (dd, J=8.5, 7.5 Hz, 1H), 7.28 (d, J=9.0 Hz, 2H), 1.44 (s, 9H)

EXAMPLE 14

5-{5-[4-(ethyloxy)-3,5-difluorophenyl]-1,2,4-oxadiazol-3-yl}isoquinoline (E14)

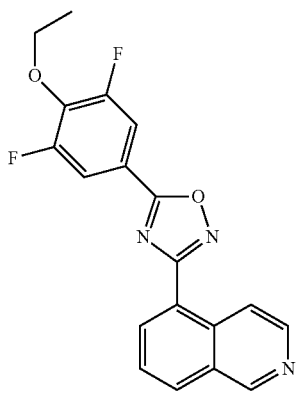

A mixture of 4-(ethyloxy)-3,5-difluorobenzoic acid (JRD Fluorochemicals Ltd; 130 mg, 0.641 mmol), HATU (244 mg, 0.641 mmol), Hunig's base (0.3 mL, 1.718 mmol) in N,N-dimethylformamide (DMF) (1 ml) was stirred at room temperature for 1 hr before the addition of N-hydroxy-5-isoquinolinecarboximidamide (D1; 100 mg, 0.534 mmol) in N,N-dimethylformamide (DMF) (1 ml). The reaction mixture was stirred at room temperature for 2-3 hrs and then heated in a microwave at 140° C. for 1.5 hr. The reaction mixture was concentrated in vacuo and purified by preparative HPLC (Waters Atlantis column, eluting with solvents A/B (A: Water+0.1% Formic acid, B: MeCN+0.1% Formic acid)) to give the title compound (11 mg)

MS (ES) $C_{19}H_{13}F_2N_3O_2$ requires 353. found 354 $[M+H]^+$.

1H NMR (DMSO-d6) Shift: 9.50 (s, 1H), 8.74 (d, J=6.0 Hz, 1H), 8.71 (d, J=6.0 Hz, 1H), 8.60-8.64 (m, 1H), 8.44 (d, J=8.0 Hz, 1H), 8.05 (d, J=8.5 Hz, 2H), 7.92 (dd, J=8.0, 7.5 Hz, 1H), 4.38 (q, J=7.0 Hz, 2H), 1.37 (t, J=7.0 Hz, 3H)

EXAMPLE 15

5-(5-{4-[(1-methylpropyl)oxy]phenyl}-1,2,4-oxadiazol-3-yl)isoquinoline (E15)

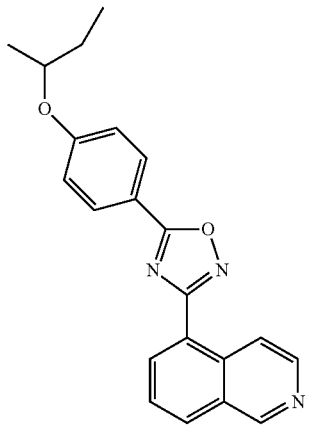

A mixture of 5-(5-{4-[(1-methylpropyl)oxy]phenyl}-1,2,4-oxadiazol-3-yl)isoquinoline, 4-[(1-methylpropyl)oxy]benzoic acid (Journal of the American Chemical Society (1939), 61, 3050; 125 mg, 0.641 mmol), HATU (244 mg, 0.641 mmol), Hunig's base (0.3 mL, 1.718 mmol) in N,N-dimethylformamide (DMF) (1 ml) was stirred at room temperature for 1 hr before the addition of N-hydroxy-5-isoquinolinecarboximidamide (D1; 100 mg, 0.534 mmol) in N,N-dimethylformamide (DMF) (1 ml). The reaction mixture was stirred at room temperature for 2-3 hrs and then heated in a microwave at 140° C. for 1.5 hr. The cooled mixture was concentrated in vacuo, dissolved in 1-2 ml of N-methylpyrrolidinone and purified by preparative HPLC (Waters Sunfire C18 column, eluting with solvents A/B (A: Water+0.1% Formic acid, B: MeCN+0.1% Formic acid)) to give the title compound (16 mg)

MS (ES) $C_{21}H_{19}N_3O_2$ requires 345. found 346 $[M+H]^+$.

1H NMR (DMSO-d6) Shift: 9.56 (s, 1H), 8.82 (d, J=6.0 Hz, 1H), 8.72 (d, J=6.0 Hz, 1H), 8.66 (dd, J=7.5, 1.0 Hz, 1H), 8.47 (d, J=8.0 Hz, 1H), 8.18 (d, J=9.0 Hz, 2H), 7.95 (dd, J=8.0, 7.5 Hz, 1H), 7.21 (d, J=9.0 Hz, 2H), 4.60 (sxt, J=6.0 Hz, 1H), 1.59-1.78 (m, 2H), 1.30 (d, J=6.0 Hz, 3H), 0.95 (t, J=7.5 Hz, 3H)

EXAMPLE 16

5-{5-[3,5-dichloro-4-(propyloxy)phenyl]-1,2,4-oxadiazol-3-yl}isoquinoline (E16)

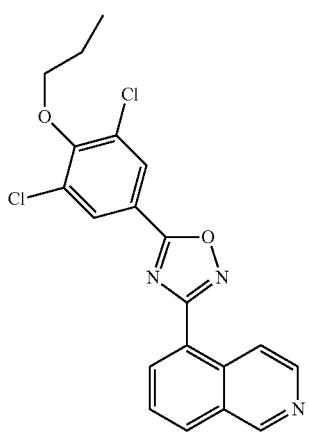

A mixture of 3,5-dichloro-4-(propyloxy)benzoic acid, (Maybridge) (150 mg, 0.603 mmol), HATU (232 mg, 0.610 mmol), Hunig's base (0.263 mL, 1.506 mmol) and N,N-dimethylformamide (DMF) (1 ml) was stirred for 1 hr before the addition of N-hydroxy-5-isoquinolinecarboximidamide (D1; 94 mg, 0.502 mmol) in N,N-dimethylformamide (DMF) (1 ml). The reaction mixture was left to stir for 2 hrs at room temperature and then heated to 120° C. for 2 hr in a microwave. The cooled reaction mixture was concentrated in vacuo and the residue purified by Mass Directed Preparative HPLC (Supelcosil ABZ+Plus column, eluting with solvents A/B (A: Water+0.1% Formic acid, B: MeCN:Water 95:5+0.05% Formic acid)) to give the title compound (23 mg)

MS (ES) $C_{20}H_{15}{}^{35}Cl_2N_3O_2$ requires 400. found 401 $[M+H]^+$.

1H NMR (DMSO-d6) Shift: 9.49 (d, J=1.0 Hz, 1H), 8.74 (dt, J=6.0, 1.0 Hz, 1H), 8.71 (d, J=6.0 Hz, 1H), 8.63 (dd, J=7.5, 1.0 Hz, 1H), 8.43 (dt, J=8.0, 1.0 Hz, 1H), 8.32 (s, 2H), 7.91 (dd, J=8.0, 7.5 Hz, 1H), 4.10 (t, J=6.5 Hz, 2H), 1.84 (qt, J=7.5, 6.5 Hz, 2H), 1.06 (t, J=7.5 Hz, 3H)

EXAMPLE 17

4-[3-(5-Isoquinolinyl)-1,2,4-oxadiazol-5-yl]-1-(2-methylpropyl)-2(1H)-pyridinone (E17)

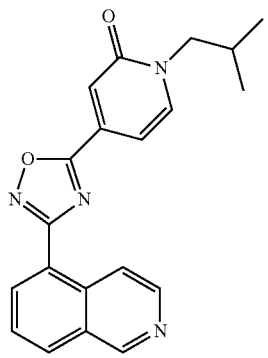

1-(2-Methylpropyl)-2-oxo-1,2-dihydro-4-pyridinecarboxylic acid (D28; 57 mg, 0.294 mmol) was stirred in DMF (0.5 ml) with HATU (122 mg, 0.321 mmol) and DIPEA (0.14 ml, 0.802 mmol) at room temperature for 30 mins before adding a solution of N-hydroxy-5-isoquinolinecarboximidamide (D1, 50 mg, 0.267 mmol) in DMF (0.5 ml). The resulting mixture was heated to 120° C. for 40 mins in a Biotage Initiator microwave. The solvent was removed under vacuum, and the residue was purified by column chromatography on silica, eluting with 0-4% methanol in dichloromethane. The relevant fractions were combined and concentrated under vacuum to give the title compound as a pale yellow oil (5 mg).

MS: m/z 347/348 $[MH^+]$.

$^1$H NMR (400 MHz, $CDCl_3$) δ (inter alia): 9.37 (d, J=1.0 Hz, 1H), 8.85 (dt, J=6.0, 1.0 Hz, 1H), 8.71 (d, J=6.0 Hz, 1H), 8.63 (dd, J=7.5, 1.0 Hz, 1H), 8.19 (dt, J=8.0, 1.0 Hz, 1H), 7.77 (dd, J=8.0, 7.5 Hz, 1H), 7.50 (d, J=2.0 Hz, 1H), 7.45 (d, J=7.0

Hz, 1H), 6.92 (dd, J=7.0, 2.0 Hz, 1H), 3.84 (d, J=7.5 Hz, 2H), 2.18-2.33 (m, 1H), 1.00 (d, J=6.5 Hz, 6H).

EXAMPLE 18

5-(5-{6-[(2,2,2-Trifluoroethyl)oxy]-3-pyridinyl}-1,2,4-oxadiazol-3-yl)isoquinoline (E18)

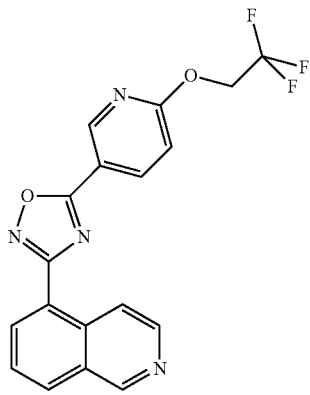

6-[(2,2,2-Trifluoroethyl)oxy]-3-pyridinecarboxylic acid (Fluorochem; 130 mg, 0.642 mmol) was stirred in DMF (1 ml) with HATU (244 mg, 0.642 mmol) and DIPEA (0.28 ml, 1.605 mmol) at room temperature for 30 mins before adding a solution of N-hydroxy-5-isoquinolinecarboximidamide (D1, 100 mg, 0.535 mmol) in DMF (1 ml). The resulting mixture was heated to 120° C. for 30 mins in a Biotage Initiator microwave. The solvent was removed under vacuum, and the residue was purified by column chromatography on silica, eluting with 0-60% ethyl acetate in cyclohexane. The relevant fractions were combined and concentrated under vacuum to give the title compound as a white solid (28 mg).

MS: m/z 373/374 [MH+].

$^1$H NMR (400 MHz, CDCl$_3$) δ: 9.37 (d, J=1.0 Hz, 1H), 9.09 (dd, J=2.5, 0.5 Hz, 1H), 8.87 (dt, J=6.0, 1.0 Hz, 1H), 8.71 (d, J=6.0 Hz, 1H), 8.65 (dd, J=7.5, 1.0 Hz, 1H), 8.49 (dd, J=9.0, 2.5 Hz, 1H), 8.19 (dt, J=8.0, 1.0 Hz, 1H), 7.78 (dd, J=8.0, 7.5 Hz, 1H), 7.09 (dd, J=9.0, 0.5 Hz, 1H), 4.90 (q, J=8.5 Hz, 2H).

EXAMPLE 19

5-(5-{4-[(Trifluoromethyl)oxy]phenyl}-1,2,4-oxadiazol-3-yl)isoquinoline (E19)

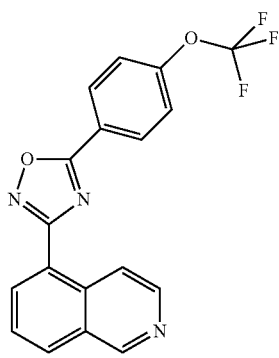

4-[(Trifluoromethyl)oxy]benzoic acid (Aldrich; 132 mg, 0.642 mmol) was stirred in DMF (1 ml) with HATU (244 mg, 0.642 mmol) and DIPEA (0.28 ml, 1.605 mmol) at room temperature for 30 mins before adding a solution of N-hydroxy-5-isoquinolinecarboximidamide (D1, 100 mg, 0.535 mmol) in DMF (1 ml). The resulting mixture was heated to 120° C. for 30 mins in a Biotage Initiator microwave. The solvent was removed under vacuum and the residue was purified by column chromatography on silica, eluting with 0-80% ethyl acetate in cyclohexane. The relevant fractions were combined and concentrated under vacuum to give the title compound as a white solid (88 mg).

MS: m/z 358/359 [MH+].

$^1$H NMR (400 MHz, DMSO-d6) δ: 9.50 (d, J=1.0 Hz, 1H), 8.75 (dt, J=6.0, 1.0 Hz, 1H), 8.71 (d, J=6.0 Hz, 1H), 8.63 (dd, J=7.5, 1.0 Hz, 1H), 8.44 (dt, J=8.0, 1.0 Hz, 1H), 8.41 (d, J=9.0 Hz, 2H), 7.93 (dd, J=8.0, 7.5 Hz, 1H), 7.71 (dq, J=9.0, 1.0 Hz, 2H).

EXAMPLE 20

5-(5-{4-[(Difluoromethyl)oxy]phenyl}-1,2,4-oxadiazol-3-yl)isoquinoline (E20)

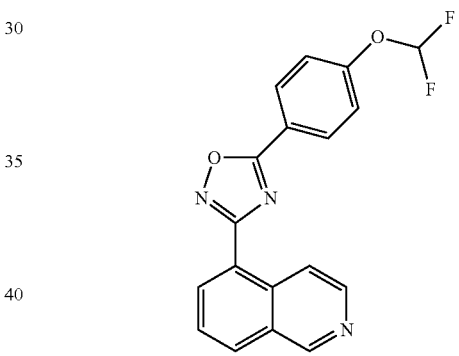

4-[(Difluoromethyl)oxy]benzoic acid (Aldrich; 121 mg, 0.642 mmol) was stirred in DMF (1 ml) with HATU (244 mg, 0.642 mmol) and DIPEA (0.28 ml, 1.605 mmol) at room temperature for 30 mins before adding a solution of N-hydroxy-5-isoquinolinecarboximidamide (D1, 100 mg, 0.535 mmol) in DMF (1 ml). The resulting mixture was heated to 110° C. for 2 hrs in a Biotage Initiator microwave. The solvent was removed under vacuum and the residue was purified by column chromatography on silica, eluting with 0-100% ethyl acetate in cyclohexane. The relevant fractions were combined and concentrated under vacuum to provide a crude material, which was further purified by Mass Directed Preparative HPLC (Supelcosil ABZ+Plus column, eluting with solvents A/B (A: Water+0.1% Formic acid, B: MeCN:Water 95:5+0.05% Formic acid)) to give the title compound as a white solid (48 mg).

MS: m/z 340/341 [MH+].

$^1$H NMR (400 MHz, CDCl$_3$) δ: 9.36 (s, 1H), 8.87 (d, J=6.0 Hz, 1H), 8.71 (d, J=6.0 Hz, 1H), 8.64 (dd, J=7.5, 1.0 Hz, 1H), 8.31 (d, J=9.0 Hz, 2H), 8.18 (d, J=8.0 Hz, 1H), 7.77 (t, J=8.0, 7.5 Hz, 1H), 7.34 (d, J=9.0 Hz, 2H), 6.66 (t, J=73.0 Hz, 1H).

EXAMPLE 21

5-(5-{2-Chloro-4-[(1-methylethyl)oxy]phenyl}-1,2,4-oxadiazol-3-yl)isoquinoline (E21)

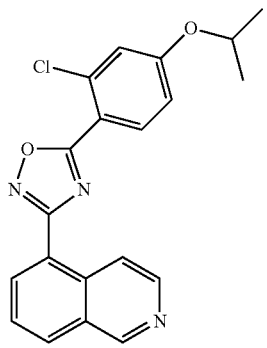

N-hydroxy-5-isoquinolinecarboximidamide (D1, 30 mg, 0.160 mmol) was stirred in DMF (0.7 ml) with methyl 2-chloro-4-[(1-methylethyl)oxy]benzoate (D32; 40.3 mg, 0.176 mmol) and sodium hydride (60%; 4.61 mg, 0.115 mmol) in a Biotage Initiator microwave at 100° C. for 30 mins. The cooled mixture was concentrated under vacuum and the residue was purified by Mass Directed Preparative HPLC (Supelcosil ABZ+Plus column, eluting with solvents A/B (A: Water+0.1% Formic acid, B: MeCN:Water 95:5+0.05% Formic acid)) to give the title compound as a pale yellow solid (8 mg).

MS: m/z 366/368 [MH$^+$].

$^1$H NMR (400 MHz, CDCl$_3$) δ: 9.36 (d, J=1.0 Hz, 1H), 8.93 (dt, J=6.0, 1.0 Hz, 1H), 8.69 (d, J=6.0 Hz, 1H), 8.65 (dd, J=7.5, 1.0 Hz, 1H), 8.18 (d, J=9.0 Hz, 1H), 8.17 (dt, J=8.0, 1.0 Hz, 1H), 7.76 (dd, J=8.0, 7.5 Hz, 1H), 7.10 (d, J=2.5 Hz, 1H), 6.96 (dd, J=9.0, 2.5 Hz, 1H), 4.67 (spt, J=6.0 Hz, 1H), 1.41 (d, J=6.0 Hz, 6H).

EXAMPLE 22

3-[5-(5-{3-chloro-4-[(cyclopropylmethyl)oxy]phenyl}-1,2,4-oxadiazol-3-yl)-1-isoquinolinyl]propanoic acid (E22)

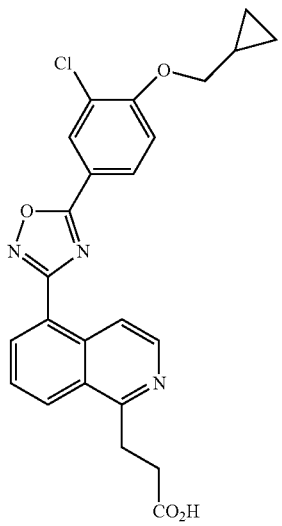

A solution of 1,1-dimethylethyl 3-[5-(5-{3-chloro-4-[(cyclopropylmethyl)oxy]phenyl}-1,2,4-oxadiazol-3-yl)-1-isoquinolinyl]propanoate (D45; 22 mg, 0.043 mmol) in 4N HCl in 1,4-dioxane (4 ml) was allowed to stand at room temperature for 2 h. The solvent was evaporated to give a white solid, which was triturated with dry ether to give a white solid (15 mg). The sample was dissolved in NMP (0.5 ml) and purified by Mass Directed Preparative HPLC (Supelcosil ABZ+Plus column, eluting with solvents A/B (A: Water+0.1% Formic acid, B: MeCN:Water 95:5+0.05% Formic acid)). The solvent was evaporated in vacuo to give the title compound (5 mg).

MS (ES) C$_{24}$H$_{20}$$^{35}$ClN$_3$O$_4$ requires 449. found 450 [M+H]$^+$.

1H NMR (DMSO-d6) Shift: 12.03 (br. s., 1H), 8.54-8.62 (m, 4H), 8.25 (d, J=2.0 Hz, 1H), 8.17 (dd, J=9.0, 2.0 Hz, 1H), 7.89 (dd, J=8.5, 7.5 Hz, 1H), 7.41 (d, J=9.0 Hz, 1H), 4.09 (d, J=7.0 Hz, 2H), 3.61 (t, J=7.0 Hz, 2H), 2.89 (t, J=7.0 Hz, 2H), 1.26-1.37 (m, 1H), 0.60-0.66 (m, 2H), 0.39-0.43 (m, 2H)

EXAMPLE 23

3-[5-(5-{3-Chloro-4-[(difluoromethyl)oxy]phenyl}-1,2,4-oxadiazol-3-yl)-1-isoquinolinyl]propanoic acid (E23)

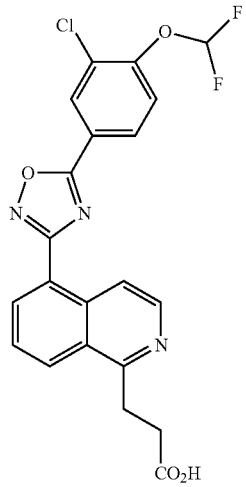

1,1-Dimethylethyl 3-[5-(5-{3-chloro-4-[(difluoromethyl)oxy]phenyl}-1,2,4-oxadiazol-3-yl)-1-isoquinolinyl]propanoate (D46; 32 mg, 0.064 mmol) was dissolved in 4M hydrogen chloride in 1,4-dioxane, and the solution allowed to stand at room temperature for 2 h. The solvent was evaporated in vacuo to give a white solid which was triturated under dry ether (3×5 ml) to give a white solid. The sample was dissolved in 1:1 MeOH:DMSO (1 ml) and purified by Mass Directed Preparative HPLC (Supelcosil ABZ+Plus column, eluting with solvents NB (A: Water+0.1% Formic acid, B: MeCN:Water 95:5+0.05% Formic acid)). The solvent was evaporated in vacuo to give the title compound as a white solid (12.8 mg)

MS (ES) C$_{21}$H$_{14}$$^{35}$ClF$_2$N$_3$O$_4$ requires 445. found 446 [M+H]$^+$.

1H NMR (DMSO-d6) Shift: 12.04 (br. s., 1H), 8.55-8.65 (m, 4H), 8.43 (s, 1H), 8.30 (d, J=8.5 Hz, 1H), 7.91 (dd, J=8.5, 7.5 Hz, 1H), 7.67 (d, J=8.5 Hz, 1H), 7.54 (t, J=72.0 Hz, 1H), 3.62 (t, J=7.0 Hz, 2H), 2.89 (t, J=7.0 Hz, 2H), poor lineshape precludes the observation of fine couplings <2 Hz.

EXAMPLE 24

3-[5-(5-{3-Chloro-4-[(2,2,2-trifluoroethyl)oxy]phenyl}-1,2,4-oxadiazol-3-yl)-1-isoquinolinyl]propanoic acid hydrochloride (E24)

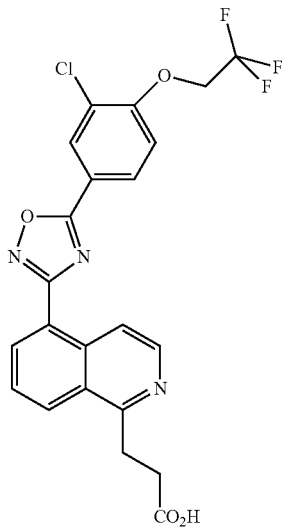

1,1-Dimethylethyl 3-[5-(5-{3-chloro-4-[(2,2,2-trifluoroethyl)oxy]phenyl}-1,2,4-oxadiazol-3-yl)-1-isoquinolinyl]propanoate (D47; 55 mg, 0.103 mmol) was dissolved in 4N HCl in 1,4-dioxane (4 ml) and the solution allowed to stand at room temperature for 2 h. A white precipitate was formed which was filtered off, washed with dry ether and dried to give the title compound as a white solid (33 mg)

MS (ES) $C_{22}H_{15}{}^{35}ClF_3N_3O_4$ requires 477. found 478 [M+H]$^+$.

1H NMR (DMSO-d6) Shift: 8.82 (d, J=6.5 Hz, 1H), 8.77 (d, J=8.5 Hz, 1H), 8.72 (d, J=7.0 Hz, 1H), 8.63 (d, J=6.5 Hz, 1H), 8.33 (d, J=2.0 Hz, 1H), 8.26 (dd, J=9.0, 2.0 Hz, 1H), 8.03 (dd, J=8.5, 7.0 Hz, 1H), 7.59 (d, J=9.0 Hz, 1H), 5.09 (q, J=8.5 Hz, 2H), 3.73 (t, J=7.0 Hz, 2H), 2.92 (t, J=7.0 Hz, 2H), degree of HCl salt undetermined.

EXAMPLE 25

3-[5-(5-{3-Cyano-4-[(cyclopropylmethyl)oxy]phenyl}-1,2,4-oxadiazol-3-yl)-1-isoquinolinyl]propanoic acid (E25)

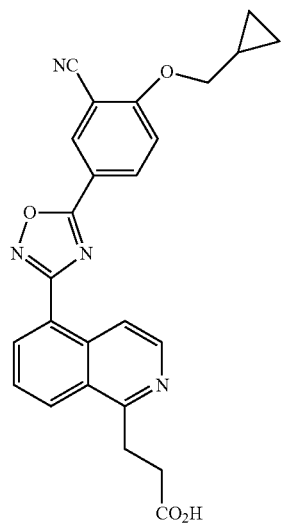

1,1-Dimethylethyl 3-[5-(5-{3-cyano-4-[(cyclopropylmethyl)oxy]phenyl}-1,2,4-oxadiazol-3-yl)-1-isoquinolinyl]propanoate (D48; 36 mg, 0.072 mmol) was dissolved in 4N HCl in 1,4-dioxane (4 ml) and the mixture was allowed to stand at room temperature for 4.5 h. The solvent was evaporated in vacuo and the residue triturated with dry ether to give a white solid which was dissolved in N-methyl-2-pyrrolidinone (1 ml) and purified by Mass Directed Preparative HPLC (Supelcosil ABZ+Plus column, eluting with solvents A/B (A: Water+0.1% Formic acid, B: MeCN:Water 95:5+0.05% Formic acid)). The solvent was dried under a stream of nitrogen to give the title compound as a white solid (10.5 mg)

MS (ES) $C_{25}H_{20}N_4O_4$ requires 440. found 441 [M+H]$^+$.

1H NMR (DMSO-d6) Shift: 8.54-8.63 (m, 5H), 8.47 (dd, J=9.0, 2.0 Hz, 1H), 7.90 (dd, J=8.0, 7.5 Hz, 1H), 7.52 (d, J=9.0 Hz, 1H), 4.18 (d, J=7.5 Hz, 2H), 3.61 (t, J=7.0 Hz, 2H), 2.88 (t, J=7.0 Hz, 2H), 1.22-1.39 (m, 1H), 0.61-0.69 (m, 2H), 0.39-0.47 (m, 2H)

EXAMPLE 26

3-[5-(5-{3-Cyano-4-[(1-methylethyl)oxy]phenyl}-1,2,4-oxadiazol-3-yl)-1-isoquinolinyl]propanoic acid hydrochloride (E26)

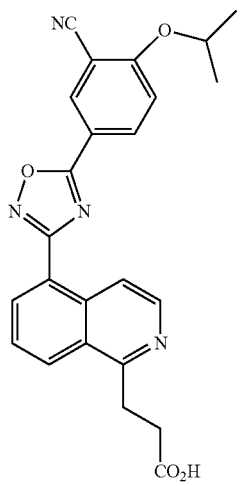

1,1-Dimethylethyl 3-[5-(5-{3-cyano-4-[(1-methylethyl)oxy]phenyl}-1,2,4-oxadiazol-3-yl)-1-isoquinolinyl]propanoate (D52; 66 mg, 0.133 mmol) was dissolved in 4M hydrogen chloride in 1,4-dioxane (4 ml) and the mixture allowed to stand at room temperature for 2 h. The solvent was evaporated in vacuo to give a colourless gum which was triturated under dry ether (5 ml) to give the title compound as a white solid (54 mg).

MS (ES) $C_{24}H_{20}{}^{35}ClN_4O_4$ requires 428. found 429 [M+H]$^+$.

1H NMR (DMSO-d6) Shift: 8.85 (d, J=6.5 Hz, 1H), 8.79 (d, J=8.5 Hz, 1H), 8.72 (d, J=7.5 Hz, 1H), 8.64 (d, J=6.5 Hz, 1H), 8.59 (d, J=2.0 Hz, 1H), 8.47 (dd, J=9.0, 2.0 Hz, 1H), 8.05

(dd, J=8.5, 7.5 Hz, 1H), 7.59 (d, J=9.0 Hz, 1H), 5.00 (spt, J=6.0 Hz, 1H), 3.74 (t, J=7.5 Hz, 2H), 2.93 (t, J=7.5 Hz, 2H), 1.40 (d, J=6.0 Hz, 6H)

EXAMPLE 27

3-[5-(5-{5-Chloro-6-[(1-methylethyl)oxy]-3-pyridinyl}-1,2,4-oxadiazol-3-yl)-1-isoquinolinyl]propanoic acid (E27)

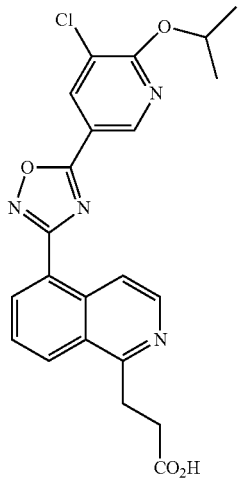

1,1-Dimethylethyl 3-[5-(5-{5-chloro-6-[(1-methylethyl)oxy]-3-pyridinyl}-1,2,4-oxadiazol-3-yl)-1-isoquinolinyl]propanoate (D53; 54 mg, 0.111 mmol) was dissolved in 4M hydrogen chloride in 1,4-dioxane (10 ml) and the mixture allowed to stand at room temperature for 2 h. The solvent was evaporated in vacuo to give a colourless gum which was triturated under dry ether (5 ml) to give a white solid which was dissolved in NMP (0.5 ml) and purified by Mass Directed Preparative HPLC (Supelcosil ABZ+Plus column, eluting with solvents A/B (A: Water+0.1% Formic acid, B: MeCN:Water 95:5+0.05% Formic acid)). The solvent was evaporated in vacuo to give the title compound (2.2 mg)

MS (ES) $C_{22}H_{19}^{35}ClN_4O_4$ requires 438. found 439/440 $[M+H]^+$.

1H NMR (DMSO-d6) Shift: 8.98 (1H, d), 8.57 (5H, m), 7.89 (1H, dd), 5.46 (spt, 1H), 3.61 (t, 2H), 2.88 (t, 2H), 1.40 (d, 6H)

EXAMPLE 28

3-[5-(5-{3-Cyano-4-[(2,2,2-trifluoroethyl)oxy]phenyl}-1,2,4-oxadiazol-3-yl)-1-isoquinolinyl]propanoic acid (E28)

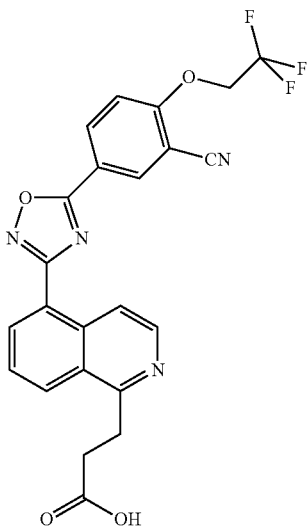

1,1-Dimethylethyl 3-[5-(5-{3-cyano-4-[(2,2,2-trifluoroethyl)oxy]phenyl}-1,2,4-oxadiazol-3-yl)-1-isoquinolinyl]propanoate (D49; 164 mg, 0.313 mmol) was stirred in 4M HCl in dioxane (3 ml) at room temperature for 2.5 hrs. The solvent was removed under vacuum and the residue was triturated under diethyl ether. Filtration provided a solid that was dried in a vacuum oven to give the title compound as a white solid (125 mg).

MS: m/z 469/470 $[MH^+]$.

$^1$H NMR (400 MHz, DMSO-d6) δ: 8.67-8.81 (m, 4H), 8.62 (d, J=6.0 Hz, 1H), 8.58 (dd, J=9.0, 2.0 Hz, 1H), 8.02 (t, J=8.0 Hz, 1H), 7.69 (d, J=9.0 Hz, 1H), 5.20 (q, J=8.5 Hz, 2H), 3.70 (t, J=7.0 Hz, 2H), 2.92 (t, J=7.0 Hz, 2H).

EXAMPLE 29

3-(5-{5-[3-Cyano-4-(3-fluoro-1-pyrrolidinyl)phenyl]-1,2,4-oxadiazol-3-yl}-1-isoquinolinyl)propanoic acid (E29)

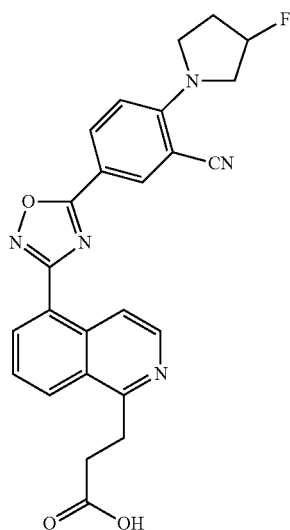

1,1-Dimethylethyl 3-(5-{5-[3-cyano-4-(3-fluoro-1-pyrrolidinyl)phenyl]-1,2,4-oxadiazol-3-yl}-1-isoquinolinyl)propanoate (D51; 14 mg, 0.027 mmol) was stirred in 4M HCl in dioxane (1 ml) at room temperature for 7 hrs. The mixture was concentrated in a blow down unit and the residue was purified by Mass Directed Preparative HPLC (Supelcosil ABZ+Plus column, eluting with solvents A/B (A: Water+0.1% Formic acid, B: MeCN:Water 95:5+0.05% Formic acid)) to give the title compound as a white solid (2 mg).

MS: m/z 458/459 $[MH^+]$.

$^1$H NMR (DMSO-d6) δ: 8.54-8.61 (m, 4H), 8.34 (d, J=2.0 Hz, 1H), 8.18 (dd, J=9.0, 2.0 Hz, 1H), 7.88 (dd, J=8.0, 7.5 Hz, 1H), 7.05 (d, J=9.0 Hz, 1H), 5.43-5.61 (m, 1H), 3.76-4.10 (m, 4H), 3.61 (t, J=7.0 Hz, 2H), 2.88 (t, J=7.0 Hz, 2H), 2.12-2.42 (m, 2H).

EXAMPLE 30

4-[5-(5-{5-Chloro-6-[(1-methylethyl)oxy]-3-pyridinyl}-1,2,4-oxadiazol-3-yl)-1-isoquinolinyl]butanoic acid (E30)

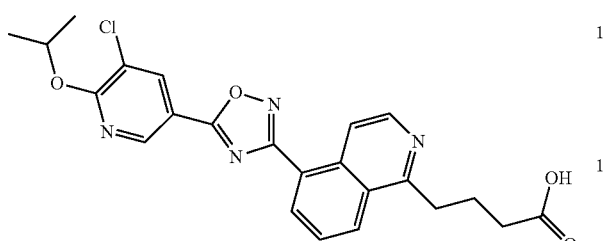

Sodium hydroxide (50 mg) was added to a suspension of ethyl 4-[5-(5-{5-chloro-6-[(1-methylethyl)oxy]-3-pyridinyl}-1,2,4-oxadiazol-3-yl)-1-isoquinolinyl]butanoate (D44; 0.36 g) in isopropanol (5 ml) and water (5 ml). The reaction mixture was heated to 80° C. for 2 hours. After cooling, isopropanol was evaporated in vacuo and the remaining aqueous solution was acidified with aq. HCl (0.5 N) to pH=5. The solid was collected and washed with DMF (5 ml) and acetonitrile (5 ml) to afford the title compound (0.19 g). δH (DMSO-d$_6$, 400 MHz): 1.39 (6H, d), 2.05 (2H, m), 2.40 (2H, m), 3.37 (2H, m), 5.46 (1H, m), 7.88 (1H, dd), 8.57 (5H, m), 8.97 (1H, d), 12.04 (1H, s). MS (ES): $C_{23}H_{21}ClN_4O_4$ requires 452. found 453.2 (M+H$^+$).

EXAMPLE 31

4-[5-(5-{3-chloro-4-[(1-methylethyl)oxy]phenyl}-1,2,4-oxadiazol-3-yl)-1-isoquinolinyl]butanoic acid (E31)

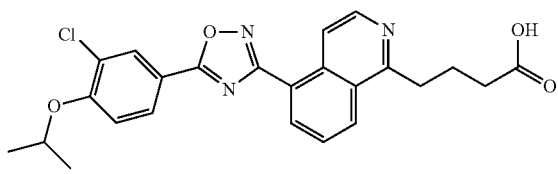

Sodium hydroxide (16 mg) was added to a suspension of ethyl 4-[5-(5-{3-chloro-4-[(1-methylethyl)oxy]phenyl}-1,2,4-oxadiazol-3-yl)-1-isoquinolinyl]butanoate (D41; 0.1 g) in isopropanol (10 ml) and water (10 ml). The reaction mixture was heated to 70° C. for 2 hours. After cooling, isopropanol was evaporated in vacuo and the remaining aqueous solution was acidified with aq. HCl (0.5 N) to pH=1. The aqueous solution was extracted with DCM (2×20 ml). The organic fractions were combined and dried over anhydrous sodium sulphate. The dried solution was filtered and the filtrate was concentrated. The residue was washed with THF (3×10 ml) to afford the title compound (15 mg). δH (DMSO-d$_6$, 400 MHz): 1.37 (6H, d), 2.04 (2H, m), 2.40 (2H, m), 3.34 (2H, m), 4.89 (1H, m), 7.47 (1H, d), 7.88 (1H, dd), 8.17 (1H, dd), 8.24 (1H, d), 8.57 (4H, m), 12.11 (1H, s).

MS (ES): $C_{24}H_{22}ClN_3O_4$ requires 451. found 452.2 (M+H$^+$).

EXAMPLE 32

3-[5-(5-{3-Chloro-4-[(1-methylethyl)oxy]phenyl}-1,2,4-oxadiazol-3-yl)-1-isoquinolinyl]benzoic acid (E32)

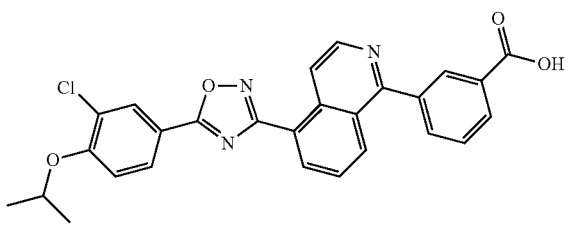

Sodium carbonate (85 mg) and PdCl$_2$(dppf)$_2$ (50 mg) were added sequentially to a suspension of 1-bromo-5-(5-{3-chloro-4-[(1-methylethyl)oxy]phenyl}-1,2,4-oxadiazol-3-yl)isoquinoline (D40; 180 mg) and 3-(dihydroxyboranyl) benzoic acid (Aldrich; 99 mg) in 1,2-dimethoxyethane (DME; 2 ml), ethanol (1 ml) and water (1 ml). The resulting suspension was heated to 80° C. and stirred for overnight. The solvent was evaporated in vacuo and the residue was purified by MDAP to give the title compound (20 mg). δH (DMSO-d$_6$, 400 MHz): 1.37 (6H, d), 4.90 (1H, m), 7.48 (1H, d), 7.73 (1H, t), 7.86 (1H, t), 7.95 (1H, dd), 8.19 (5H, m), 8.60 (1H, dd), 8.78 (2H, m), 13.17 (1H, br s).

MS (ES): $C_{27}H_{20}ClN_3O_4$ requires 485. found 486.2 (M+H$^+$).

S1P1 GTPγS Binding Assay

For membrane preparations all steps were performed at 4° C. Rat hepatoma cells stably expressing the human S1P1 receptor or Rat Basophilic Leukaemia cells (RBL) stably expressing human S1P3 receptor were grown to 80% confluency before being harvested into 10 ml Phospho-Buffered Saline (PBS) and centrifuged at 1200 rpm for minutes. After removal of the supernatant, the pellet was re-suspended and cells were homogenised within a glass Waring blender for 2 bursts of 15 secs in 200 mls of buffer (50 mM HEPES, 1 mM leupeptin, 25 µg/ml bacitracin, 1 mM EDTA, 1 mM PMSF, 2 µM pepstatin A). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and pepstatin A. The material was then forced through a 0.6 mm needle, made up to the required volume, (usually ×4 the volume of the original cell pellet), aliquoted and stored frozen at −80° C.

Human S1P1 rat hepatoma membranes (1.5 µg/well) were adhered to a wheatgerm agglutinin (WGA)-coated scintillation proximity assay (SPA) beads (0.125 mg/well) in assay buffer (HEPES 20 mM, MgCl$_2$ 10 mM, NaCl 100 mM and pH adjusted to 7.4 using KOH 5M, GDP 10 µM FAC (final assay concentration) and saponin 90 µg/ml FAC was also added).

After 30 minutes pre-coupling on ice the bead and membrane suspension was dispensed into a white Greiner polypropylene LV384-well plate (5 µl/well), containing 0.1 µl of the compound. 5 µl/well [$^{35}$S]-GTPγS (0.5 nM final radioligand conc) made up in assay buffer was then added to agonist plates. The final assay cocktail (10.10) was then centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

Examples 1 to 6 of the invention had a pEC50>6 in this assay.

Alternative Method for S1P1 GTPγS Assay $S_1P_1$ expressing RH7777 membranes (1.5 μg/well) membranes (1.5 μg/well) were homogenised by passing through a 23G needle. These were then adhered to WGA-coated SPA beads (0.125 mg/well) in assay buffer (HEPES 20 mM, $MgCl_2$ 10 mM, NaCl 100 mM and pH adjusted to 7.4 using KOH 5M). GDP 10 μM FAC and saponin 90 μg/ml FAC were also added After 30 minutes precoupling on ice, the bead and membrane suspension was dispensed into white Greiner polypropylene LV 384-well plates (5 μl/well), containing 0.1 μl of compound. 5 μl/well [$^{35}$S]-GTPγS (0.5 nM for $S_1P_1$ or 0.3 nM for $S_1P_3$ final radioligand concentration) made in assay buffer was then added to the plates. The final assay cocktail (10.1 μl) was then sealed, spun on a centrifuge, then read immediately on a Viewlux instrument.

In one of the above S1P1 GTPγS binding assays:
Examples 2, 3, 6, 7, 8, 16, 22 to 25, 28, 29 and 31 to 32 had a pEC50>7.
Examples 1, 4, 24, 26, 27 and 30 had a pEC50≧8.

S1P3 GTPγS Binding Assay

S1P3 membranes from rat basophilic leukaemia cells (RBL-2H3)(1.5 μg/well) were adhered to WGA-coated SPA beads (0.125 mg/well) in assay buffer (HEPES 20 mM, $MgCl_2$ 3 mM, NaCl 100 mM and pH adjusted to 7.4 using KOH 5M), GDP 10 μM FAC and saponin 90 μg/ml FAC was also added).

After 30 minutes pre-coupling on ice the bead and membrane suspension was dispensed into a white Greiner polypropylene LV384-well plate (5 μl/well), containing 0.1 μl of the compound. 5 μl/well [$^{35}$S]-GTPγS (0.5 nM final radioligand conc) made up in assay buffer was then added to agonist plates. The final assay cocktail (10.1 μl) was centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

Examples 1 to 6 had a pEC50<4.5.

Alternative Method for S1P3 GTPγS Assay $S_1P_3$ expressing RBL membranes (1.5 μg/well) were homogenised by passing through a 23G needle. These were then adhered to WGA-coated SPA beads (0.125 mg/well) in assay buffer (HEPES 20 mM, $MgCl_2$ 10 mM, NaCl 100 mM and pH adjusted to 7.4 using KOH 5M). GDP 10 μM FAC and saponin 90 μg/ml FAC were also added After 30 minutes precoupling on ice, the bead and membrane suspension was dispensed into white Greiner polypropylene LV 384-well plates (5 μl/well), containing 0.1 μl of compound. 5 μl/well [$^{35}$S]-GTPγS (0.5 nM for $S_1P_1$ or 0.3 nM for $S_1P_3$ final radioligand concentration) made in assay buffer was then added to the plates. The final assay cocktail (10.1 μl) was then sealed, spun on a centrifuge, then read immediately on a Viewlux instrument.

In one of the above S1P3 GTPγS binding assays:
Examples 7 to 29 had a pEC50 of <4.5.
Examples 30 to 32 had a pEC50 of <5.
Example 4 had a pEC50 of 5.5.

The invention claimed is:

1. A compound of formula (I) or a salt thereof:

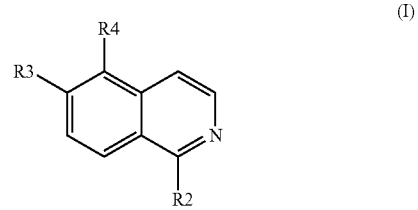

(I)

wherein
one of $R_3$ and $R_4$ is hydrogen and the other is (a)

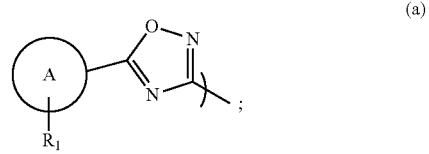

(a)

A is a phenyl or a 5 or 6-membered heteroaryl ring;
$R_1$ is hydrogen or up to two substituents independently selected from halogen, $C_{(1-4)}$alkyl, $C_{(1-4)}$alkoxy, trifluoromethoxy, difluoromethoxy, (2,2,2-trifluoroethyl)oxy, cyclopropyloxy, (cyclopropylmethyl)oxy, 3-oxetanyloxy, trifluoromethyl, cyano, $C_{(1-4)}$alkenoxy and pyrollidinyl substituted by halogen;
$R_2$ is hydrogen, —($C_{1-5}$alkyl)COOH, or —NH($C_{1-5}$alkyl)COOH, —($C_{1-5}$alkyl)OH, —($C_{1-4}$alkyl)CONR$_5$R$_6$, —($C_{1-2}$alkyl)NR$_5$R$_6$, —($C_{1-4}$alkyl)NR$_8$COR$_9$, —($C_{1-4}$alkyl)NR$_{10}$SO$_2$R$_{11}$, —(CH$_2$)$_2$SO$_2$Me, —NR$_5$R$_6$ or any one of groups (i) to (xii):

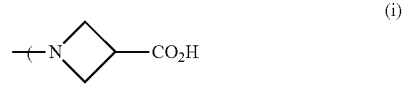

(i)

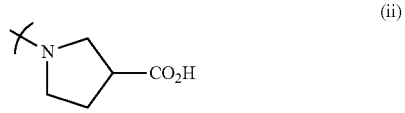

(ii)

(iii)

-continued (iv) 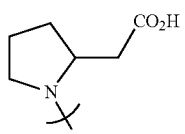

(v) 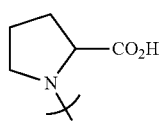

(vi) 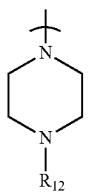

(vii) 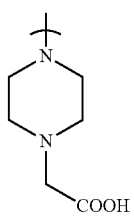

(viii) 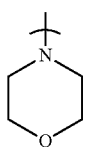

(ix) 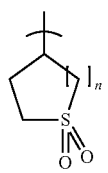

(x) 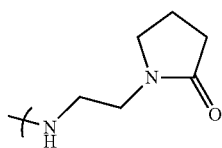

(xi) 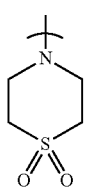

(xii) 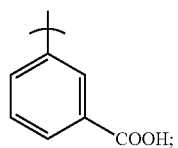

$R_{5-8}$, $R_{10}$ and $R_{12}$ are each independently selected from hydrogen and $C_{1-3}$alkyl;

$R_9$ and $R_{11}$ are each independently selected from $C_{1-3}$alkyl; and n is 1 or 2.

2. A compound according to claim 1 wherein,
$R_3$ is hydrogen and $R_4$ is (a); and
A is phenyl or pyridyl; and
$R_1$ is up to two substituents independently selected from halogen, $C_{(1-4)}$alkoxy, trifluoromethoxy, difluoromethoxy, propenyloxy, (cyclopropylmethyl)oxy, cyano and pyrollidinyl substituted by fluorine;
$R_2$ is hydrogen, —($C_{2-3}$alkyl)COOH, —NH($C_2$alkyl)COOH, —($C_3$alkyl)OH, group (i), group (ii), group (iii), group (v), group (vi) or group (xii); and
$R_{12}$ is hydrogen.

3. A compound selected from:
3-[5-(5-{3-chloro-4-[(1-methylethyl)oxy]phenyl}-1,2,4-oxadiazol-3-yl)-1-isoquinolinyl]propanoic acid;
N-[5-(5-{3-chloro-4-[(1-methylethyl)oxy]phenyl}-1,2,4-oxadiazol-3-yl]-1-isoquinolinyl]-β-alanine;
3-[5-(5-{3-Chloro-4-[(1-methylethyl)oxy]phenyl}-1,2,4-oxadiazol-3-yl)-1-isoquinolinyl]-1-propanol;
5-(5-{3-chloro-4-[(1-methylethyl)oxy]phenyl}-1,2,4-oxadiazol-3-yl)isoquinoline;
1-[5-(5-{3-chloro-4-[(1-methylethyl)oxy]phenyl}-1,2,4-oxadiazol-3-yl)-1-isoquinolinyl]-4-piperidinecarboxylic acid;
5-(5-{3-chloro-4-[(1-methylethyl)oxy]phenyl}-1,2,4-oxadiazol-3-yl)-1-(1-piperazinyl)isoquinoline;
1-[5-(5-{3-Chloro-4-[(1-methylethyl)oxy]phenyl}-1,2,4-oxadiazol-3-yl)-1-isoquinolinyl]-3-azetidinecarboxylic acid ammonium salt;
N-[5-(5-{3-Chloro-4-[(1-methylethyl)oxy]phenyl}-1,2,4-oxadiazol-3-yl)-1-isoquinolinyl]-L-alanine;
1-[5-(5-{3-Chloro-4-[(1-methylethyl)oxy]phenyl}-1,2,4-oxadiazol-3-yl)-1-isoquinolinyl]proline;
1-[5-(5-{3-Chloro-4-[(1-methylethyl)oxy]phenyl}-1,2,4-oxadiazol-3-yl)-1-isoquinolinyl]-3-pyrrolidinecarboxylic acid;
N-[5-(5-{3-Chloro-4-[(1-methylethyl)oxy]phenyl}-1,2,4-oxadiazol-3-yl)-1-isoquinolinyl]-L-valine;
5-{5-[4-[(1-methylethyl)oxy]-3-(methyloxy)phenyl]-1,2,4-oxadiazol-3-yl}isoquinoline;
5-(5-{4-[(1,1-dimethylethyl)oxy]phenyl}-1,2,4-oxadiazol-3-yl)isoquinoline;
5-{5-[4-(ethyloxy)-3,5-difluorophenyl]-1,2,4-oxadiazol-3-yl}isoquinoline;
5-(5-{4-[(1-methylpropyl)oxy]phenyl}-1,2,4-oxadiazol-3-yl)isoquinoline;
5-{5-[3,5-dichloro-4-(propyloxy)phenyl]-1,2,4-oxadiazol-3-yl}isoquinoline;
4-[3-(5-Isoquinolinyl)-1,2,4-oxadiazol-5-yl]-1-(2-methylpropyl)-2(1H)-pyridinone;
5-(5-{6-[(2,2,2-Trifluoroethyl)oxy]-3-pyridinyl}-1,2,4-oxadiazol-3-yl)isoquinoline;
5-(5-{4-[(Trifluoromethyl)oxy]phenyl}-1,2,4-oxadiazol-3-yl)isoquinoline;
5-(5-{4-[(Difluoromethyl)oxy]phenyl}-1,2,4-oxadiazol-3-yl)isoquinoline;
5-(5-{2-Chloro-4-[(1-methylethyl)oxy]phenyl}-1,2,4-oxadiazol-3-yl)isoquinoline;
3-[5-(5-{3-chloro-4-[(cyclopropylmethyl)oxy]phenyl}-1,2,4-oxadiazol-3-yl)-1-isoquinolinyl]propanoic acid;
3-[5-(5-{3-Chloro-4-[(difluoromethyl)oxy]phenyl}-1,2,4-oxadiazol-3-yl)-1-isoquinolinyl]propanoic acid;
3-[5-(5-{3-Chloro-4-[(2,2,2-trifluoroethyl)oxy]phenyl}-1,2,4-oxadiazol-3-yl)-1-isoquinolinyl]propanoic acid;
3-[5-(5-{3-Cyano-4-[(cyclopropylmethyl)oxy]phenyl}-1,2,4-oxadiazol-3-yl)-1-isoquinolinyl]propanoic acid;

3-[5-(5-{3-Cyano-4-[(1-methylethyl)oxy]phenyl}-1,2,4-oxadiazol-3-yl)-1-isoquinolinyl]propanoic acid;
3-[5-(5-{5-Chloro-6-[(1-methylethyl)oxy]-3-pyridinyl}-1,2,4-oxadiazol-3-yl)-1-isoquinolinyl]propanoic acid;
3-[5-(5-{3-Cyano-4-[(2,2,2-trifluoroethyl)oxy]phenyl}-1,2,4-oxadiazol-3-yl)-1-isoquinolinyl]propanoic acid;
3-(5-{5-[3-Cyano-4-(3-fluoro-1-pyrrolidinyl)phenyl]-1,2,4-oxadiazol-3-yl}-1-isoquinolinyl)propanoic acid;
4-[5-(5-{5-Chloro-6-[(1-methylethyl)oxy]-3-pyridinyl}-1,2,4-oxadiazol-3-yl)-1-isoquinolinyl]butanoic acid;
4-[5-(5-{3-chloro-4-[(1-methylethyl)oxy]phenyl}-1,2,4-oxadiazol-3-yl)-1-isoquinolinyl]butanoic acid; and
3-[5-(5-{3-Chloro-4-[(1-methylethyl)oxy]phenyl}-1,2,4-oxadiazol-3-yl)-1-isoquinolinyl]benzoic acid or a salt thereof.

4. A pharmaceutical composition comprising a compound according to claim 1.

* * * * *